US011931352B2

(12) United States Patent
Bushweller et al.

(10) Patent No.: US 11,931,352 B2
(45) Date of Patent: Mar. 19, 2024

(54) COMBINATION THERAPIES FOR TREATING CANCER

(71) Applicants: UNIVERSITY OF VIRGINIA PATENT FOUNDATION, Charlottesville, VA (US); UNIVERSITY OF MASSACHUSETTS, Boston, MA (US)

(72) Inventors: John H. Bushweller, Crozet, VA (US); Anuradha Illendula, Crozet, VA (US); Lucio Hernan Castilla, Boston, MA (US); John Anto Pulikkan, Boston, MA (US)

(73) Assignees: UNIVERSITY OF VIRGINIA PATENT FOUNDATION, Charlottesville, VA (US); UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 17/056,459

(22) PCT Filed: May 24, 2019

(86) PCT No.: PCT/US2019/033889
§ 371 (c)(1),
(2) Date: Nov. 18, 2020

(87) PCT Pub. No.: WO2019/226975
PCT Pub. Date: Nov. 28, 2019

(65) Prior Publication Data
US 2021/0205280 A1    Jul. 8, 2021

Related U.S. Application Data

(60) Provisional application No. 62/676,025, filed on May 24, 2018.

(51) Int. Cl.
*A61K 31/444* (2006.01)
*A61K 31/551* (2006.01)
*A61P 35/02* (2006.01)

(52) U.S. Cl.
CPC .......... *A61K 31/444* (2013.01); *A61K 31/551* (2013.01); *A61P 35/02* (2018.01)

(58) Field of Classification Search
CPC ...... A61K 31/444; A61K 31/551; A61P 35/02
See application file for complete search history.

(56) References Cited

U.S. PATENT DOCUMENTS

| | | | |
|---|---|---|---|
| 9,221,764 B2 * | 12/2015 | Bushweller .......... | C07D 401/14 |
| 9,926,290 B2 | 3/2018 | Bushweller et al. | |
| 2016/0096820 A1 * | 4/2016 | Bushweller .......... | C07D 401/04 |
| | | | 514/394 |

FOREIGN PATENT DOCUMENTS

| | | |
|---|---|---|
| WO | 2016/011402 A1 | 1/2016 |
| WO | 2016/014859 A1 | 1/2016 |
| WO | 2018/022855 A1 | 2/2018 |

OTHER PUBLICATIONS

Herrmann et al. Oncotarget, 2012, vol. 3, pp. 1588-1599 (Year: 2012).*
Coude et al. Oncotarget, 2015, vol. 6, pp. 17698-17712 (Year: 2015).*
International Search Report and Written Opinion in International Application No. PCT/US2019/033889, dated Oct. 29, 2019.
Pulikkan et al. "CBFBeta-SMMHC Inhibition Disrupts Enhancer Chromatin Dynamics and Represses MYC Transcriptional Program in Inv(16) Leukemia," Blood, Dec. 7, 2017, vol. 130, Suppl. 1, p. 784-784.
Tanaka et al. "Design and Characterization of Bivalent BET Inhibitors," Nature Chemical Biology, Oct. 24, 2016, vol. 12, Iss. 12. pp. 1089-1096.
Illendula et al. "Small Molecule Inhibitor of CBFBeta-RUNX Binding for RUNX Transcription Factor Driven Cancers," EBioMedicine, Apr. 28, 2016, vol. 8, pp. 117-131.
Pulikkan et al. "CBFBeta-SMMHC Inhibition Triggers Apoptosis by Disrupting MYC Chromatin Dynamics in Acute Myeloid Leukemia," Cell, Jun. 28, 2018, vol. 174, pp. 172-186.
Illendula et al. "A small-molecule inhibitor of the aberrant transcription factor CBFβ-SMMHC delays leukemia in mice," Science, Feb. 13, 2015, vol. 347, pp. 779-784.

* cited by examiner

*Primary Examiner* — James D. Anderson
(74) *Attorney, Agent, or Firm* — RAPHAEL BELLUM PLLC

(57) ABSTRACT

This invention relates to methods and compositions for treatment of inv (16) leukemia and particularly to treatment of acute myeloid leukemia. Disclosed is a method of treating inv (16) leukemia comprising the step of administering to a subject in in need thereof a therapeutically effective combination of a) a compound of the formula (1) (1) and b) a BRD4 inhibitor selected from the group consisting of JQ1, CeMMECZ, 1-BET 151 (or GSK1210151A), 1-BET 762 (or GSK525762), PFI-1, bromosporine, OTX-015 (or MK-8628), TEN-010, CPI-203, CPI-0610, RVX-208, BI2536, TG101348, LY294002, ABBV-075 (or mivebresib), FT-1101, ZEN003694, pharmaceutically acceptable salts and mixtures thereof. The therapeutically effective combination synergistically inhibits proliferation of inv (16) leukemia cells. This invention also relates to pharmaceutical compositions comprising a therapeutically effective combination of the compound of formula (1) and the BRD4 inhibitor and a pharmaceutically acceptable excipient.

5 Claims, 34 Drawing Sheets

Specification includes a Sequence Listing.

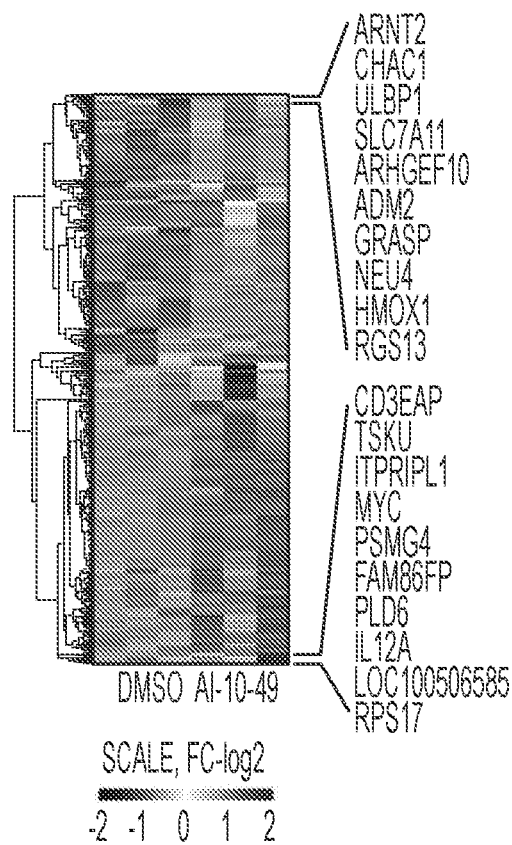
FIG. 1A
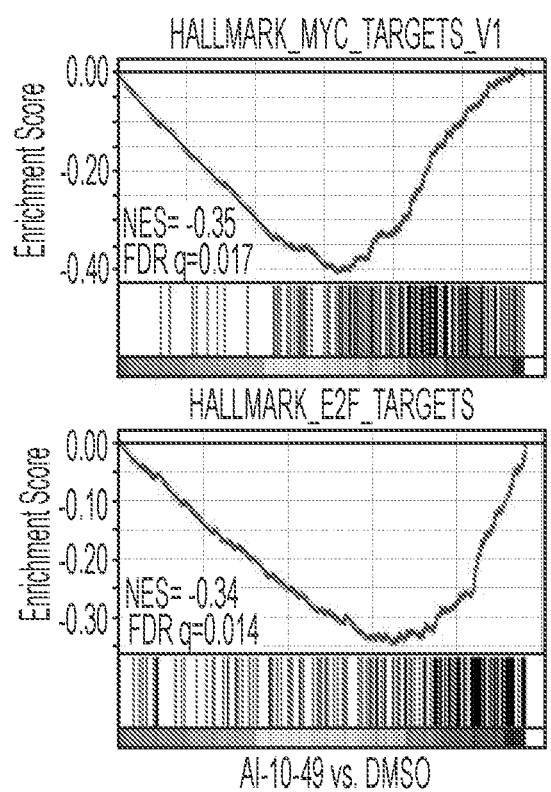
FIG. 1B
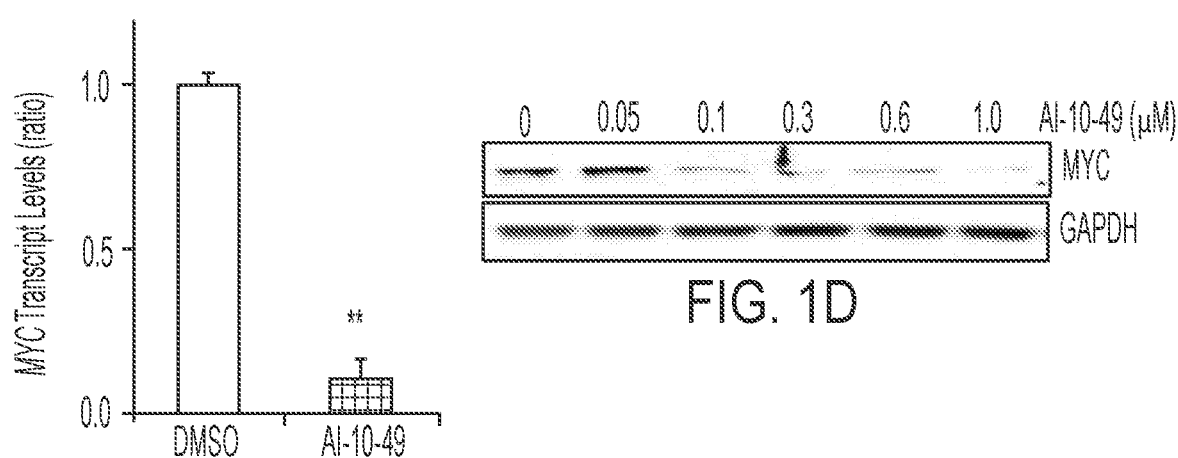
FIG. 1C
FIG. 1D

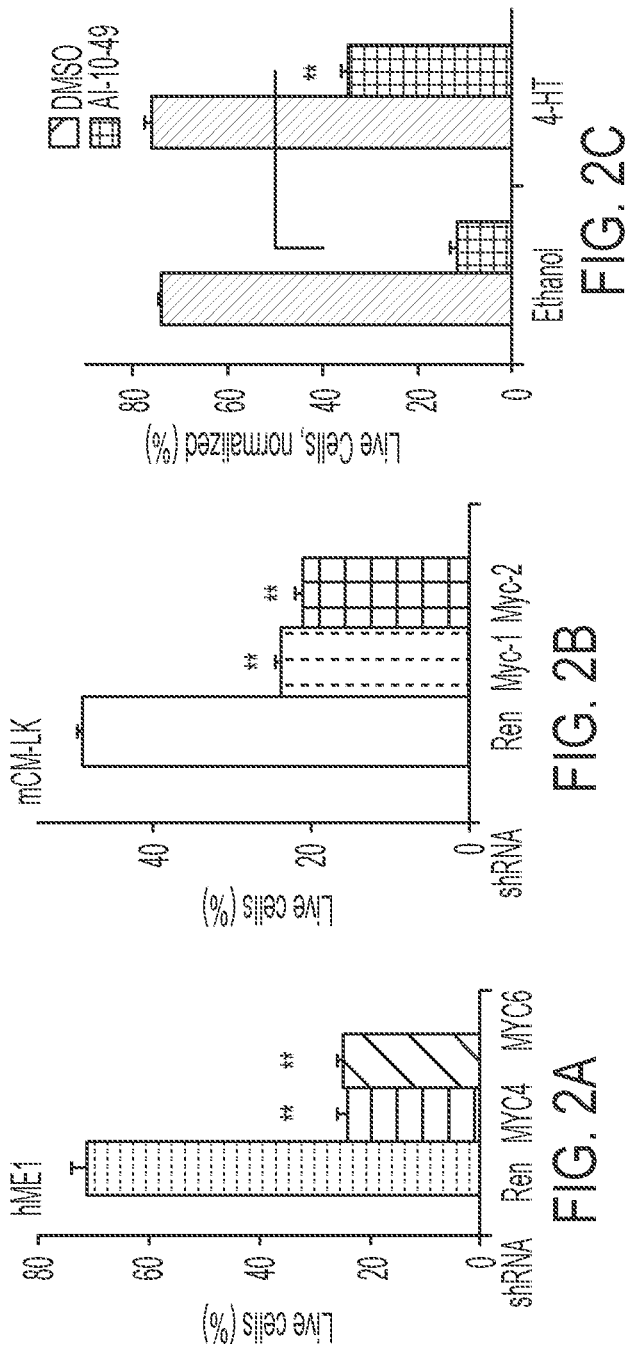

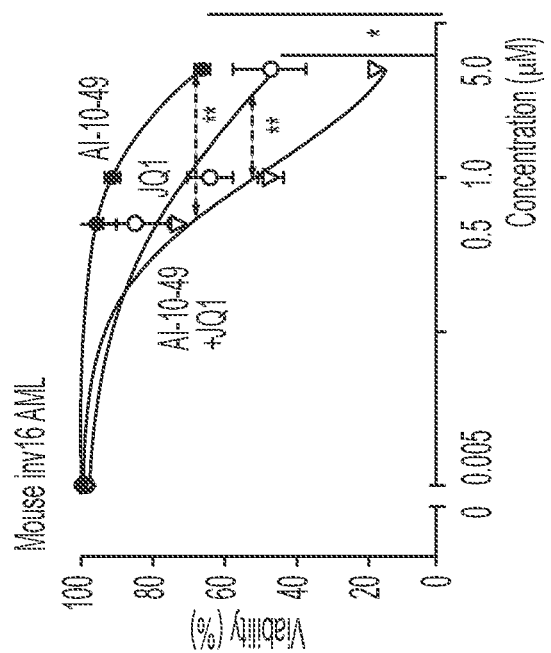
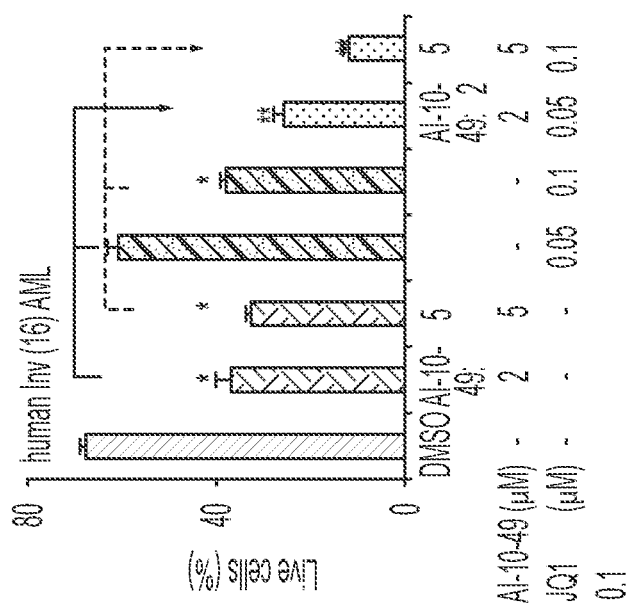
FIG. 3E
FIG. 3D

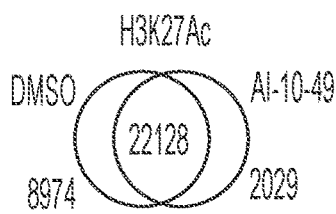
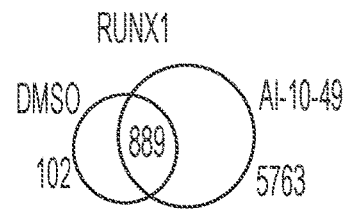
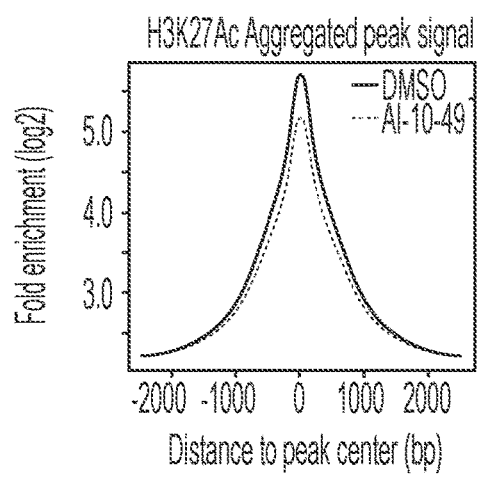
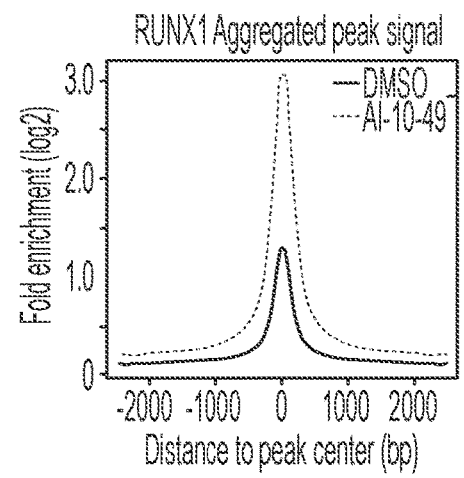
FIG. 4A
FIG. 4B
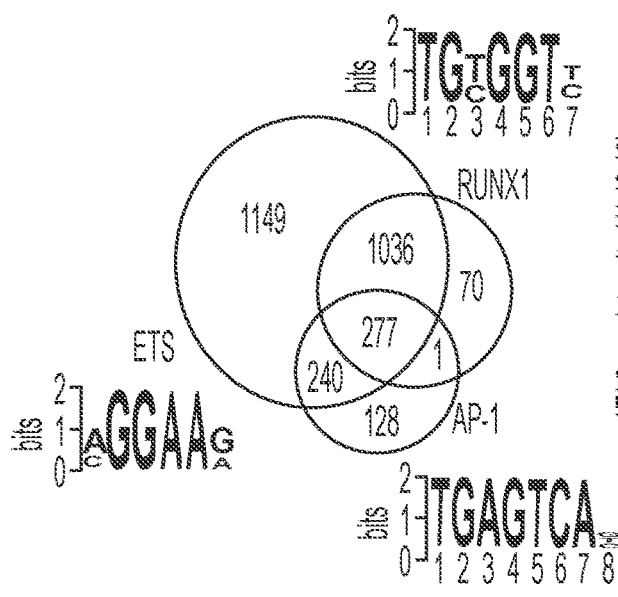
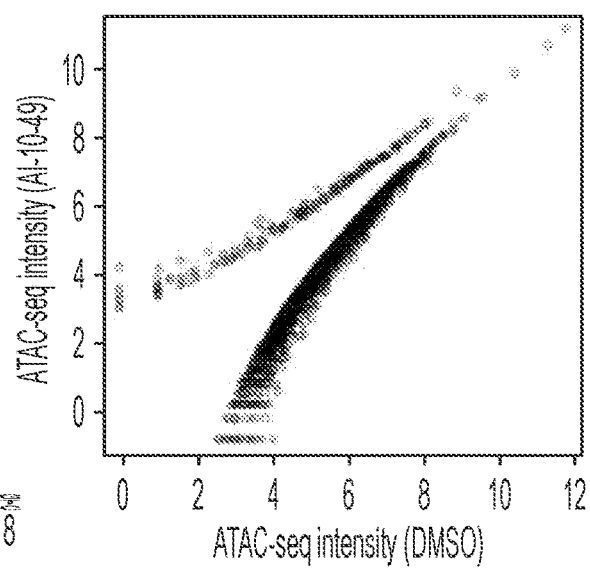
FIG. 4C
FIG. 4D

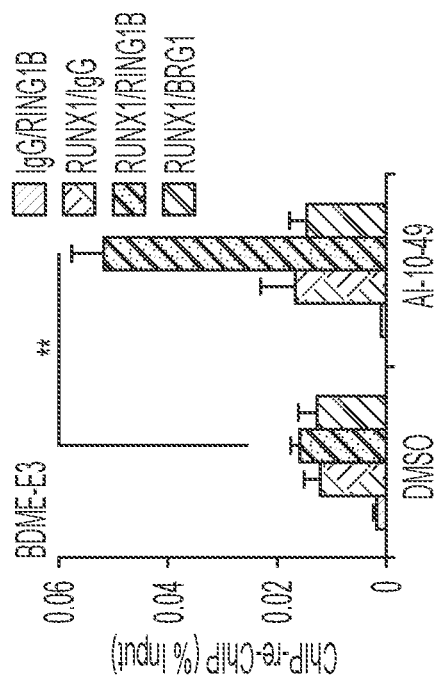
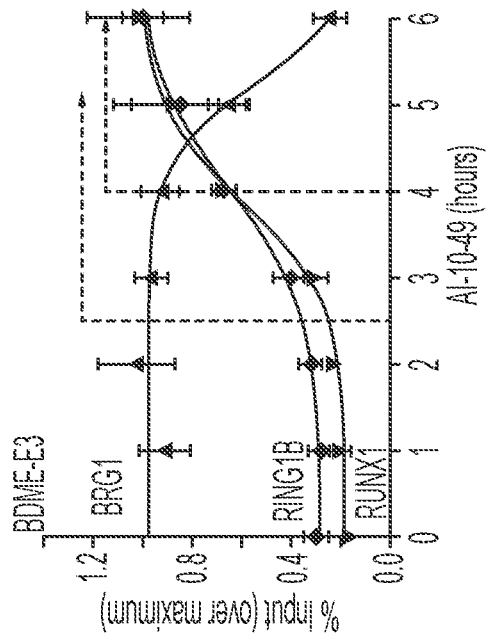
FIG. 7H
FIG. 7G

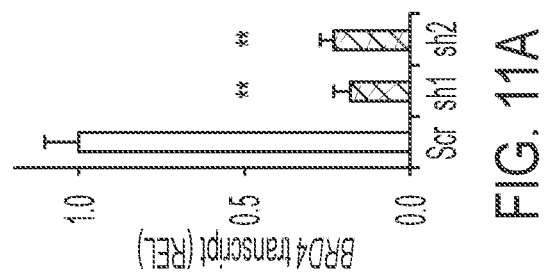
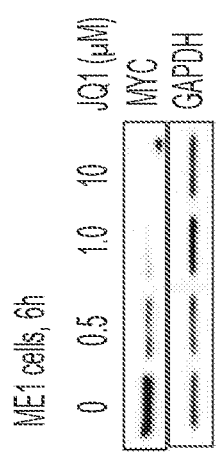
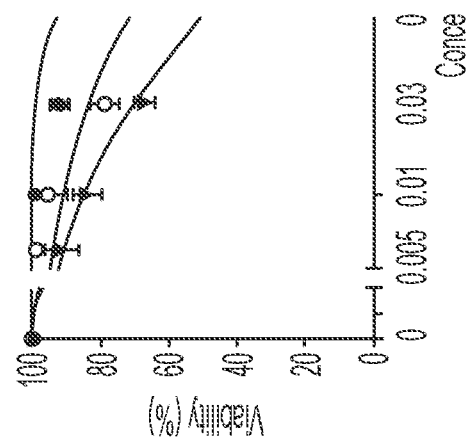
FIG. 11A
FIG. 11B
FIG. 11C

SEQUENCE LISTING

```
<160> NUMBER OF SEQ ID NOS: 40

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
tgtggagggc agctgttc                                                       18

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
aacagagtaa gagagccgca                                                     20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
```

```
ctcaagaggc ccctttagc                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tgcacctccc acacatacag                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agtgctgttt cctttgctgg                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
actctgatga ctgccacaaa g                                                 21

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
aggagcccac cttctcattt                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
acattgcaag agtggctgtg                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
aggaagtggc tttcacatgc                                                   20

<210> SEQ ID NO 10
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 10
gcgtgcaaaa gagagaaacc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ctttctagtg ggggttgcag                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ctgttctgaa agatccagcc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ttccagagac ctctgccagt                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
agagtcgggt gttgatttgg                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
cagggaccga tctgatgaaa g                                            21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
cccagggaat ggttgatatt c                                            21
```

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ccacagttca ctacactcac                                               20

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
cccagctgcc ttagtttaac c                                             21

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
gcagctgctt agacgctgga tttt                                          24

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
gcagcagctc gaatttcttc caga                                          24

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
agaaaatctg gcaccacacc                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
agaggcgtac agggatagca                                               20

<210> SEQ ID NO 23
<211> LENGTH: 22
<212> TYPE: DNA
<213> ORGANISM: Artificial Sequence
<220> FEATURE:
<223> OTHER INFORMATION: Synthetic

```
<400> SEQUENCE: 23
ctgtttgaag gctggatttc ct                                              22

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
cagcaccgac agacgcc                                                    17

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cgaggcccag agcaagagag                                                 20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
cggttggcct tagggttcag                                                 20

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
caccgaaatg tacaggaggg ctgac                                           25

<210> SEQ ID NO 28
<211> LENGTH: 25
<212> TYPE: DNA
<213> ORGANISM: Artificial Sequence
<220> FEATURE:
<223> OTHER INFORMATION: Synthetic

<400> SEQUENCE: 28
aaacgtcagc cctcctgtac atttc                                           25

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
caccggtctc aaacctctgt ttcc                                            24

<210> SEQ ID NO 30
```

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
aaacggaaac agaggtttga gacc                                           24

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
caccgccctg agaaagtgct attta                                          25

<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32
aaactaaata gcactttctc agggc                                          25

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
caccgaagtc cagactgcaa taag                                           24

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
aaaccttatt gcagtctgga cttc                                           24

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
caccgagaag gagagctagt ggat                                           24

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36

```
aaacatccac tagctctcct tctc                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
caccgaggaa acttgttttt ccgt                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
aaacacggaa aaacaagttt cctc                                          24

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
taatacgact cactatagcc                                               20

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
tccctttagt gagggttaat a                                             21
```

COMBINATION THERAPIES FOR TREATING CANCER

CROSS-REFERENCE TO RELATED APPLICATIONS

This application claims priority to U.S. Application No. 62/676,025, filed May 24, 2018, which is incorporated herein by reference in its entirety.

STATEMENT REGARDING FEDERALLY SPONSORED RESEARCH OR DEVELOPMENT

This invention was made with government support under NIH grants R01 CA204979 and R01 CA140398. The government has certain rights in the invention.

FIELD OF THE INVENTION

The invention generally relates to compositions and methods to treat leukemia. More particularly, the invention relates to compositions and methods of treatment using a synergistic combination of specific transcription factor inhibitors and inhibitors targeting chromatin activity.

BACKGROUND

Cancer cells adapt to mutations that alter the function of transcription factors and chromatin-associated factors to survive. In leukemia, these factors often drive leukemia initiation and maintenance. The transcription factor complex core-binding factor (CBF) is a hetero-dimeric factor composed of a stabilizing subunit CBFβ and the DNA-binding subunit RUNX (encoded by three genes: RUNX1, RUNX2 and RUNX3). In hematopoiesis, RUNX1 is expressed in all lineages, and only repressed during erythropoiesis (Lorsbach et al., 2004; North et al., 2004). RUNX1/CBFβ regulates pathways associated with proliferation, survival and differentiation (Blyth et al., 2005). The genes encoding CBFβ and RUNX1 are frequent targets of mutations in hematologic malignancies. The chromosome inversion inv (16)(p13; q22), found in 8% of acute myeloid leukemia (AML) cases, fuses the CBFβ and MYH11 genes to produce the leukemic oncoprotein CBFβ-SMMHC (Liu et al., 1993). This fusion protein out-competes wildtype CBFβ in vitro because it has significantly higher affinity and altered stoichiometry for RUNX1 relative to the native CBFβ (Cao et al., 1997; Kanno et al., 1998; Lukasik et al., 2002). During development, CBFβ-SMMHC expression blocks definitive hematopoiesis and embryos die at mid-gestation (Castilla et al., 1996), a similar phenotype to that of Runx1- and Cbfb-knock out embryos (Wang et al., 1996a; Wang et al., 1996b). These findings imply that CBFβ-SMMHC has a dominant negative effect on CBF function.

In adult hematopoiesis, allelic CBFβ-SMMHC expression alters hematopoietic stem cell (HSC) differentiation, with a clonal expansion of the short-term HSCs and multi-potential progenitors (Kuo et al., 2006). These progenitors trigger an expansion of pre-leukemic myeloid progenitors and a marked reduction of lymphoid differentiation (Kuo et al., 2008; Kuo et al., 2006; Xue et al., 2014; Zhao et al., 2007). The myeloid pre-leukemic progenitors are leukemia precursors, which acquire cooperating mutations to induce myeloid leukemia in mice (Castilla et al., 1999; Xue et al., 2014).

RUNX1 associates with chromatin-modifying proteins, including histone deacetylases (Durst and Hiebert, 2004; Guo and Friedman, 2011), acetyltransferases (Kitabayashi et al., 2001; Kitabayashi et al., 1998) and methyltransferases (Reed-Inderbitzin et al., 2006; Vu et al., 2013; Zhao et al., 2008) in hematopoiesis. These interactions regulate RUNX1 affinity to DNA and its transcriptional activity, and modulate its association with activating and repressing chromatin complexes (Lichtinger et al., 2010). However, the role of RUNX1 in establishing chromatin-associated complexes that maintain the survival of AML cells and how they modulate leukemia maintenance remain poorly understood.

The SWItch/Sucrose Non-Fermentable (SWI/SNF) protein complex remodels histone-DNA interactions and is associated with active regulatory regions of the genome, including promoters and enhancers. Components of this multiprotein complex are mutated in cancer (Kadoch and Crabtree, 2015). In AML, chromatin-associated complexes, including SWI/SNF and BET family of bromodomain ("BRD")-proteins, promote enhancer activity to mediate the survival of the leukemia-initiating cells (Blobel et al., 2011; Zuber et al., 2011). Conversely, the accumulation of polycomb-repressive complexes (PRC1 and PRC2) is associated with repressed chromatin results in tri-methylation of lysine-27 in histone H3 (H3K27me3), thereby promoting local compaction of the chromatin structure around the enhancers and silencing expression of target genes (Di Croce and Helin, 2013). The homeostasis of hematopoiesis critically depends on PRC function as these proteins regulate self-renewal and differentiation of HSCs (Lessard and Sauvageau, 2003; van der Lugt et al., 1994), as well as inhibit differentiation and proliferation of myeloid progenitor cells in mice (Cao et al., 2016).

The protooncogene MYC regulates the balance between self-renewal and differentiation of HSCs (Wilson et al., 2004), and is essential for lymphoid (de Alboran et al., 2001; Douglas et al., 2001) and megakaryocytic/erythroid development (Guo et al., 2009). MYC expression, however, needs to be downregulated during myeloid differentiation, since MYC repression promotes granulopoiesis while ectopic expression blocks granulopoiesis (Gowda et al., 1986; Holt et al., 1988; Johansen et al., 2001). Emerging evidence indicates that the epigenetic regulation of enhancer activity plays a critical role in myeloid differentiation and leukemia. The SWI/SNF and BRD4 complexes regulate MYC expression from the distal super-enhancer BDME (BRD4-dependent MYC enhancer), 1.7 megabases (Mb) downstream from its transcription start site (TSS, (Shi et al., 2013; Yashiro-Ohtani et al., 2014)), and is composed of five enhancer elements, each occupied by a number of myeloid transcription factors. In leukemia, MYC is expressed at high levels, and regulates expression of its normal high-affinity targets and a new set of targets in a tumor type-specific manner (Kress et al., 2015). The SWI/SNF ATPase subunit BRG1 (Brahma related gene 1), required for normal granulopoiesis, associates with BDME to maintain MYC levels in mixed-lineage AML cells (Shi et al., 2013; Vradii et al., 2005). In addition, BDME function seems to be critical for leukemia maintenance in GSI-resistant T-cell acute lymphoblastic leukemia (Yashiro-Ohtani et al., 2014).

The mechanisms underlying oncogenic CBFβ-SMMHC function and the role of epigenetic complexes in the maintenance of inv(16) AML need further investigation. A bivalent inhibitor, AI-10-49, that disrupts CBFβ-SMMHC binding to RUNX1, and specifically induces apoptosis of inv(16) AML cells was previously developed (Illendula et al., 2015). Transcriptome analysis of AI-10-49 treated inv(16) AML cells revealed that MYC expression and function are drastically repressed. As described below, pharmacologic analysis reveals that AI-10-49 and the BRD4 inhibitor JQ1 synergize to induce apoptosis of inv(16) AML cells in vitro and in vivo. Genomic analysis of RUNX1 binding and epigenetic marks, utilizing chromatin immunoprecipitation coupled with deep-sequencing (ChIP-seq) and ChIP-quantitative-PCR (ChIP-qPCR), determined that AI-10-49 induces increased RUNX1 association to three distal MYC enhancers, including the BDME-E3 and two new regions, called ME1 and ME2. This correlates with the depletion of BRG1 and active enhancer mark histone H3K4me1, concomitant with an increase in PRC1 component RING1B and the repressive mark histone H3K27me3 at these enhancers. It is also shown below that CBFβ-SMMHC activity maintains MYC levels and the survival of inv(16) AML cells, and that AI-10-49 triggers apoptosis by repressing MYC expression. Finally, carbon-copy chromosome conformation capture (5C) and CRISPR-Cas9 technology was used to physically and functionally implicate RUNX1-associated enhancers with MYC expression and cell viability. These studies, described herein, demonstrate that CBFβ-SMMHC promotes the survival of inv(16) AML by maintaining MYC levels from three distal enhancers, and that pharmacologic inhibition of the fusion protein induces apoptosis due to epigenetic repression of MYC expression. Furthermore, the results herein provide evidence for the enhanced efficacy of the combination of AI-10-49 and BRD4 inhibitors for the treatment of inv(16) AML.

There is a long felt need in the art for compositions and methods useful for preventing and for treating acute myeloid leukemia, particularly involving the inv(16) fusion. The present invention addresses these needs.

SUMMARY OF THE INVENTION

This invention generally relates to methods and compositions for treatment of inv (16) leukemia. In particular, this invention relates to a method of treating inv(16) leukemia comprising the step of:
administering to a subject in need thereof a therapeutically effective combination of
a) a compound of the formula (1)

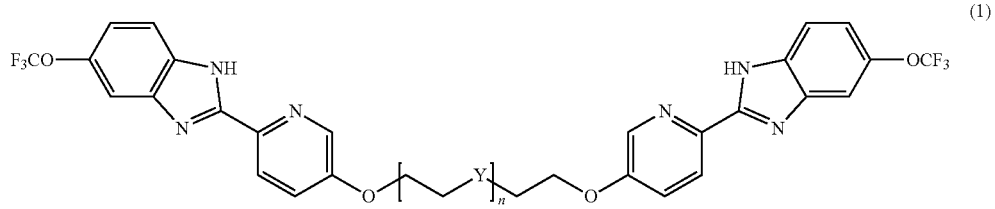

where Y is O, NH, or NR where R is methyl or ethyl,
where n is an integer of from 1 to 10,
or a pharmaceutically acceptable salt thereof; and
b) a BRD4 inhibitor selected from the group consisting of JQ1, CeMMEC2, I-BET 151 (or GSK1210151A), I-BET 762 (or GSK525762), PFI-1, bromosporine, OTX-015 (or MK-8628), TEN-010, CPI-203, CPI-0610, RVX-208, B12536, TG101348, LY294002, ABBV-075 (or mivebresib), FT-1101, ZEN003694, pharmaceutically acceptable salts and mixtures thereof. The therapeutically effective combination of the compound of formula (1) and the BRD4 inhibitor synergistically inhibits proliferation of inv(16) leukemia cells. In methods according to the invention, compounds of formula (1) and the BRD4 inhibitor are administered simultaneously, or sequentially.

The invention also relates to pharmaceutical compositions comprising a therapeutically effective combination of the compound of formula (1) and the BRD4 inhibitor and a pharmaceutically acceptable excipient. In some embodiments, the therapeutically effective combination of the compound of formula (1) and the BRD4 inhibitor is a combined amount synergistically effective to inhibit proliferation of inv(16) leukemia cells.

In preferred methods and pharmaceutical compositions of the invention, the compound of formula (1) is a compound of formula (1a) or a pharmaceutically acceptable salt thereof,

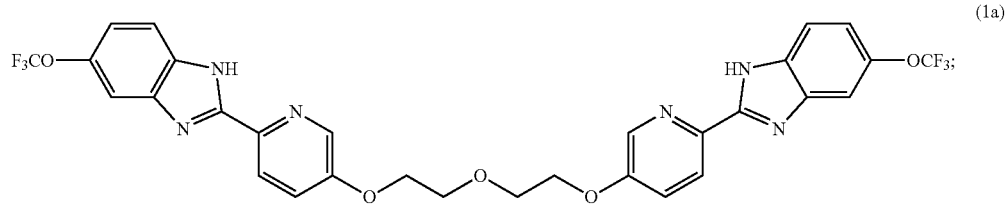 [SMILES: FC(F)(F)Oc1ccc2[nH]c(-c3ccc(OCCOCCOc4ccc(-c5nc6cc(OC(F)(F)F)ccc6[nH]5)nc4)cn3)nc2c1]

(1a)

and the BRD4 inhibitor is JQ1 or a pharmaceutically acceptable salt thereof

BRIEF DESCRIPTION OF THE DRAWINGS

FIG. 4 (A-D) shows that global modification of RUNX1 association to chromatin in inv(16) AML cells. (A, B) show Venn diagram (top) and peak distribution from peak center (bottom) representing the overlap of H3K27ac (A) and RUNX1 (B) peaks in ME-1 cells treated with DMSO (black) or 1 μM AI-10-49 (red) treatment for 6 hrs. (C) is a motif analysis of RUNX1 associated peaks genome wide in AI-10-49 treated ME-1 cells. (D) is a scattered plot representing open chromatin peaks by ATAC-seq analysis in DMSO and AI-10-49 treated ME-1 cells.

DESCRIPTION OF THE INVENTION

Figures 1E, 1F:
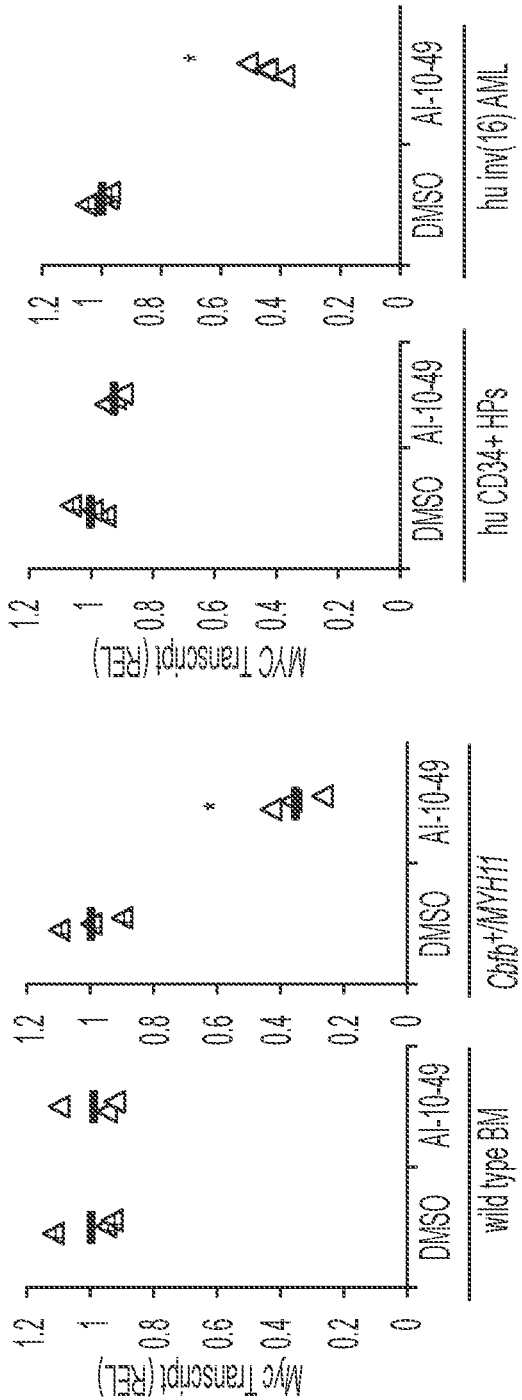
FIG. 1 (A-F) shows that AI-10-49 inhibits MYC transcriptional program in inv(16) AML cells. (A) shows a heat map representation of differentially expressed genes in RNA-seq analysis between DMSO and AI-10-49 (1 μM) treated ME-1 cells for 6 hrs from three independent experiments. A total of 591 genes (in red) are positively correlated with AI-10-49 and 696 genes (in blue) are negatively correlated (>2 fold change, FDR<0.01). Top up- and down-regulated genes are shown. (B) shows gene set enrichment analysis showing biological processes and signaling pathways that are correlated with AI-10-49-treatment in ME-1 cells. (FDR) false discovery rate; (NES) normalized enrichment score. (C) shows that AI-10-49 inhibits MYC transcript levels in ME-1 cells. Cells were treated with 1 uM AI-10-49 for 6 hrs and conducted Real Time RT-PCR for MYC. Results from triplicate experiments shown; error bars represent the SD. (D) shows that AI-10-49 inhibits MYC protein levels in ME-1 cells. Cells were treated with AI-10-49 for 6 hrs and western blotting for whole cell lysates. (E, F) MYC transcriptional levels in wild type lineage negative mouse bone marrow cells (E, left) and lineage negative mouse Cbfb$^{+/MYH11}$ leukemic cells (E, right), and human cord blood CD34+ cells (F, left) and human primary inv(16) leukemic CD34+ cells (F, right). Mouse and human cells were treated with 5 μM AI-10-49 for 24 hrs. Each symbol represents the average for an individual sample from triplicate treatments. For panels C, E and F, significance was calculated as unpaired t-test, *P<0.05, or **P<0.005. See also FIG. S1.

The invention relates to methods of treatment of inv(16) leukemia comprising administering to a subject in need thereof a therapeutically effective combination of:
a) a compound of formula (1)

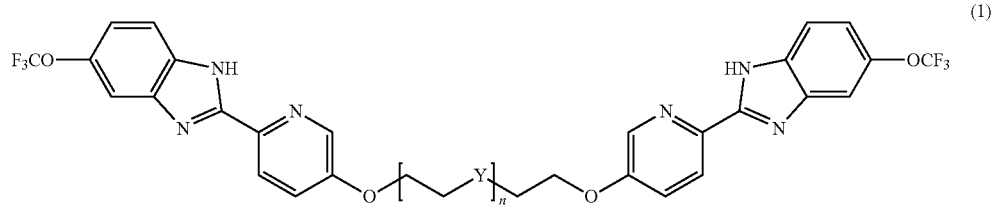

(1)

where Y is O, NH, or NR where R is methyl or ethyl,
where n is an integer of from 1 to 10,
or a pharmaceutically acceptable salt thereof; and
b) a BRD4 inhibitor selected from the group consisting of JQ1, CeMMEC2, I-BET 151 (or GSK1210151A), I-BET 762 (or GSK525762), PFI-1, bromosporine, OTX-015 (or MK-8628), TEN-010, CPI-203, CPI-0610, RVX-208, B12536, TG101348, LY294002, ABBV-075 (or mivebresib), FT-1101, ZEN003694, pharmaceutically acceptable salts, and mixtures, thereof.

Mutations that alter transcription factor function play critical roles in leukemogenesis. The fusion oncoprotein CBFβ-SMMHC, expressed in leukemia cases with chromosome 16 inversion, drives leukemia development and maintenance by altering the activity the transcription factor RUNX1. Cell viability is maintained by neutralizing RUNX1 repression of MYC expression via a CBFβ-SMMHC-mediated mechanism. Upon pharmacologic inhibition of the CBFβ-SMMHC/RUNX1 interaction, RUNX1 increases its association with three MYC distal downstream enhancers and represses MYC expression. Concomitantly, SWI/SNF activation complex component, BRG1, and H3K4me1 marks at these sites are replaced by polycomb-repression complex component, RING1B, and H3K27me3 marks. CBFβ-SMMHC inhibition cooperates with the BET-inhibitor JQ1 to eliminate leukemia cells and delay leukemia latency in mice. Analysis of enhancer interaction reveals that the three MYC enhancers are physically connected with the MYC promoter, and genome-editing analysis demonstrated that all three are functionally implicated in the regulation of MYC expression and in cell viability. Studies in the examples below reveal a mechanism whereby CBFβ-SMMHC drives leukemia maintenance and provides support for efficacious in inv(16) leukemia therapy with inhibitors targeting chromatin activity.

The therapeutically effective combination of the compound of formula (1) and the BRD4 inhibitor synergistically inhibits proliferation of inv(16) leukemia cells. Methods of the invention are particularly useful in the treatment of acute myeloid leukemia, one type of inv(16) leukemia. "Treatment" or "treating" includes prophylaxis of the specific disorder or condition, or alleviation of the symptoms associated with a specific disorder or condition and/or preventing or eliminating those symptoms.

Direct inhibition of the oncogenic CBFβ-SMMHC fusion protein has been shown as a potentially effective therapeutic approach for inv(16) AML. (Illendula, et al., 2015.) 5-methoxy-2-(pyridin-2-yl)-1H-benzo[d]imidazole, AI-4-57, was reported as a compound which binds to the CBFβ portion of the CBFβ-SMMHC fusion protein and inhibits its binding to the Runt domain of RUNX proteins (Illendula, et al., 2015.) The trifluoromethoxy (CF3O) derivative, 2-(pyridin-2-yl)-5-(trifluoromethoxy)-1H-benzo[d]imidazole, A-10-47 displayed enhanced metabolic stability relative to the methoxy compound. (Illendula, et al., 2015.) Polyethylene glycol-based linkers were used to create bivalent derivatives with 5-, 7-, 10-, and 16-atom linker lengths. (Illendula, et al., 2015.) The five-atom linker compound had less activity, but the longer linker compounds show potent inhibition. A compound with a seven-atom linker, AI-4-83, displayed a 63-fold enhancement over the monovalent compound. In addition, AI-4-83 achieved >10-fold dissociation of CBFβ-SMMHC and RUNX1 Runt domain at saturating concentrations. (Illendula, et al., 2015.)

The trifluoromethoxy derivative with a seven-atom linker, AI-10-49, also referred to herein as compound (1a),

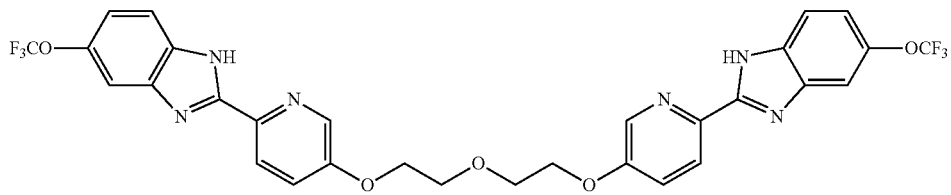 [SMILES: FC(F)(F)Oc1ccc2[nH]c(-c3ccc(OCCOCCOc4ccc(-c5nc6cc(OC(F)(F)F)ccc6[nH]5)nc4)cn3)nc2c1]

10 was shown to be a potent and CBFβ-SMMHC specific compound that induced cell death in the ME-1 cell line, a leukemia cell line with inv(16). (Illendula, et al., 2015.) CBFβ-SMMHC is oligomeric, whereas CBFβ is monomeric. AI-10-49 inhibits CBFβ-SMMHC activity while having a minimal effect on CBFβ function. (Illendula, et al., 2015.)

In methods according to the invention, compounds of formula (1) contain two 2-(pyridin-2-yl)-5-(trifluoromethoxy)-1H-benzo[d]imidazole groups, attached by a linker, —O—[CH2CH2Y]n-O—. In compounds of formula (1), the linker connects the two binding portions of the molecule. Dimeric or bivalent inhibitors take advantage of the oligomeric nature of CBFβ-SMMHC and apply the principles of poly-valency (Mammen, et al., 1998; Kiessling, et al., 2006) to achieve the desired selectivity. The truncated forms of CBFβ-SMMHC lacking the extreme C-terminus have been shown to form dimers in solution. (Lukasik, et al., 2002.) For the full-length protein, these dimers then oligomerize to form high order oligomers. (Shigesada, et al. 2004.) In contrast, CBFβ is monomeric in solution. This difference in oligomerization provides a means to achieve selective inhibition of CBFβ-SMMHC versus CBFβ.

According to methods of the invention, in compounds of formula (1), Y is O, NH, or S. In a method of the invention, Y is O. In another method of the invention, Y is N—CH3. When n is greater than 1, Y can be the same or different.

According to methods of the invention, in compounds of formula (1), n is an integer from 1 to 10. In methods and compositions according to the invention, n is 1, 2, 3, 4, 5, 6, 7, 8, 9, or 10. Preferably, n is from 1 to 5. In compounds of formula (1), the linker should be long enough to allow the bivalent compound of formula (1) to achieve binding enhancement by means of CBFβ-SMMHC-ligand interaction versus a mono-valent CBFβ-ligand interaction. See U.S. Pat. No. 9,221,764, FIG. 5. The dissociation constant for a monovalent compound binding to monomeric CBFβ is equal to $K_d$(monomer). A homo-dimer of this compound will bind the monomeric CBFβ protein with a dissociation constant equal to Kd(monomer)/2. However, this same homo-dimer will interact with two sites on the dimeric CBFβ-SMMHC protein and have a $K_d$(dimer) equal to $(K_d(monomer))^2/C_{eff}$ where $C_{eff}$ is the effective concentration resulting from the tethering of the two binding sites on CBFβ-SMMHC to one another. (Mulder, et al., 2004)

Non-limiting exemplary compounds within formula (1), include:

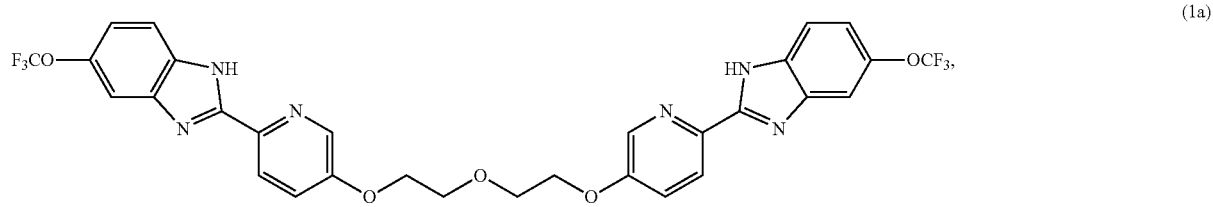

(1a)

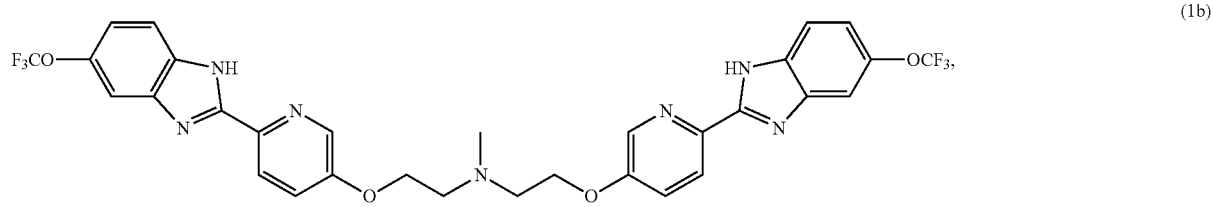

(1b)

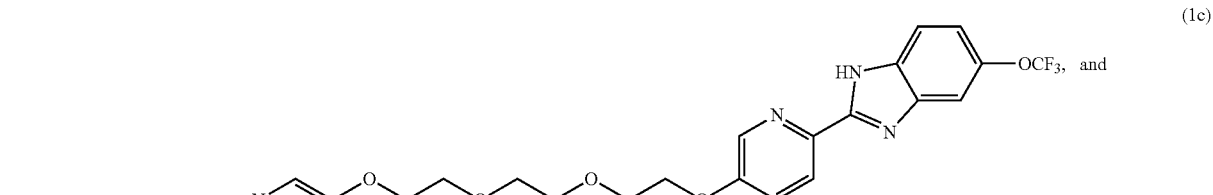

(1c), and

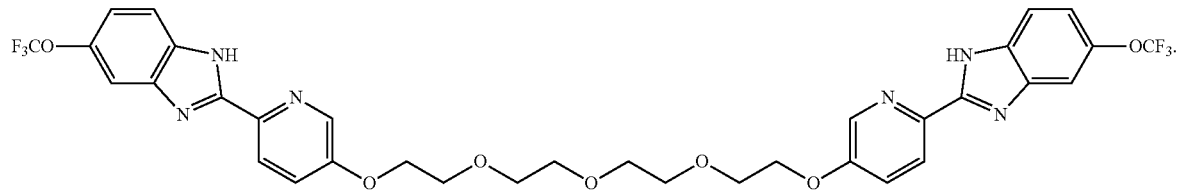

(1d)

In a preferred method according to the invention, the compound of formula (1) is

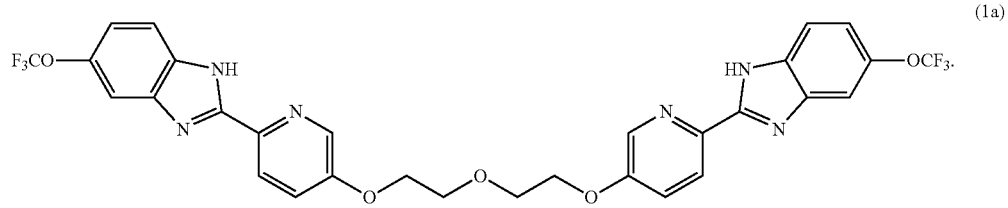

(1a)

U.S. Pat. No. 9,221,764, incorporated herein by reference, discloses structures and synthetic routes of specific bivalent inhibitors with polyethylene glycol-based linkers.

In another method according to the invention, the compound of formula (1) is

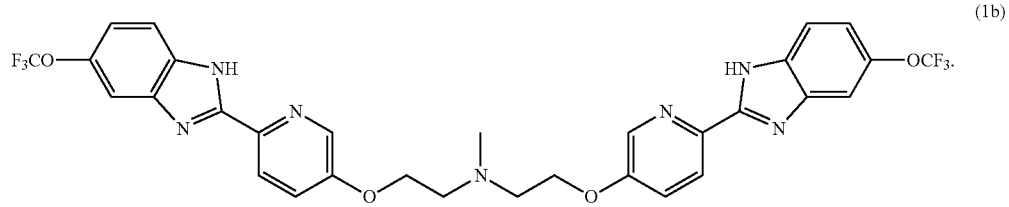

(1b)

The BRD4 inhibitor is selected from, for example, JQ1, CeMMEC2, I-BET 151 (or GSK1210151A), I-BET 762 (or GSK525762), PFI-1, bromosporine, OTX-015 (or MK-8628), TEN-010, CPI-203, CPI-0610, RVX-208, B12536, TG101348, LY294002, ABBV-075 (or mivebresib), FT-1101, ZEN003694, or a pharmaceutically acceptable salt thereof. These compounds are commercially available and/or their synthesis is described in the literature. The BRD4 inhibitor may also be any one of the compounds disclosed in WO 2012/174487, WO 2014/076146, US 2014/0135336, WO 2014/134583, WO 2014/191894, WO 2014/191896, US 2014/0349990, WO 2014/191906, or WO 2018/087401, or in the reference article Alqahtani et al., 2019, each of which are hereby incorporated by reference in their entirety. Several BRD4 inhibitors are under clinical investigation. (See, e.g., Alqahtani et al., 2019, Table 2). In some methods of the invention, the BRD4 inhibitor is JQ1. In preferred methods of the invention, the BRD4 inhibitor is ABBV-075 or OTX015.

As mentioned, a compound of formula (1) or a BRD4 inhibitor used in the invention may take the form of a "pharmaceutically acceptable salt", which refers to salts that retain the biological effectiveness and properties of the compounds of the invention and that are not biologically or otherwise undesirable. In many cases, the compounds administered in the methods of the invention form acid and/or base salts by virtue of the presence of amino and/or carboxyl groups or groups similar thereto. Pharmaceutically acceptable acid addition salts may be prepared from inorganic and organic acids. Salts derived from inorganic acids include, but are not limited to, hydrochloric acid, hydrobromic acid, sulfuric acid, nitric acid, phosphoric acid, and the like. Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

In a method according to the invention, a therapeutically effective combination of an amount of a compound of formula (1), such as compound (1a), and a BRD4 inhibitor, such as JQ1, is administered to synergistically inhibit proliferation of inv(16) leukemia cells. The term "inhibit" refers to the ability of a compound of the invention to reduce or impede a described function, such as cell proliferation. Preferably, inhibition is by at least 10%, more preferably by at least 25%, even more preferably by at least 50%, and most preferably, the function is inhibited by at least 75%.

Although a BRD4 inhibitor and a compound of formula (1) have been shown, separately, to be effective at inhibiting proliferation of inv(16) leukemia cells, when combined, the result is more than additive, it is, surprisingly, synergistic. See e.g., FIGS. 3 and 11. The amount of the synergistic combination of a compound of formula (1) and of BRD4 inhibitor or a salt thereof, required for use in a method of treatment according to the invention may vary with the route of administration, the nature of the condition being treated and the age and condition of the patient and will be ultimately at the discretion of the attendant physician or clinician. The duration of administration of the compound of formula (1) may be determined by one of skill in the art, and continued as needed. The synergistic combination used in the invention has a weight to weight ratio of the daily administered dose of BRD4 inhibitor to the daily administered dose of compounds of formula (1) ranging from about 0.0001:1 to about 1000:1. The ratio may be from about 0.001:1 to about 100:1, e.g., from about 0.01:1 to about 10:1, e.g. from about 0.1:1 to about 1:1. Daily administration may be simultaneous, continuous or discontinuous.

In methods of treatment according to the invention the compound of formula (1) and the BRD4 inhibitor are administered simultaneously, or sequentially by first administering the compound of formula (1) followed by administering the BRD4 inhibitor. In a method of treatment according to the invention, the compound of formula (1) and the BRD4 inhibitor may also be administered simultaneously. In an alternative method according to the invention, the compound of formula (1) and the BRD4 inhibitor may be administered sequentially by first administering the compound of formula (1) followed by administering the BRD4 inhibitor. Alternatively, the BRD4 inhibitor is administered, and then the compound of formula (1) is administered. As another example of a method of treatment of the invention, the compound of formula (1) and the BRD4 inhibitor are administered simultaneously, followed by daily administration of the compound of formula (1) for 1 or more days.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple injections.

In methods according to the invention, the extent of proliferation of cells from a subject suffering from inv(16) leukemia is measured using techniques known to those skilled in the art. A specific population of cells referred to as leukemia initiating cells using mouse models of inv(16) leukemia has been identified and accepted as an appropriate animal model. (Kuo, Y. H., et al., 2006.) This population of cells retains the inv(16) but does not possess the secondary mutations associated with disease. Upon acquisition of such secondary mutations, these cells can progress to overt leukemia. These cells are also typically more resistant to traditional cytotoxic chemotherapy and therefore represent a pool of cells from which relapse can occur. Cells may be extracted for measurement from blood, spleen, bone marrow, and/or spinal fluid. For example, populations of Lin-Sca-Kit+ cells extracted from a subject with inv(16) leukemia are measured using flow cytometry. The Lin-Sca1-c-Kit+ cell population, is enriched in the leukemia initiating cell (LIC) and leukemia stem cell (LSC) population.

In some embodiments, the compound of formula (1) and the BRD4 inhibitor are administered in a pharmaceutical composition comprising the compound of formula (1), the BRD4 inhibitor, and a pharmaceutically acceptable carrier. In other methods of treatment according to the invention, the compound of formula (1) is administered in a pharmaceutical composition comprising the compound of formula (1) and a pharmaceutically acceptable carrier, and the BRD4 inhibitor is subsequently administered in a pharmaceutical composition comprising the BRD4 inhibitor and a pharmaceutically acceptable carrier. In some methods according to the invention, the dosage formulations of the pharmaceutical can be the same or different. For example, both the BRD4 inhibitor and the compound of formula (1) are formulated as solutions for parenteral delivery. Alternatively, the BRD4 inhibitor is formulated as a solution, and the compound of formula (1) is formulated as a tablet.

A separate embodiment of the invention is a pharmaceutical composition comprising a pharmaceutically-acceptable carrier and a therapeutically effective combination of
a) a compound of the formula (1)

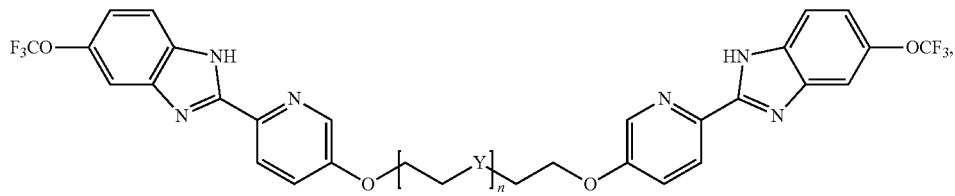

(1)

where Y is O, NH, or NR where R is methyl or ethyl,
n is an integer of from 1 to 10,
or a pharmaceutically acceptable salt thereof; and
b) a BRD4 inhibitor selected from the group consisting of JQ1, CeMMEC2, I-BET 151 (or GSK1210151A), I-BET 762 (or GSK525762), PFI-1, bromosporine, OTX-015 (or MK-8628), TEN-010, CPI-203, CPI-0610, RVX-208, B12536, TG101348, LY294002, ABBV-075 (or mivebresib), FT-1101, ZEN003694, or a pharmaceutically acceptable salt thereof;
wherein the compound of formula (1) and the BRD4 inhibitor are present in a combined amount synergistically effective to inhibit growth of inv(16) leukemia cells.

A pharmaceutical composition according to the invention may be in any pharmaceutical form which contains a synergistic combination of a compound of formula (1) and the BRD4 inhibitor. The pharmaceutical composition may be, for example, a tablet, a capsule, a liquid suspension, an injectable composition, a topical composition, an inhalable composition or a transdermal composition. Liquid pharmaceutical compositions may also be prepared. The pharmaceutical compositions generally contain, for example, about 0.1% to about 99.9% by weight of a combined amount of a compound of formula (1) and the BRD4 inhibitor, for example, about 0.5% to about 99% by weight of a combined amount of a compound of formula (1) and the BRD4 inhibitor and, for example, 99.5% to 0.5% by weight of at least one suitable pharmaceutical excipient. In one embodiment, the composition may be between about 5% and about 75% by weight of a combined amount of a compound of formula (1) and the BRD4 inhibitor with the rest being at least one suitable pharmaceutical excipient or at least one other adjuvant, as discussed below.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used.

Suitable liquid pharmaceutical compositions contain solubilizing agents that improve drug aqueous solubility, such as, for example, cyclodextrins. One non-limiting example of a cyclodextrin is a polyanionic variably substituted sulfobutyl ether of β-cyclodextrin ((3-CD) (Captisol®).

For a solid pharmaceutical composition of the invention, the carrier in a solid pharmaceutical composition should not substantially alter either the compound of formula (1) or the BRD4 inhibitor. Nor should the carrier be otherwise incompatible with the compound of formula (1) or the BRD4 inhibitor used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. Suitable solid dosage forms of the pharmaceutical composition of the invention include at least one pharmaceutically acceptable excipient such as, for example, sodium citrate or dicalcium phosphate or (a) (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suitable suspensions may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Dosage forms for oral administration, which includes capsules, tablets, pills, powders, granules, and suspensions may be used. Suitable pharmaceutical compositions according to the invention may also be formulated as liquid or injectable pharmaceutical compositions. Administration may be carried out via any of the accepted modes of administration or agents for serving similar utilities. Thus, administration may be, for example, orally, buccally, or parenterally (intravenous, intramuscular, intraperitoneal, or subcutaneous), in the form of solid, semi-solid, lyophilized powder, or liquid dosage forms, such as, for example, tablets, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

Generally, in pharmaceutical compositions according to the invention, the combined concentration of the compound of formula (1) and the BRD4 inhibitor of the invention in a liquid composition, such as an injectable solution, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

EXAMPLES

EXPERIMENTAL MODEL AND SUBJECT DETAILS. The following resources, materials and methods were utilized in the Examples described herein.

TABLE 1

| Key Resources | | |
|---|---|---|
| REAGENT or RESOURCE | SOURCE | IDENTIFIER |
| Antibodies | | |
| CD117 APC | BD Biosciences | 553356 |
| Ly-6A/E APC-Cy7 | BD Biosciences | 560654 |

TABLE 1-continued

| Key Resources | | |
|---|---|---|
| REAGENT or RESOURCE | SOURCE | IDENTIFIER |
| CD34 FITC | BD Biosciences | 553733 |
| CD16/CD32 PE-Cy | eBiosciences | 25-0161 |
| Ly-6G and Ly-6C Biotin | BD Biosciences | 553124 |
| Cd11b Biotin | BD Biosciences | 553309 |
| CD45R/B220 Biotin | BD Biosciences | 553086 |
| CD3e Biotin | eBiosciences | 13-0037-82 |
| Ter119 Biotin | BD Biosciences | 553672 |
| Streptavidin eFluor ® 450 | eBiosciences | 48-4317-82 |
| CD11b PE | BD Biosciences | 555388 |
| CD15 APC | BD Biosciences | 561716 |
| RUNX1 polyclonal | Abcam | ab23980 |
| H3K27ac polyclonal | Abcam | ab4729 |
| H3K4me1 polyclonal | Abcam | ab8895 |
| H3k27me3 monoclonal | Abcam | ab6002 |
| BRG1 monoclonal | EPITOMICS | 2822-1 |
| RING1B polyclonal | Abcam | ab3832 |
| c-MYC polyclonal | Santa Cruz | N-262 |
| GAPDH monoclonal | Cell Signaling | 3683 |
| Biological Samples | | |
| human AML samples | UPENN | www.upenn.edu |
| human AML samples | Univ. of Halle | www.uni-halle.de |
| human cord blood | UMASS | https://www.umassmemorial.org |
| Chemicals, Peptides, and Recombinant Proteins | | |
| AI-10-49 | John Bushweller | www.virginia.edu |
| JQ1 | ApexBio | A1910 |
| plpC | GE healthcare | 27-4732-01 |
| 4-Hydroxytamoxifen | Sigma | H7904 |
| Recombinant Human IL-3 | Peprotech | 200-03 |
| Recombinant Human IL-6 | Peprotech | 200-06 |
| Recombinant Human flt3 | Peprotech | 300-19 |
| Recombinant Human SCF | Peprotech | 300-07 |
| Recombinant Human TPO | Peprotech | 300-18 |
| Recombinant Murine IL-3 | Peprotech | 213-13 |
| Recombinant Murine IL-6 | Peprotech | 216-16 |
| Recombinant Murine SCF | Peprotech | 250-03 |
| Critical Commercial Assays | | |
| PureLink ® RNA Mini Kit | Life Technologies | 12183018A |
| SUPERSCRIPT III | Invitrogen | 18080-044 |
| Power SYBR ® Green PCR Master Mix | Applied Biosystems | 4367659 |
| Annexin V Apoptosis Detection Kit | BD Biosciences | 559763 |
| Subcellular Protein Fractionation Kit | Thermo Fischer Scientific | 78840 |
| CellTiter 96 AQ$_{ueous}$ One Solution Cell Proliferation Assay | Promega | G3580 |
| True seq Nano DNA LT kit | Illumina | 15041757 |
| Nextera DNA Sample Preparation Kit | Illumina | FC-121-1030 |
| KAPA Genotyping kit | Kapabiosystems | KK7352 |
| TruSeq RNA library kit | Illumina | RS-122-2001 |
| CD34 MicroBead Kit | Milteny Biotec | 130-046-702 |
| EasySep ® Mouse Hematopoietic Progenitor Cell Enrichment Kit | Stemcell Technologies | 19756 |
| Amaxa ® Cell Line Nucleofector ® Kit V | Lonza | VCA-1003 |
| Deposited Data | | |
| RNA-seq | NCBI, GEO | TBA |
| ChIP-seq | NCBI, GEO | TBA |
| ATAC-seq | NCBI | TBA |
| 5C | NCBI | TBA |
| Experimental Models: Cell Lines | | |
| ME-1 cells | DSMZ | ACC 537 |
| Experimental Models: Organisms/Strains | | |
| C57BL/6J | Taconic Biosciences | https://www.taconic.com |
| Oligonucleotides | | |
| ChIP-MYC-PR For | IDT | TGTGGAGGGCAGCTGTTC (SEQ ID NO: 1) |
| ChIP-MYC-PR Rev | IDT | AACAGAGTAAGAGAGCCGCA (SEQ ID NO: 2) |
| ChIP-MYC-ME1 For | IDT | CTCAAGAGGCCCCTTTTAGC (SEQ ID NO: 3) |
| ChIP-MYC-ME1 Rev | IDT | TGCACCTCCCACACATACAG (SEQ ID NO: 4) |
| ChIP-MYC-ME2 For | IDT | AGTGCTGTTTCCTTTGCTGG (SEQ ID NO: 5) |

TABLE 1-continued

Key Resources

| REAGENT or RESOURCE | SOURCE | IDENTIFIER |
|---|---|---|
| ChIP-MYC-ME2 Rev | IDT | ACTCTGATGACTGCCACAAAG (SEQ ID NO: 6) |
| ChIP-MYC-E1 For | IDT | AGGAGCCCACCTTCTCATTT (SEQ ID NO: 7) |
| ChIP-MYC-E1 Rev | IDT | ACATTGCAAGAGTGGCTGTG (SEQ ID NO: 8) |
| ChIP-MYC-E2 For | IDT | AGGAAGTGGCTTTCACATGC (SEQ ID NO: 9) |
| ChIP-MYC-E2 Rev | IDT | GCGTGCAAAAGAGAGAAACC (SEQ ID NO: 10) |
| ChIP-MYC-E3 For | IDT | CTTTCTAGTGGGGGTTGCAG (SEQ ID NO: 11) |
| ChIP-MYC-E3 Rev | IDT | CTGTTCTGAAAGATCCAGCC (SEQ ID NO: 12) |
| ChIP-MYC-E4 For | IDT | TTCCAGAGACCTCTGCCAGT (SEQ ID NO: 13) |
| ChIP-MYC-E4 Rev | IDT | AGAGTCGGGTGTTGATTTGG (SEQ ID NO: 14) |
| ChIP-MYC-E5 For | IDT | CAGGGACCGATCTGATGAAAG (SEQ ID NO: 15) |
| ChIP-MYC-E5 Rev | IDT | CCCAGGGAATGGTTGATATTC (SEQ ID NO: 16) |
| ChIP-MYC-N-Me For | IDT | CCA CAG TTC ACT ACA CTC AC (SEQ ID NO: 17) |
| ChIP-MYC-N-Me For | IDT | CCCAGCTGCCTTAGTTTAACC (SEQ ID NO: 18) |
| MYC For | IDT | GCAGCTGCTTAGACGCTGGATTTT (SEQ ID NO: 19) |
| MYC Rev | IDT | GCAGCAGCTCGAATTTCTTCCAGA (SEQ ID NO: 20) |
| ACTB For | IDT | AGAAAATCTGGCACCACACC (SEQ ID NO: 21) |
| ACTB Rev | IDT | AGAGGCGTACAGGGATAGCA (SEQ ID NO: 22) |
| Myc-For | IDT | CTGTTTGAAGGCTGGATTTCCT (SEQ ID NO: 23) |
| Myc-Rev | IDT | CAGCACCGACAGACGCC (SEQ ID NO: 24) |
| Actb For | IDT | CGAGGCCCAGAGCAAGAGAG (SEQ ID NO: 25) |
| Actb Rev | IDT | CGGTTGGCCTTAGGGTTCAG (SEQ ID NO: 26) |
| CRISPR ME1 sg1 For | IDT | CACCGAAATGTACAGGAGGGCTGAC (SEQ ID NO: 27) |
| CRISPR ME1 sg1 Rev | IDT | AAACGTCAGCCCTCCTGTACATTTC (SEQ ID NO: 28) |
| CRISPR ME1 sg3 For | IDT | CACCGGTCTCAAACCTCTGTTTCC (SEQ ID NO: 29) |
| CRISPR ME1 sg3 Rev | IDT | AAACGGAAACAGAGGTTTGAGACC (SEQ ID NO: 30) |
| CRISPR ME2 sg1 For | IDT | CACCGCCCTGAGAAAGTGCTATTTA (SEQ ID NO: 31) |
| CRISPR ME2 sg1 Rev | IDT | AAACTAAATAGCACTTTCTCAGGGC (SEQ ID NO: 32) |
| CRISPR ME2 sg4 For | IDT | CACCGAAGTCCAGACTGCAATAAG (SEQ ID NO: 33) |
| CRISPR ME2 sg4 Rev | IDT | AAACCTTATTGCAGTCTGGACTTC (SEQ ID NO: 34) |
| CRISPR ME3 sg1 For | IDT | CACCGAGAAGGAGAGCTAGTGGAT (SEQ ID NO: 35) |
| CRISPR ME3 sg1 Rev | IDT | AAACATCCACTAGCTCTCCTTCTC (SEQ ID NO: 36) |
| CRISPR ME3 sg7 For | IDT | CACCGAGGAAACTTGTTTTTCCGT (SEQ ID NO: 37) |
| CRISPR ME3 sg7 Rev | IDT | AAACACGGAAAAACAAGTTTCCTC (SEQ ID NO: 38) |

Recombinant DNA

| | | |
|---|---|---|
| MYC shRNA4 | UMMS RNAi Core Facility | TRCN0000174055 |
| MYC shRNA6 | UMMS RNAi Core Facility | TRCN0000010390 |
| psPAX2 | Addgene | 12260 |
| pMD2.G | Addgene | 12259 |
| pLentiCRISPRv2 | Addgene | 52961 |
| pDecko-mCherry | Addgene | 78534 |
| MYC-ER | Addgene | 19128 |
| pGEM-T | Addgene | A3600 |

Software and Algorithms

| | | |
|---|---|---|
| R v3.4.0 | R core team, 2016 | https://www.r-project.org |
| Bioconductor v3.4 | (Huber et al., 2015) | http://www.bioconductor.org |
| ChIPseqAnno v3.9 | (Zhu, 2013; Zhu et al., 2010) | https://bioconductor.org/packages/release/bioc/html/ChIPpeakAnno.html |
| ATACseqQC v1.0.3 | Bioconductor package | https://bioconductor.org/packages/release/bioc/html/ATACseqQC.html |
| Bowtie2 v2.1.0 | (Langmead and Salzberg, 2012) | http://bowtie-bio.sourceforge.net/bowtie2/index.shtml |
| MACS2 v2.1.0 | (Zhang et al., 2008) | https://github.com/taoliu/MACS |
| FastQC v0.10.1 | Babraham Bioinformatics | https://www.bioinformatics.babraham.ac.uk/projects/fastqc/ |
| Tophat v2.0.9 | (Kim et al., 2013) | https://ccb.jhu.edu/software/tophat/index.shtml |
| Cufflinks v2.2.0 | (Trapnell et al., 2010) | http://cole-trapnell-lab.github.io/cufflinks/ |

TABLE 1-continued

Key Resources

| REAGENT or RESOURCE | SOURCE | IDENTIFIER |
|---|---|---|
| Diffbind v2.4.8 | (Ross-Innes et al., 2012) | https://bioconductor.org/packages/release/bioc/html/DiffBind.html |
| Picard tools 1.96 | MIT Broad Institute | https://broadinstitute.github.io/picard/ |
| Bedtools v1.25.0 | | http://bedtools.readthedocs.io/en/latest/ |
| Fastx-toolkit v.0.0.18 | | |
| Cutadapt | (Martin, 2011) | https://cutadapt.readthedocs.io |
| GSEA | Broad Institute | http://software.broadinstitute.org/gsea/index.jsp |
| Molecular Signatures Database v6.0 | Broad Institute | http://software.broadinstitute.org/gsea/msigdb/index.jsp |
| GraphPad Prism 6.0 | GraphPad | https://www.graphpad.com |
| FlowJo Software | FlowJo LLC | https://www.flowjo.com |
| Other | | |
| RPMI 1640 Medium | Thermo Fischer | A10491-01 |
| Fetal Bovine Serum, Charcoal Stripped | Sigma | F6765 |
| StemSpan SFEM II | STEMCELL Technologies | 09605 |
| StemSpan SFEM | STEMCELL Technologies | 09650 |
| RBC Lysis Solution | 5 Prime | 2301310 |
| MethoCult | STEMCELL Technologies | M3534 |
| Effectene | Qiagen | 301425 |
| Fugene 6 Transfection Reagent | Promega | E2691 |
| Dyna beads | Life technologies | 10004D |
| Agencourt AMPure XP 5 mL Kit | Beckman Coulter | A63880 |
| Plasmocin | Invivogen | ant-mpt |
| Retro-X Concentrator | Clontech | 631455 |
| Lenti-X Concentrator | Clontech | 631231 |
| Accell medium | Thermo Scientific | B-005000-500 |
| Halt ™ Protease Inhibitor Cocktail | Thermo Scientific | 778429 |
| Proteinase K (Fungal) | Invitrogen | 25530-031 |
| T4 polynucleotide kinase | NEB | M0201 |
| Q5 ® High-Fidelity DNA Polymerase | NEB | M0491L |
| HindIII | NEB | R0104S |
| Dounce homogenizer, pestle A | Kimble Chase | 885301-0002 |
| Amicon ® Ultra—0.5 ml-30K | Millipore | UFC5030BK |
| T4 DNA ligase | Invitrogen | 15224 |
| 5X T4 DNA ligase | Invitrogen | P/N y90001 |
| Taq DNA ligase and buffer | NEB | M0208S |
| Salmon testes DNA | Sigma | D7656 |
| QIAquick gel extraction kit | Qiagen | 28704 |

Mice. All animal experiments were performed in accordance with a protocol reviewed and approved by the University of Massachusetts Institutional Animal Care and Use Committee. Mice carrying knock in Cbfb$^{+/MYH11}$ and Nras$^{+/G12D}$ oncogenic alleles has previously described (Xue et al., 2014) and maintained at the animal facility at University of Massachusetts Medical School with all protocols approved by the University of Massachusetts Medical School Animal Care Committee (Certificate A1266). C57BL/6J mice for transplantation and toxicology experiments were obtained from Taconic Biosciences (Germantown, Md., U.S.A.).

Cell Lines. ME-1 cells (DSMZ) were cultured in RPMI 1640 with 20% fetal bovine serum, 25 mM HEPES, 100 U/ml Penicillin and 100 mg/ml Streptomycin (Life Technologies) and 1 µl/ml Plasmocin (Invitrogen). 293T cells (DSMZ) were cultured in DMEM with 10% fetal bovine serum, 100 U/ml Penicillin and 100 mg/ml Streptomycin (Life Technologies) and 1 µl/ml Plasmocin (Invitrogen).

Primary Hematopoietic Cell Cultures. Human cord blood samples were collected from the UMASS Memorial Medical Center, and CD34$^+$ cells were isolated using the CD34 Microbead kit (Miltenyi Biotec). The use of the cord blood samples for research purposes was approved by the Ethics Committee of the University of Massachusetts Medical School. Human AML samples were received from Martin Peter Carroll (University of Pennsylvania) and Carsten Mueller-Tidow (University of Heidelberg, Germany). Hematopoietic CD34$^+$ cells were isolated from human AML bone marrow samples using the CD34 Microbead kit (Miltenyi Biotec). All patients gave written consent for use of their samples. Human cord blood CD34+ cells as well as human primary leukemic cells were cultured in StemSpan SFEM II (Stemcell Technologies), 100 U/ml Penicillin and 100 mg/ml Streptomycin (Life Technologies) supplemented with 10 ng/mL human recombinant TPO, 10 ng/mL human recombinant FLT3L (10 ng/mL), 100 ng/mL human recombinant SCF, 10 ng/mL human recombinant IL3, and 20 ng/mL human recombinant IL-6.

Murine bone marrow cells were isolated by crushing femur and tibia of the hind legs of mice. Wild type mouse bone marrow cells were cultured in StemSpan Serum-Free Expansion Medium (SFEM, Stemcell Technologies), 100 U/ml Penicillin and 100 mg/ml Streptomycin (Life Technologies) supplemented with 6 ng/ml murine recombinant IL3, 10 ng/ml murine recombinant IL6, and 50 ng/ml murine recombinant SCF. Cbfb$^{+/MYH11}$ and Nras$^{+/G12D}$ leukemic bone marrow and spleen cells were cultured in StemSpan Serum-Free Expansion Medium (SFEM, Stemcell Technologies), 100 U/ml Penicillin and 100 mg/ml Streptomycin (Life Technologies) supplemented with 10 ng/ml murine recombinant IL3, and 50 ng/ml murine recombinant SCF.

Method Details

Generation of shRNA constructs. Lentiviral plasmids were received from UMMS RNAi Core Facility. The puromycin resistance cassette in pLKO plasmids was replaced by green fluorescent protein (GFP) using standard cloning techniques.

Retroviral Production and Transduction. For studying Myc silencing in inv(16) leukemic cells, 293T packaging cells were transfected with 8 µg retroviral constructs co-expressing GFP (c-Myc (shMyc) or *Renilla* luciferase (shRen); (Roderick et al., 2014)) and 4 µg-Ecopac packaging plasmid with Fugene transfection reagent. Retroviral supernatants were collected at 40 and 64 hrs, pooled and concentrated using Retro-X Concentrator (Clonetech), following the manufacturer's instructions. Leukemic spleen cells from conditional Cbfb$^{+/MYH11}$ and Nras$^{+/G120}$ knock in mice were lineage depleted using EasySep® Mouse Hematopoietic Progenitor Cell Enrichment Kit (Stem cell technologies, following the manufacturer's instructions. 1-2×10$^6$ lineage-negative cells were transduced twice by spin infection with shRNA retroviruses with a time gap of 24 hrs. Cells expressing GFP+ were sorted 24 hrs after second infection. Cbfb+/56M/Cre or Cbfb+/56M conditional knock-in mice were treated with polyinosinic-polycytidylic acid (pIpC). Bone marrow lineage negative cells from both groups of mice were spin-infected twice with retrovirus supernatants.

Lentiviral Production and Transduction. 293T packaging cells were transfected with 6 µg lentiviral constructs co-expressing GFP [pLKO scramble or pLKO MYC shRNAs), 6 ug packaging Plasmid psPAX2 (Addgene plasmid #12260) and 3 ug envelope plasmid pMD2.G (Addgene plasmid #12259) with Fugene transfection reagent. Lentiviral supernatants were collected at 40 and 64 hrs, pooled and concentrated using Lenti-X Concentrator (Clonetech), following the manufacturer's instructions. 2-3×10$^6$ ME-1 cells were transduced twice by spin infection with retroviruses with a time gap of 24 hrs. Cells expressing GFP were sorted 24 hrs after second infection.

CRISPR/Cas9-mediated deletion of the enhancer regions. The sgRNAs specific for 5' to the region of interest were cloned in pLentiCRISPRv2 (Addgene #52961). sgRNAs corresponding to 3' to the region of interest were cloned in pDecko-mCherry (Addgene #78534). The puromycin resistance cassette in pLentiCRISPRv2 was replaced by green fluorescent protein (GFP) using standard cloning techniques. All sgRNA cloning was done in respective plasmids using standard guide RNA cloning method. Briefly, top and bottom strand guide RNA oligos were phosphorylated using T4 Polynucleotide Kinase (NEB), annealed and inserted into the vectors at BsmB1 site. Guide RNAs cloned inside the pLentiCRISPRv2GFP were transfected into 293T cells using the FuGENE® 6 method according to the manufacturer's instructions. 48 hrs after transfection, genomic DNA was isolated, and PCR was carried out to amplify the region of interest. PCR product was re-annealed and treated with T7 endonuclease (NEB) according to the manufacturer's instruction. The reaction was later resolved on 2% agarose gel and product was analyzed. Oligonucleotide names and sequences (5'-3') are listed in the key resource table. 2-3×10$^6$ ME-1 cells were nucleofected with CRISPR/Cas9 plasmids (2 µg each) using Nucleofector™ Technology (Lonza) with the program X-01 and Amaxa® Cell Line Nucleofector® Kit V. Samples were sorted by flow cytometry 24 hrs later. Cells were cultured overnight, and dead cells were eliminated by dead cell removal kit (Miltenyi Biotec).

Mi-Seq Analysis. To identify deletion pattern with CRISPR/Cas9 plasmids, sorted cells were collected after 48 hrs of incubation and genomic DNA was isolated. A first round of PCR was carried out to amplify the genomic region of interest, using suitable primers, and products were gel purified. A second round of PCR was carried out using the primers to introduce a portion of the Illumina adaptor sequences, and the products were gel purified. A third round of PCR was carried out to introduce the sample indices and resulting products (100-200 bp) were gel purified, combined in a library and sequenced by Illumina Mi-Seq (150 bp-paired end).

Cell Viability Assay. Cell viability was estimated using the MTT kit, CellTiter 96® AQueous One Solution (Promega, PA). 20,000 cells/well were seeded in triplicate into 96-well plates. After 24-72 hrs, 20 µl of MTT reagent was added to wells containing cells or medium (blank), and absorption at 490 nm was measured using SpectraMax M5 plate reader (Molecular Devices).

Inducible expression of MYC using MYC-ER. 2×10$^6$ ME-1 cells were nucleofected with Nucleofector™ Technology (Lonza) with 6 µg of ScaI-linearized MYC-ER plasmid (Addgene #19128; (Ricci et al., 2004)) and plated on 6-well plate containing phenol red-free RPMI/10% with charcoal-treated fetal bovine serum. Selection with 3 µg/ml puromycin began 48 hrs after transfection and lasted 48 hrs followed by dead cells removal by dead cell removal kit (Miltenyi Biotec). MYC-ER was induced by treatment with 4-hydroxy-tamoxifen (4-HT) (Sigma-Aldrich) at a final concentration of 500 nM for 9 hrs.

Leukemia transplantation studies in mice. For testing efficacy of AI-10-49 and JQ1 in leukemia survival, 1×10$^3$ Cbfb$^{+/MYH11}$; Nras$^{+/G120}$ leukemic cells were transplanted into sub-lethally irradiated (650 rads), 6 to 8 week old wild type C57BL/6 female mice. Treatment with vehicle (DMSO), AI-10-49, JQ1 or both began at day 5 via intra peritoneal injection. AI-10-49 was administered at 200 mg/kg/day from day 5 to day 14. JQ1 was administered at 50 mg/kg/day from day 5 to day 25. Mice were sacrificed after visible characteristics of AML, including reduced motility and grooming activity, hunched back, and pale paws (anemia). Leukemic cells were extracted from spleen and analyzed at time of euthanasia as previously described (Kuo et al., 2006).

AI-10-49 and JQ1 Synergy Analysis. The IC50 was estimated using the drc package in R with lower bound set to 0 (Ritz et al., 2015). CIs were calculated using the formula a/A+b/B. Synergisms, additive effect and antagonism of combine treatment assays are defined as CI<1, CI=1 and CI>1 respectively, utilizing the Chou-Talalay Method (Chou, 2010).

Toxicology Studies. Six to eight week old wild type C57BL/6 female mice were treated with vehicle (DMSO), AI-10-49, JQ1 or both began via intra peritoneal injection. AI-10-49 was administered at 200 mg/kg/day for 10 days. JQ1 was administered at 50 mg/kg/day for 21 days. Mice were evaluated for signs of toxicity, including grooming, motility, and body weight. 24 hrs after last injection, peripheral blood cells were analyzed by flow cytometry. Mice were then euthanized for spleen and bone marrow analysis.

Flow Cytometry. For flow-cytometry, 2×10$^5$ cells were washed twice with 2% FBS in PBS and stained for 20-60 min at 4° C. in the dark and analyzed with a BD LSRII flow cytometer. Bone marrow hematopoietic stem and multilineage progenitors were analyzed as LSK+: Lin(−), kit(+), Sca1(+); common myeloid progenitors, CMP: Lin(−)Sca1(−)kit(+)CD34(+)CD16/32(−); granulocyte/monocyte progenitor, GMP: Lin(−)Sca1(−)kit(+)CD34(+)CD16/32(+); and megakaryocyte/erythroid progenitors, MEP: Lin(−)Sca1(−)kit(+)CD34(−)CD16/32(−). Flow cytometry analysis was performed using FlowJo Software.

Annexin V Assay. For detection of apoptotic cell death, the Annexin V Apoptosis Detection Kit I (BD Bioscience) was used as per manufacturer's instructions. Briefly, cells were centrifuged 2000 rpm for 10 min, resuspended in 100 µl 1× Annexin V binding buffer, added 5 µl Annexin-PE and 10 µl 7AAD and incubated for 15 min at room temperature in the dark followed by adding 500 µl 1× Annexin binding buffer. Cell viability was determined as the percent of 7-AAD negative/Annexin V negative cells with a BD LSRII flow cytometer.

Quantitative RT-PCR Analysis. mRNA was prepared with a PureLink® RNA Mini Kit (Life Technologies) and cDNA synthesis was performed with a SuperScript III kit (Life Technologies), per the manufacturers' instructions. Quantitative PCR analysis was conducted on an Applied Biosystems StepOnePlus System with Power SYBR® Green PCR Master Mix (Applied Biosystems). Expression levels were determined with the ΔCt method and normalized to (β Actin and/or GAPDH. Sequences of primers are provided in the Key Resource Table.

RNA Sequencing. The RNA for RNA-sequencing was prepared with a PureLink® RNA Mini Kit. RNA concentration was quantified with a NanoDrop spectrophotometer (Thermo Scientific). RNA integrity was evaluated with a 2100 Bioanalyzer with an RNA 6000 kit (Agilent Technologies). Libraries were prepared with a TruSeq RNA library preparation kit (Illumina). Libraries were quantified by qPCR, normalized and pooled before sequencing with paired-end 90-bp reads on an Illumina HiSeq2000 in triplicate.

RNA-seq data analysis. Raw reads from RNA-seq experiment were assessed for their quality using fastqc, followed by alignment to the reference human genome (hg19) using tophat v 2.0.9, bowtie2/2.1.0 (Trapnell et al., 2009) with the default setting except the following parameters: -b2-very-sensitive-mate-inner-dist 160-mate-std-dev 80-no-coverage-search-transcriptome-index=hg19_knownGene_transcriptome_data. Differential gene expression analysis was performed by cufflinks v 2.2.0 (Trapnell et al., 2012). Genes with a false discovery rate below 0.05 and a fold change greater than two were considered to be significantly differentially expressed and used for subsequent analysis.

Chromatin Immunoprecipitation (ChIP). ME-1 cells were treated with DMSO or AI-10-49 (1 µM) for six hrs. Cross-linking of proteins to DNA was accomplished by the addition of 1% formaldehyde for 10 min to cultured cells at room temperature. After neutralization with glycine, cells were lysed in lysis buffer with protease inhibitors and samples were sonicated to an average DNA length of 200-400 bp with a bioruptor (Diagenode). After sonication, the chromatin was immunoprecipitated with 10 µg of antibody of interest at 4° C. overnight. Antibody bound complexes were isolated with Dynabeads (Life Technologies). DNA was purified using phenol-chloroform isoamyl-alcohol method. Immunoprecipitated DNA was analyzed by sequencing (explained below) or qPCR on a StepOnePlus System (Applied Biosystems) with Power SYBR® Green PCR Master Mix and calculated as % of input. Sequences of primers are provided in Table 1.

For ChIP PCR in human primary AML sample with inv(16), CD34$^+$ cells were enriched using a CD34 Micro-Bead Kit (Miltenyi Biotec) and cultured overnight followed by dead cell removal by dead cell removal kit (Miltenyi Biotec). Cells were treated with DMSO/AI-10-49 (5 µM) for 8 hrs followed by the ChIP procedure mentioned above.

Chromatin immunoprecipitation followed by sequencing (ChIP-seq). DNA concentration was quantified with a Nano-Drop spectrophotometer (Thermo Scientific). DNA integrity was evaluated with a 2100 Bioanalyzer (Agilent Technologies). Libraries were prepared with in house ChIP-Seq Library preparation kit. Libraries were quantified by qPCR, normalized and pooled before sequencing with single-end 50-bp reads on an Illumina HiSeq4000).

ChIP-seq data analysis. ChIP-seq reads were aligned to the human genome (hg19) with Bowtie2 v 2.1.0 (Langmead and Salzberg, 2012) with the standard default settings. Only the reads with a mapping quality greater than 20 were kept, and the duplicated reads were removed using picard tools v 1.96 (https://broadinstitute.github.io/picard/). Peak calling was performed with MACS2 v 2.1.0 (Zhang et al., 2008) with default parameters. Input was used as a control for peak-calling. The narrowPeak files were generated by macs2 with a q-value threshold of 0.01, and the bigwig files were generated with the signal as fold enrichment by macs2 following the procedure at https://github.com/taoliu/MACS/wiki/Build-Signal-Track.

Assay for Transposase-Accessible Chromatin with sequencing (ATAC-seq). To profile for accessible chromatin regions, ATAC-seq was used as described elsewhere (Buenrostro et al., 2015), with the following modifications: ME-1 cells (50,000) were treated with DMSO or AI-10-49 (1 µM) for 6 hrs followed by washing once with 1×PBS by centrifugation using 5 min at 500×g and 4° C. with low acceleration and brake settings. Cell pellets were re-suspended in 50 µl of cold lysis buffer (10 mM Tris-HCl pH 7.4, 10 mM NaCl, 3 mM $MgCl_2$, 0.1% IGEPAL CA-630) and nuclei were pelleted by centrifugation for 10 min at 500×g, 4 C. Supernatant was discarded and nuclei were re-suspended in 25 µl reaction buffer containing 2.5 µl of Tn5 transposase and 12.5 µl of TD buffer (Nextera Sample preparation kit, Illumina). The reaction was incubated at 37° C. for 45 min. Immediately following transposition, tagmented DNA was purified using a Qiagen MiniElute PCR Purification Kit. For library amplification, two sequential PCRs were conducted with indexing primers included in the Nextera Index kit and NEBNext High-Fidelity 2×PCR Master Mix. After the first PCR, the libraries were enriched for fragments less than 600 bp by using Agencourt AM Pure XP 5 mL Kit (Beckman Coulter). A second PCR was conducted with the similar settings followed by size enrichment by Agencourt AM Pure XP 5 mL Kit. DNA was eluted and concentration was measured with a Qubit fluorometer (Life Technologies) and library quality evaluated using 2100 Bioanalyzer (Agilent Technologies). The libraries where sequences in 100 bp paired-end on an Illumina HiSeq2000.

ATAC-seq data analysis. The preprocessing of ATAC-seq data was followed as reported (Buenrostro et al., 2013). The adaptors were removed using cutadapt program v 1.3 (Martin, 2011). The reads were then mapped onto the human genome hg19 assembly using Bowtie2 (Langmead and Salzberg, 2012). The standard default settings were modified to allow mapped paired-end fragments up to 2 kb. Only the reads with mapping quality greater than 20 were kept, and the duplicated reads were removed using picard tools v 1.96 (https://broadinstitute.github.io/picard/), the reads from mitochondria were also removed. To visualize the mapped reads, the bigwig files were generated using deepTools2 (Ramirez et al., 2016). Quality assessment of ATAC-seq data was performed using ATACseqQC (Ou et al., 2017). Reads enrichment were called by MACS2 v 2.1.0 (Zhang et al., 2008) with default parameters using the reads with insert size less than 100 bp as nucleosome free regions.

Gene Set Enrichment Analysis (GSEA). GSEA (Subramanian et al., 2005) was used to determine the statistically significant molecular signatures with the AI-10-49 treatment. The input data for the GSEA were a complete table of genes ranked by the test_statistics from the cuffdiff results and a catalog of functional gene sets from Molecular Signature Database (Molecular Signatures Database v 6.0, www.broad.mit.edu/gsea/msigdb/msigdb_index.html). Default parameters were used. Gene sets with false discovery rate less than 0.25 were included.

Immunoblotting. ME-1 cells were lysed in modified RIPA buffer (50 mM Tris pH7.5, 150 mM NaCl, 1% NP40, 0.25% sodium deoxycholate and 1 mM EDTA) with phosphatase inhibitor (Sigma) and protease inhibitors (Millipore) for 15 min in ice followed by centrifugation. Nuclear and cytoplasmic fractions were isolated using Subcellular Protein Fractionation Kit (Thermo Fisher Scientific) according to the manufacturer's instructions. Protein concentrations were determined with the Biorad Protein Assay (Biorad). Proteins were separated on precast 8-12% Mini Protean TGX gels at 60-80 V using the Mini Protean electrophoresis system and were blotted onto PVDF membrane at 100V for 90 min in a Mini Trans-Blot Cell. All antibodies were used as recommended by the manufacturer and mentioned in Key Resource Table. Relative band intensities were quantified using ImageJ software.

Carbon Copy Chromosome Conformation Capture (5C). Experimental Design: The 3C libraries were generated as described before (Hnisz et al., 2016; Naumova et al., 2012), with the following modifications: 1) After HindIII digestion no SDS was added for restriction enzyme inactivation. 2) The ligation volume as 1.2 ml for $5 \times 10^6$ cells and a total of $3 \times 10^7$ ME-1 cells were used per 5C library preparation. 5C was carried out as previously described (Dostie et al., 2006; Ferraiuolo et al., 2012; Lajoie et al., 2009), with one modification: gel purification after adapter ligation was replaced by an Ampure step to remove unligated DNA. 5C primers were designed for a 3.98 Mb region (chr8: 127,753, 661-131,737,521) around the MYC locus. 5C primers were designed at HindIII restriction sites using publicly available 5C primer design tools published previously (Lajoie et al., 2009). Primers were designed according to a double alternating scheme exactly as described before (Hnisz et al., 2016). Primers were designed for each HindIII fragment: one primer designed on the 5' end of the fragment, and one on the 3' end. For a fragment either a right 5' forward (FOR) and a left 3' reverse (LREV) primer, or a right 5' REV and a left 3' LFOR primer were designed. These two primer designs alternate along consecutive fragments throughout the entire region of interest. This design allows interrogation of all pairwise interactions among all fragments, which is not possible with a more simple alternating design used previously (Lajoie et al., 2009).

Primer settings: U-BLAST, 3; S-BLAST, 50, 15-MER, 800, MIN_FSIZE, 100; MAX_FSIZE, 50,000; OPT_TM, 65; OPT_PSIZE, 40. The 5C primer tails were: FOR/LFOR: T7 sequence 5'-TAATACGACTCACTATAGCC-3' (SEQ ID NO:39); REV/LREV: T3 sequence 5'-TCCCTTTAGT-GAGGGTTAATA-3' (SEQ ID NO:40). The full-length of all FOR/LFOR primers was 60 bases; the length of all REV/LREV was 61 bases. In total, we designed 359 forward (FOR), 367 left forward (LFOR), 367 reverse (REV) and 367 left reverse (LREV) primers that combined interrogate 532,158 long-range chromatin interactions. Primers sequences are listed in Table 1.

Generation of 5C libraries. A 5C multiplex primer annealing reaction was performed overnight at 50° C. Pairs of annealed 5C primers were ligated at the same temperature using Taq-DNA ligase for 1 hr. Seven ligation reactions were performed to generate 5C libraries, except for the second biological replicate for AI-10-49-treated cells, where 14 ligation reactions were performed. Each ligation contained $6 \times 10^5$ genome copies, except for the second biological replicate for AI-10-49-treated cells, which contained 4×105 genome copies. Each primer was added to a final amount of 0.325 fmole. Ligated 5C primer pairs, which represent a specific ligation junction in the 3C library and thus a long-range interaction between the two corresponding loci, were then amplified using 20 cycles of PCR with T7 and T3R universal tail primers that recognize the common tails of the 5C forward and reverse primers. Four separate amplification reactions were carried out for each annealing reaction described above and all the PCR products of each library were pooled together. This pool constitutes the 5C library. The libraries were concentrated using Amicon Ultra Centrifugal filters—0.5 ml 30K (Millipore) and purified with Qiaquick PCR purification kit.

5C read mapping. 5C libraries were sequenced on an Illumina HiSeq 4000 instrument, reads were mapped (with Novoalign mapping algorithm V 3.02.00) and 5C interactions assembled exactly as described before (Lajoie et al., 2009; Sanyal et al., 2012). Data from the two biological replicates were pooled, producing a single interaction map for DMSO treated, and AI-10-49 treated cells. The summary statistics and the read depth of each 5C libraries can be found in Supplementary Table 2.

5C filtering and analysis. 5C matrices were processed using previously described methods (Lajoie et al., 2009; Sanyal et al., 2012). Briefly, first we removed 5C interactions that represent self-ligated restriction fragments. Second, in 5C PCR can lead to over amplification of individual pair-wise interactions (outliers). To remove these, first the average interaction frequency and standard deviation of all pair-wise interactions as a function of their genomic distance using LOWESS smoothing, as described in Sanyal et al. (Sanyal et al., 2012) was calculated. This average value represents the expected interaction frequency for a pair of loci. Then the observed/expected ratio for each interaction and expressed this as a z-score ((observed−expected)/standard deviation; (Sanyal et al., 2012)) was calculated. Outliers were then defined as those interactions with a z-score greater than 20 in each dataset. The union of all outliers identified in the four 5C datasets were taken, and these interactions from all four datasets were removed. Third, some primers strongly over or underperform leading to strongly enriched or depleted rows of interactions. To identify these primers the sum of all interactions detected with each of the 5C primers were calculated. Then, over- and underperforming primers were defined as those with a sum that is outside the 1.5 times the interquartile range (of the distribution of all row/col sums). Then, the union of all flagged primers across the four 5C matrices was taken, and these were removed from all four datasets. Fourth, the four matrices to the same number of total reads ($5 \times 10^7$) were scaled. Fifth, the matrices were balanced according to the ICE method so that the sum of each row and each column is equal (Imakaev et al., 2012). Sixth, data were binned at 20 Kb (median) with a sliding window with 2.5 Kb steps, or at 15 Kb (median) with a sliding window with 2.5 Kb steps when data were plotted as interaction profiles of single loci (4C-style plots). Seventh, matrices were balanced again after binning.

4C-style plots. To display the interaction profiles (4C-style plots) of selected loci rows for corresponding bins that overlap the Myc Promoter, ME1-ME2- and E3 enhancers from the 15 Kb binned 5C interaction matrix were extracted. The LOWESS smoothed average plus and minus 1 standard deviation of 5C signal as a function of genomic distance (representing the expected 5C signal) were calculated and plotted.

Integrative analysis of high-throughput data. All downstream analyses were carried out using R v 3.4.1 (R Core Team, 2016) and BioConductor v 3.4 (Huber et al., 2015). Exploratory analyses and differential gene expression analysis were carried out with CummeRbund package v 2.7.4 (http://compbio.mit.edu/cummeRbund/). The enriched regions/peaks of CHIP-seq and ATAC-seq were annotated to the hg19 genomic features with ChIPpeakAnno (Zhu, 2013; Zhu et al., 2010). The heatmaps and density plots were also generated with ChIPpeakAnno. The Bioconductor diffbind package v 2.4.8 (Ross-Innes et al., 2012) was used to quantitate and identify genomic regions with differential binding by ATAC-Seq or CHIPdseq reads between control and AI-10-49 treated samples. To identify motifs associated with RUNX1 binding sites, the weight matrices of different consensus binding sites for various transcription factors were obtained from Jaspar database (http://jaspar.genereg.net/). The overlapping of peaks with RUNX1 binding motif and those with other binding motifs were analyzed by ChIPpeakAnno. To visualize all genomic data, narrowPeak or bigwig files were uploaded to the UCSC Genome Browser. All genomic data are accessible at the Gene Expression Omnibus (accession number: in process).

Statistical Analysis. Analysis was performed using R, a system for statistical computation and graphics (Ihaka and Gentleman, 1996). For mouse leukemia survival analysis, the leukemia latency and P-values were estimated using Survival package in R. P-value between groups was calculated using log-rank test. Relative cell viability, measured as the proportion of viable cells, was first arcsine-transformed to homogenize the variance. Levene's test shows that the assumption of homogeneity of variances is met. One-way ANOVA was performed followed by predetermined contrasts for FIGS. 2A, 2B, 2C, 2D, 2E, 4D and 7C. Two-way ANOVA was performed followed by Tukey's honest significance test for FIG. 3C. To compare the response curves (FIGS. 3A & 3D), an indicator variable was created to distinguish the two-drug treatment and one of the single-drug treatments. Two-way ANOVA was performed to compare a single-drug treatment and the two-drug treatment.

Figure 9A:
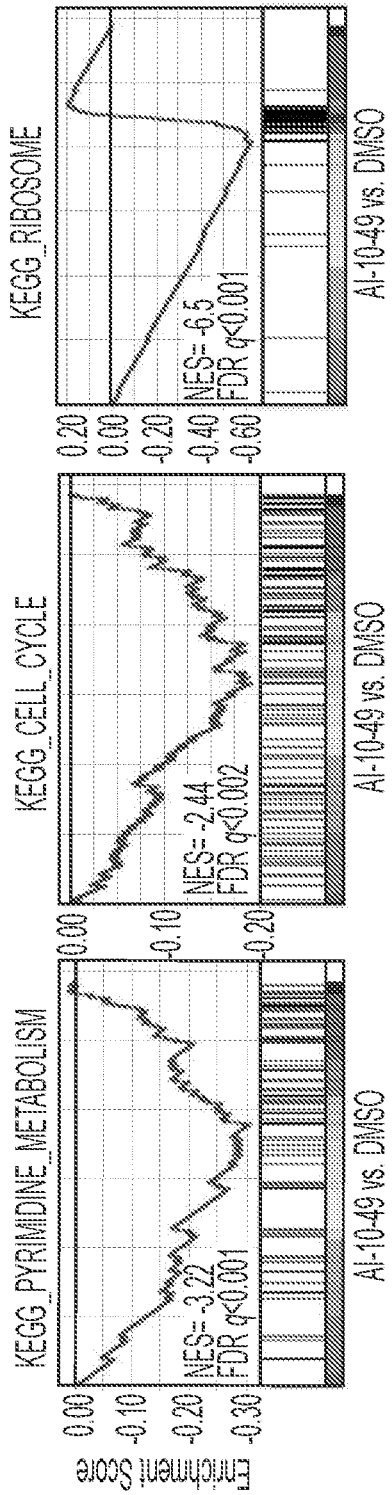
FIG. 9 (A-D) shows AI-10-49 mediated MYC transcriptional changes is specific to inv(16) cells. (A, B) show gene set enrichment analysis depicting pyrimidine metabolism, cell cycle and ribosome biogenesis (A) and pathway signatures (B) that are positively correlated with AI-10-49 in ME-1 cells. (FDR) false discovery rate; (NES) normalized enrichment score. (C) shows MYC transcript levels in non-inv(16) AML cells (U937, K562, Jurkat, Kasumi-1 and THP-1) treated with DMSO or 1 μM AI-10-49 for 6 hrs. (D) is an immunoblot depicting MYC and GAPDH protein levels in ME-1 cells treated with 1 μM AI-10-49 for 0 hrs, 2 hrs, 4 hrs and 8 hrs.
Figure 9B:
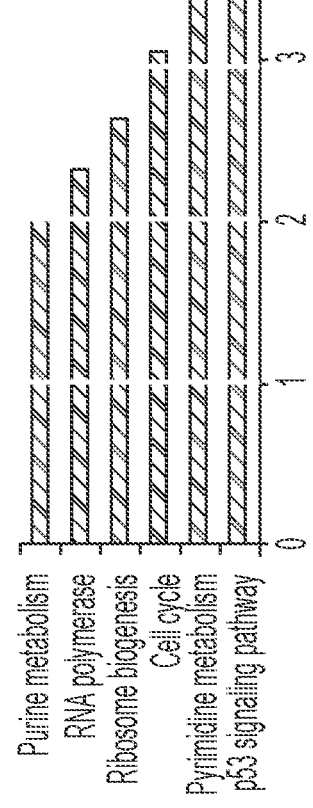

Example 1: Inhibition of CBFβ-SMMHC activity by AI-10-49 represses MYC transcript expression. The expression of CBFβ-SMMHC is critical for inv(16) AML blast survival, and the small molecule inhibitor AI-10-49 selectively triggers apoptosis of human and mouse inv(16) AML cells (Illendula et al., 2015). In order to identify pro-apoptotic AI-10-49 targets, RNA-sequencing analysis was performed in human inv(16) AML cell line ME-1 treated with AI-10-49 for 6 hrs. Expression analysis of triplicate samples identified 591 upregulated and 696 downregulated genes (>2 fold change, FDR<0.01; FIG. 1(A)). Amongst the top repressed genes, MYC levels were repressed over 10-fold and E2F1 3-fold. Gene Set Enrichment Analysis (GSEA) of the RNA-seq dataset revealed that AI-10-49 treatment was associated with MYC and E2F signatures (FIG. 1B), and MYC-associated pathways, including cell cycle, amino acid metabolism and ribosome biogenesis (FIGS. 9A and 9B).

Figure 9C:
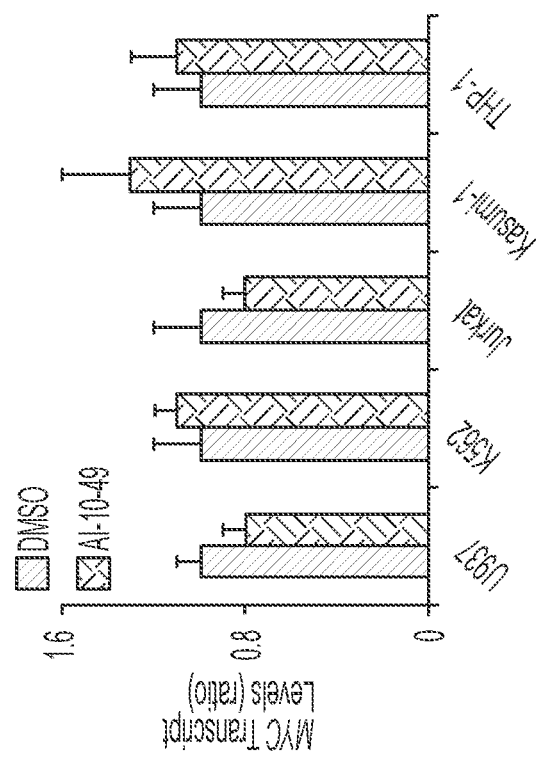
Figure 9D:
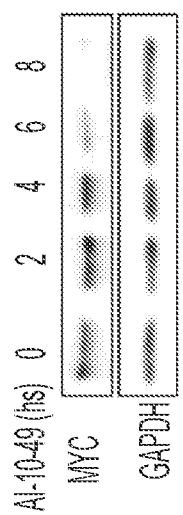

AI-10-49 directs strong (10-fold) repression of MYC transcript levels (FIG. 1 (C)) in ME-1 cells but not in non-inv(16) AML cell lines (FIG. 9C). Accordingly, MYC protein levels were significantly depleted (approximately 20-fold) at 0.1 μM and greater concentrations in ME-1 cells (FIG. 1D and FIG. 9D). Concordant with these results, MYC expression was reduced by AI-10-49 in mouse Cbfb$^{+/MYH11}$ and human primary inv(16) AML cells (FIGS. 1E and 1F). Normal hematopoietic cells from primary mouse bone marrow and human CD34$^+$ hematopoietic cells were not affected by AI-10-49 treatment, further confirming that AI-10-49-mediated modulation of MYC expression is specific to CBFβ-SMMHC-expressing AML cells.

Example 2: MYC is required for the maintenance and survival of inv(16) AML cells. c-MYC levels were analyzed for regulation of survival in inv(16) AML. The knockdown of MYC, using MYC-shRNAs, reduced viability of ME-1 cells 66% and primary mouse Cbfb$^{+/MYH11}$ leukemic cells 70% (FIGS. 2A, 2B, and FIGS. 10A and 10B). Furthermore, ectopic MYC expression, using an MYC-ER system (Ricci et al., 2004), resulted in a partial rescue of AI-10-49 mediated apoptosis (FIG. 2C). These results suggest that reduced MYC levels mediate AI-10-49 induced apoptosis. Considering that MYC silencing is required for granulocytic differentiation of myeloid cells (Johansen et al., 2001), MYC knockdown in ME-1 cells was investigated. The fraction of cells with myeloid markers (CD15$^+$ and CD11b$^+$) 14 days after transduction was not significantly altered (FIG. 10C), suggesting that MYC repression primarily directs apoptosis and not differentiation of inv(16) AML cells.

Figure 2D:
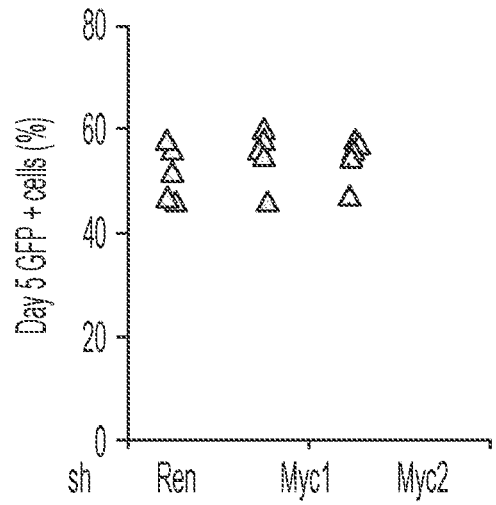
FIG. 2 (A-F) shows that MYC is required for the survival of inv(16) cells. (A-B) show that MYC silencing reduced viability of inv(16) AML cells. ME-1 cell line (A) and primary mouse Cbfb$^{+/MYH11}$ (mCM-LK) leukemic cells (B) were transduced with scramble or MYC shRNAs and assessed live cells (7AAD-Annexin V-) by Annexin V assay. Annexin assay was conducted 14 days after viral infection for ME-1 cells (A) or 7 days for primary mouse leukemic cells (B). Each data point represents the mean of triplicate experiments; error bars represent the SD. (C) shows that MYC overexpression by MYC-ER partially rescued viability of ME-1 cells treated with AI-10-49. Cells expressing MYC-ER were treated with ethanol or 500 nM 4-HT for 9 hrs followed by treatment with DMSO or AI-10-49 (1 μM) for 24 hrs and assessed live cells (7AAD-Annexin V-) by Annexin V assay. Each data point represents the mean of triplicate experiments; error bars represent the SD. (D-E) Leukemic cells were transduced with indicated shRNAs, GFP+ leukemic cells transplanted to wild type C57BL/6 mice and analyzed GFP+ cells in bone marrow 5 days after transplantation (D) and analyzed c-kit+ cells in peripheral blood 28 days after retroviral infection (E). (F) shows Kaplan-Meier survival curve of mice transplanted with control/Myc shRNA transduced leukemic cells. For panels A-E, significance was calculated as Levene's test, *P<0.05, or **P<0.005. For panel F, significance was calculated using log-rank test. See also FIG. S2.
Figure 2E:
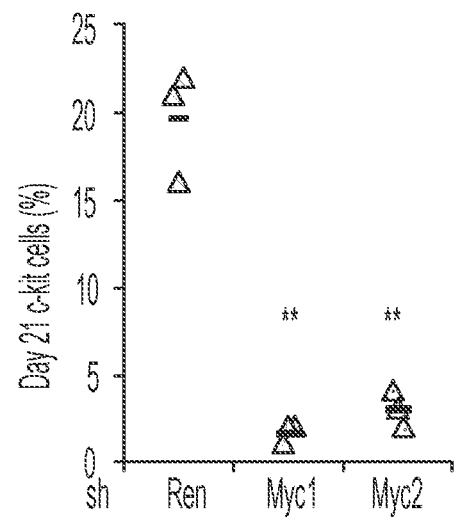
Figure 2F:
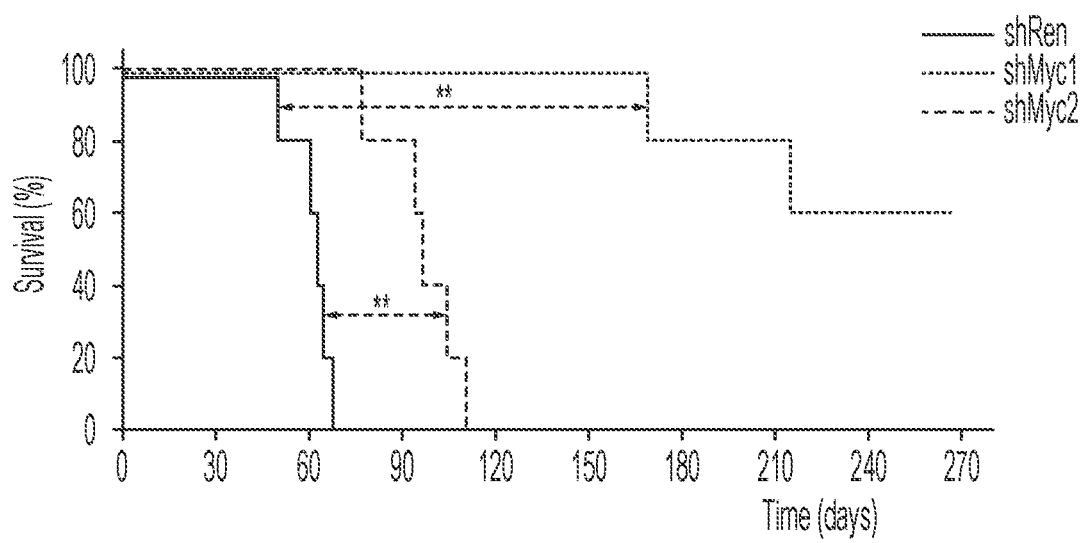
Figures 10A, 10B:
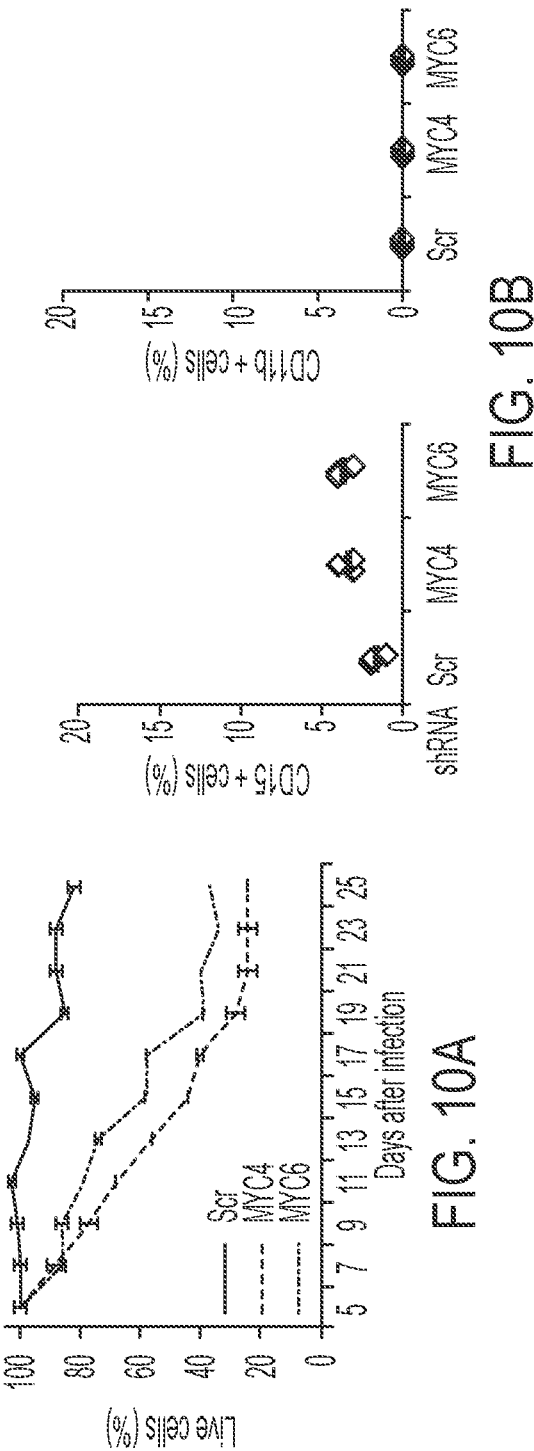
FIG. 10 (A-G) shows the effect of MYC silencing in inv(16) AML cells. (A) shows a time course analysis of cell viability (7AAD-Annexin V-) in ME-1 cells transduced with scramble (Scr) or two MYC shRNAs. (B) shows flow cytometry analysis of granulocytic differentiation in ME-1 cells transduced with MYC shRNAs at day 14. (C and D) show analysis of MYC protein levels assessed by western blot analysis (C) and cell viability (7AAD-Annexin V-; D) of AML cell lines Kasumi-1, NB4, ME-1, THP1, MV4:11 and K562, 14 days after transduction with MYC shRNAs; each data point represents the mean of triplicate experiments; error bars represent the SD. (E) is an immunoblot analysis of Myc and Gapdh protein levels mouse Cbfb$^{+/MYH11}$ leukemic cells transduced with Renila (Ren) or Myc shRNAs 1 and 2. (F) is a schematic representation of experimental design for in vivo evaluation of Myc shRNA knockdown experiments. (G) Immunoblot analysis of Myc and Gapdh protein levels in Cbfb$^{+/MYH11}$ leukemic cells of leukemic mice (Ren, shMyc1 and shMyc2 groups) from secondary transplant assays shown in FIG. 2G. Each band represents Myc total protein levels of leukemic cells isolated from a single mouse. Significance was calculated using Levene's test (D). *$p<0.05$, or **$p<0.005$.
Figure 10D:
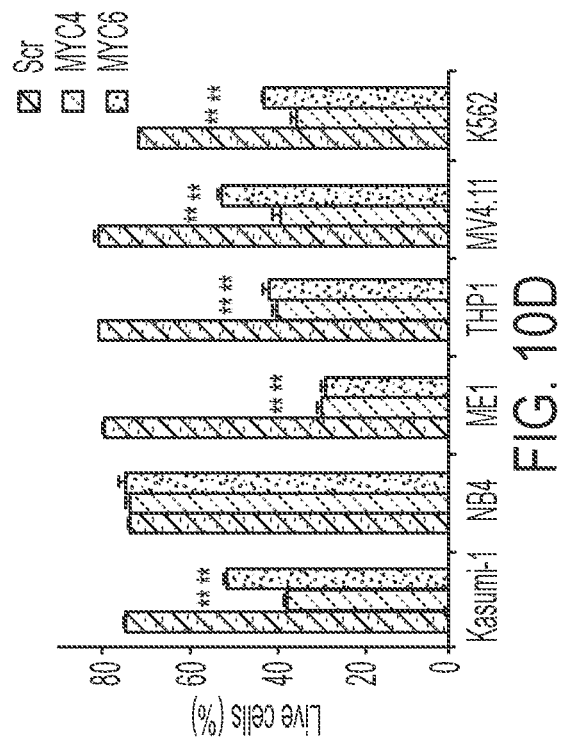
Figure 10C:
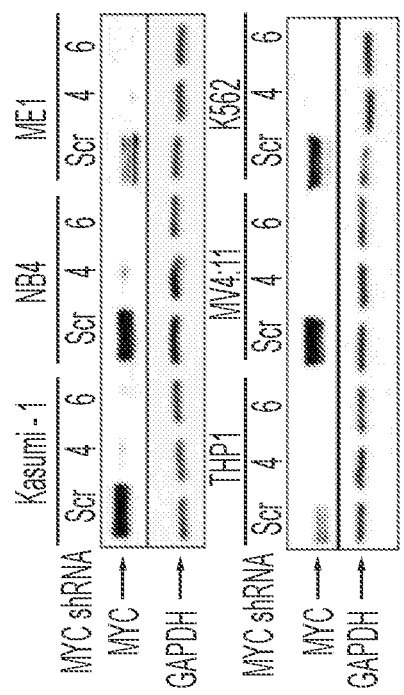
Figure 10E:
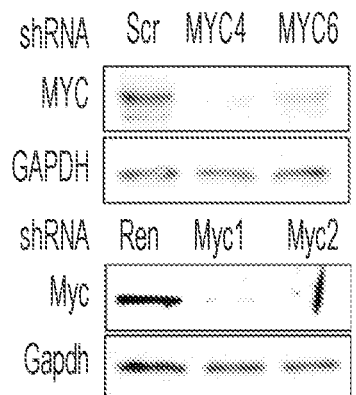
Figure 10F:
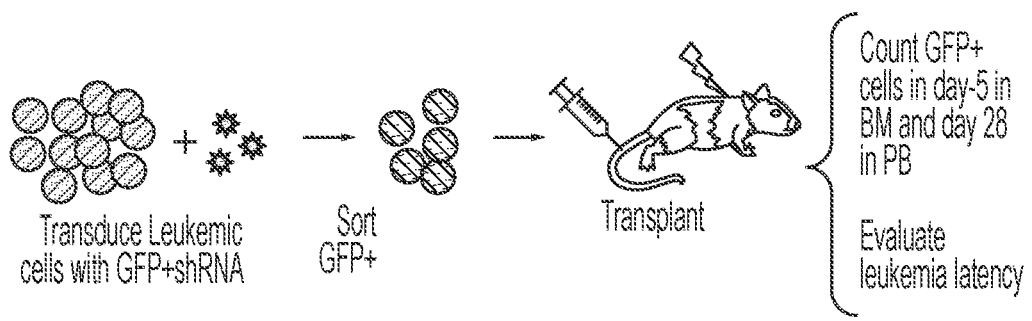
Figure 10G:
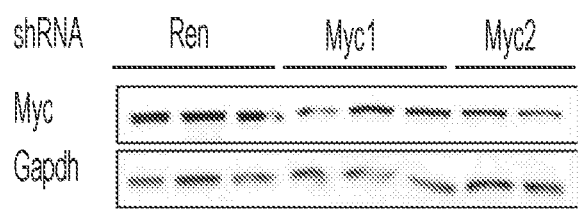

The requirement for Myc function in the survival of inv(16) leukemia was tested in mice transplanted with CBFβ-SMMHC-expressing leukemic cells (Nras+/LSL-G12D,Cbfb+/56M,Mx1Cre; Nras/CM; (Xue et al., 2014)) transduced with Renilla- or 2 Myc-shRNAs in retroviruses expressing GFP (FIG. 10D). The engraftment efficiency of GFP+ leukemic cells in bone marrow five days after transplantation was similar between groups (FIG. 2D). However, the fraction of leukemic cells in peripheral blood 28 days after transplantation revealed a marked reduction in mice transplanted with Myc shRNAs, suggesting that Myc is required for the maintenance of inv(16) leukemic cells (FIG. 2E). Furthermore, the median latency of leukemia in mice with reduced Myc levels was significantly prolonged from 62 days (Renilla group) to incomplete penetrance (shMyc1) and 96 days (shMyc2; p=0.00184, FIG. 2F). Myc levels in the leukemic cells from either Myc-shRNA group were similar to that of Renilla group (FIG. 10E), suggesting that sustained reduction in Myc levels had been lost in these clones. Therefore, these in vitro and in vivo experiments in mice demonstrate that modulation of MYC oncogene levels is critical to the survival and expansion of inv(16) leukemic cells.

Figure 3A:
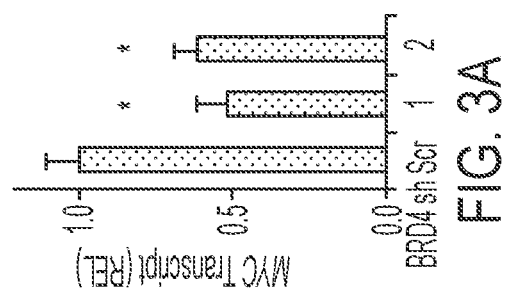
FIG. 3 (A-F) shows inhibition of MYC by AI-10-49 and JQ1 leads to synergistic efficacy against inv(16) leukemia cell survival. (A) shows MYC transcript level analysis in ME-1 cells transduced with BRD4 shRNAs (sh1 and sh2), by qRT-PCR. (B) shows MYC transcript level analysis after dose response treatment with AI-10-49 and JQ1. (C) is an isobologram plot showing synergism between AI-10-49 and JQ1 in combined treatment. (D and E) show viability analysis of primary inv(16) AML cells (D) and mouse leukemic cells (E) treated with AI-10-49 and JQ1. (F) is a Kaplan-Meier survival curve of mice (n=5-6 per group) transplanted with mouse leukemic cells and treated with DMSO (black line), JQ1 (blue line), AI-10-49 (red line), or JQ1 and AI-10-49 (green line). Error bars represent SD. Significance was calculated using an unpaired t test (A), Levene's test (B-E), or log-rank test (F). *p<0.05 or **p<0.005. For panel E, significance was calculated using log rank test.
Figure 3B:
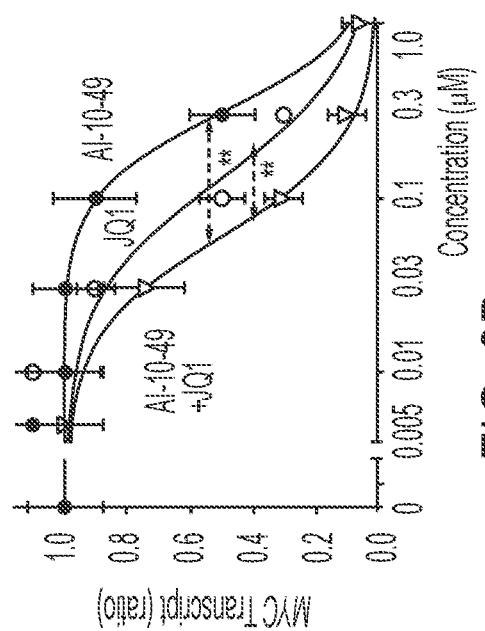
Figure 3C:
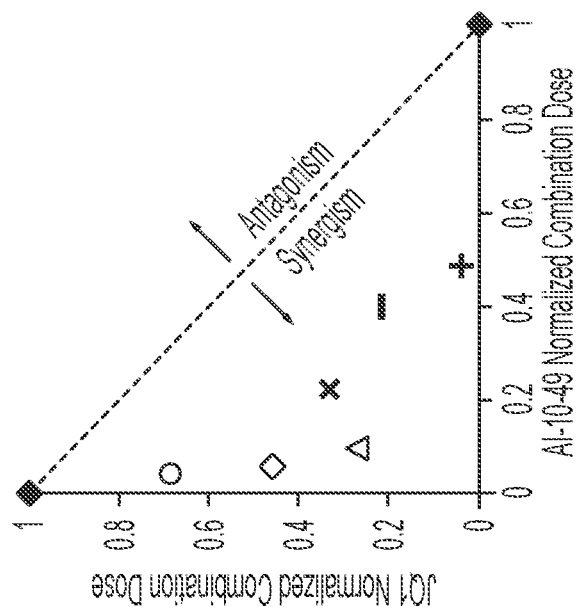
Figure 11E:
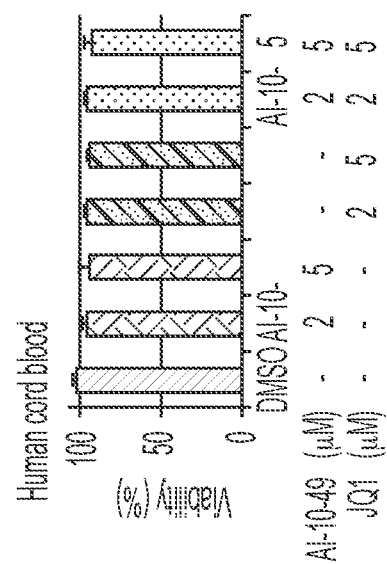
FIG. 11(A-J) shows effect of JQ1 mediated MYC silencing in inv(16) cells and non(inv16) cells. (A) shows qRT-PCR analysis of BRD4 transcript levels in ME-1 cells transduced with scramble (Scr) or two BRD4 shRNAs (sh1 and sh2). (B) shows an immunoblot analysis of MYC and GAPDH protein levels in ME-1 cells treated with BET inhibitor JQ1 for 6 hr. (C) is a dose response viability analysis (MTT assay) of ME-1 cells treated with AI-10-49 and/or JQ1 for 72 hr; the LD50 for each compound is: AI-10-49-LD50=0.468 mM, range=0.398-0.537 mM; JQ1-LD50=0.344 mM, range=0.228-0.460 mM; both at 95% confidence intervals. (D) shows the percentage of c-kit+ (leukemic) cells in peripheral blood 25 days after transplantation in respective groups, assessed by flow cytometry. (E) shows a viability analysis (MTT assay) of JQ1 and AI-10-49 in human cord blood CD34+ cells 48 hr after treatment with AI-10-49 and/or JQ1 at the indicated concentrations. (F-J) are toxicology analysis of wild-type mice treated with a daily dose of DMSO (green) or 200 mg/kg/day AI-10-49 (10 days) and 50 mg/kg/day JQ1 (21 days) (49+JQ1, green). Mice were analyzed 1 day after last treatment dose; body weight (F), spleen weight (G), bone marrow cellularity (H), percentage of stem and early progenitor cells [LSK+: Lin(-) Sca1(+) c-kit(+)] in bone marrow (I), percentage of progenitor cell compartments common myeloid progenitors [CMP: LSK-, CD34(+)CD16/32(-)], megakaryocyte/erythroid progenitors [MEP: LSK-, CD34(-)CD16/32(-)], and granulocyte/monocyte progenitors [GMP: LSK-, CD34(+)CD16/32(+)], in LSK- cells (J). Each symbol represents the mean of values from three animals; error bars represent the SD. Significance was calculated using unpaired t test (A) or Levene's test (D). *$p<0.05$, or **$p<0.005$.
Figure 11D:
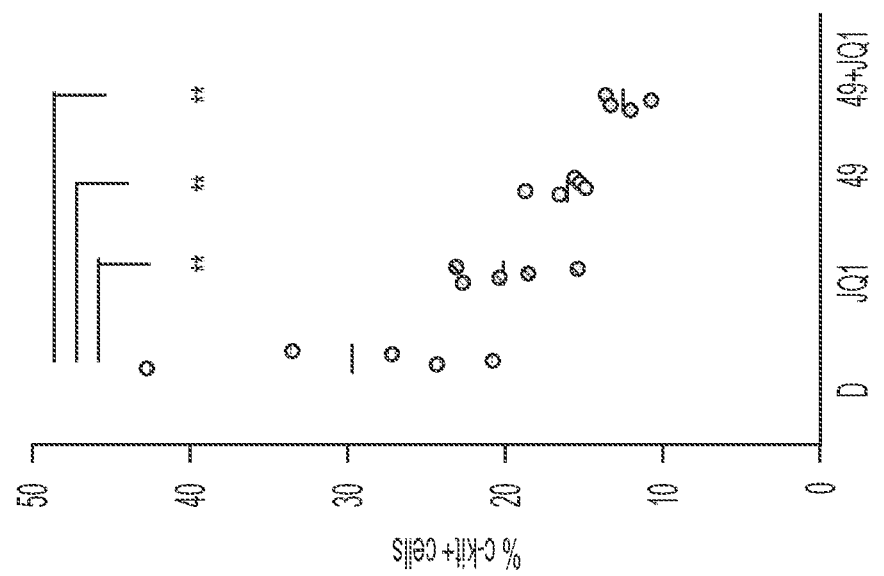

Example 3: AI-10-49 cooperates with JQ1 to reduce inv(16) AML cell survival. Bromodomain (BRD) proteins have been established as key drivers of oncogenic transcription factors such as MYC (Delmore et al., 2011). The BET-family of BRD inhibitors, such as JQ1 and I-BET151, are potent BRD inhibitors that repress MYC levels (Dawson et al., 2011; Delmore et al., 2011), and second generation BRD-inhibitors are being tested in the clinic. Upon finding that AI-10-49 represses MYC transcription inv(16) AML cells' sensitivity to combination treatment with AI-10-49 and JQ1 was investigated. MYC expression depends on BRD4 in inv(16) AML by estimating MYC levels in ME-1 cells upon BRD4 knockdown (FIGS. 3A and 11A). The MYC transcript and protein levels were readily reduced by AI-10-49 and JQ1 treatment of ME-1 cells, and combined treatment showed a cooperative effect in MYC transcript levels (FIGS. 3B and 11B). Remarkably, the combination index (CI) analysis (Chou, 2010) of combined AI-10-49 and JQ1 treatment at various concentrations of the two agents consistently showed CI values below 1 (FIGS. 3C and 11C), indicative of a substantial synergy of JQ1 and AI-10-49 on ME-1 cell growth. The cooperativity between these inhibitors was further demonstrated in primary human inv(16) AML and mouse inv(16) leukemic cells (FIGS. 3D and 3E, respectively). Conversely, the viability of human $CD34^+$ cord blood cells was not affected by the combined treatment with AI-10-49 and JQ1 (FIG. 11E), suggesting cooperative effect of AI-10-49 and JQ1 is specific to inv(16) AML cells.

Figure 3F:
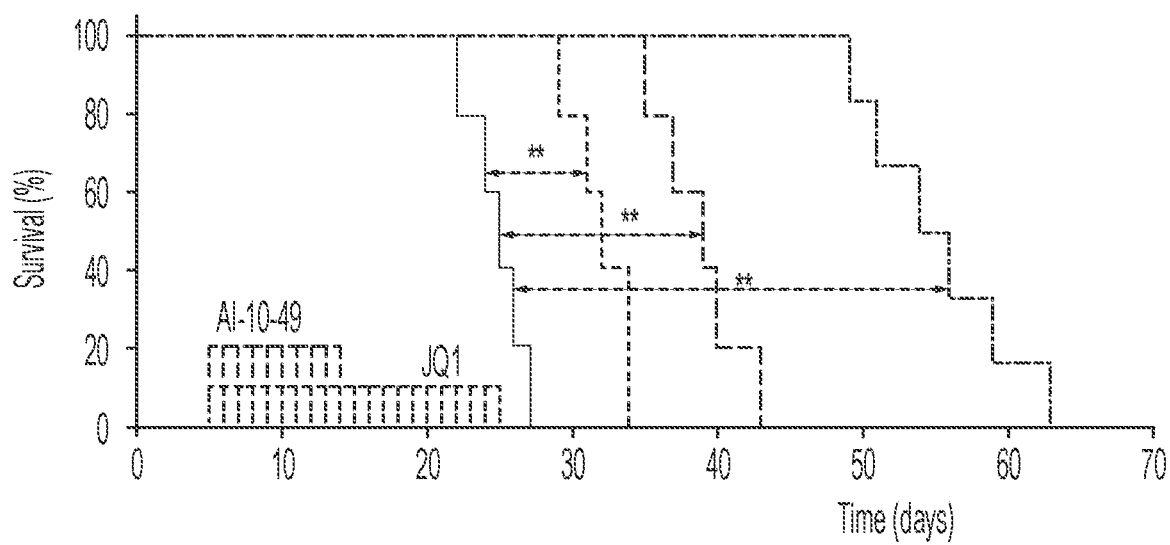
Figures 11F, 11G:
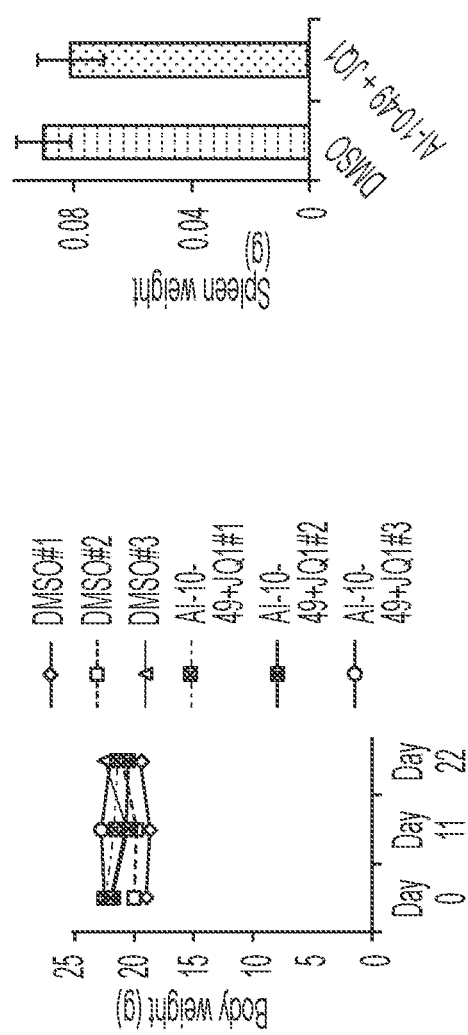
Figure 11H:
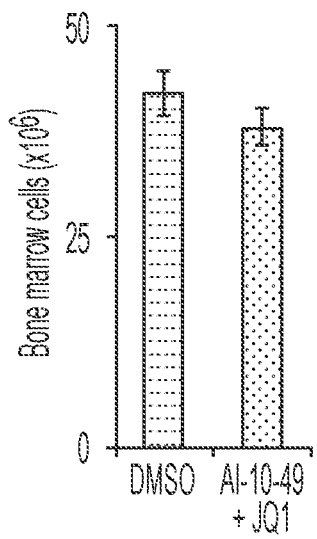
Figure 11I:
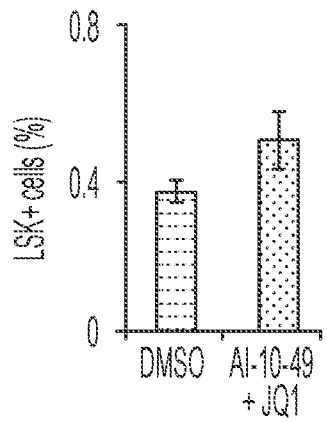
Figure 11J:
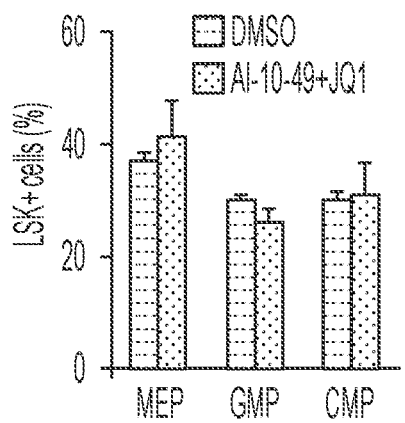

To test the therapeutic value AI-10-49 and JQ1 combined treatment in vivo, the leukemia latency of mice transplanted with CBFβ-SMMHC-expressing (Nras+/LSL-G12D/Cbfb+/56M/Mx1Cre; Nras/CM) leukemia cells was analyzed. Five days after transplantation, mice were randomized in four groups, and treated with vehicle (dimethyl sulfoxide, DMSO), AI-10-49 for 10 days, JQ1 for 21 days, or combined treatment of AI-10-49 and JQ1 (FIG. 3F). The median latency of leukemia was prolonged from 25 days (DMSO) to 32 (JQ1) and to 39 days (AI-10-49) when treated with one drug (p=0.00184), and to 55 days when treated with both inhibitors (p=00017). Treatment of AI-10-49 and JQ1 in wild type C57BL/6J mice did not reveal measurable toxicity (FIGS. 11F and 11J). Collectively, these findings demonstrate the effectiveness of AI-10-49 and BET inhibitors in inv(16) AML.

Example 4. AI-10-49 enhances genome wide RUNX1 DNA binding. AI-10-49 inhibits CBFβ-SMMHC/RUNX1 binding, and increases the occupancy of RUNX1 to selected RUNX target gene promoters (Illendula et al., 2015). To understand the impact of AI-10-49 in RUNX1 association with the chromatin, chromatin immune-precipitation was conducted, followed by next generation sequencing (ChIP-seq) in ME-1 cells treated with AI-10-49 for 6 hrs. Analysis of Histone3-Lysine27 acetylation (H3K27ac) peaks, which mark transcriptionally active regions, indicated a significant decrease in positive peaks (31,102 for DMSO versus 24,157 for AI-10-49) (FIG. 4A). AI-10-49 promoted a general reduction in the peaks. These results suggest that AI-10-49 triggers a global reduction in transcription activity.

Figure 12A:
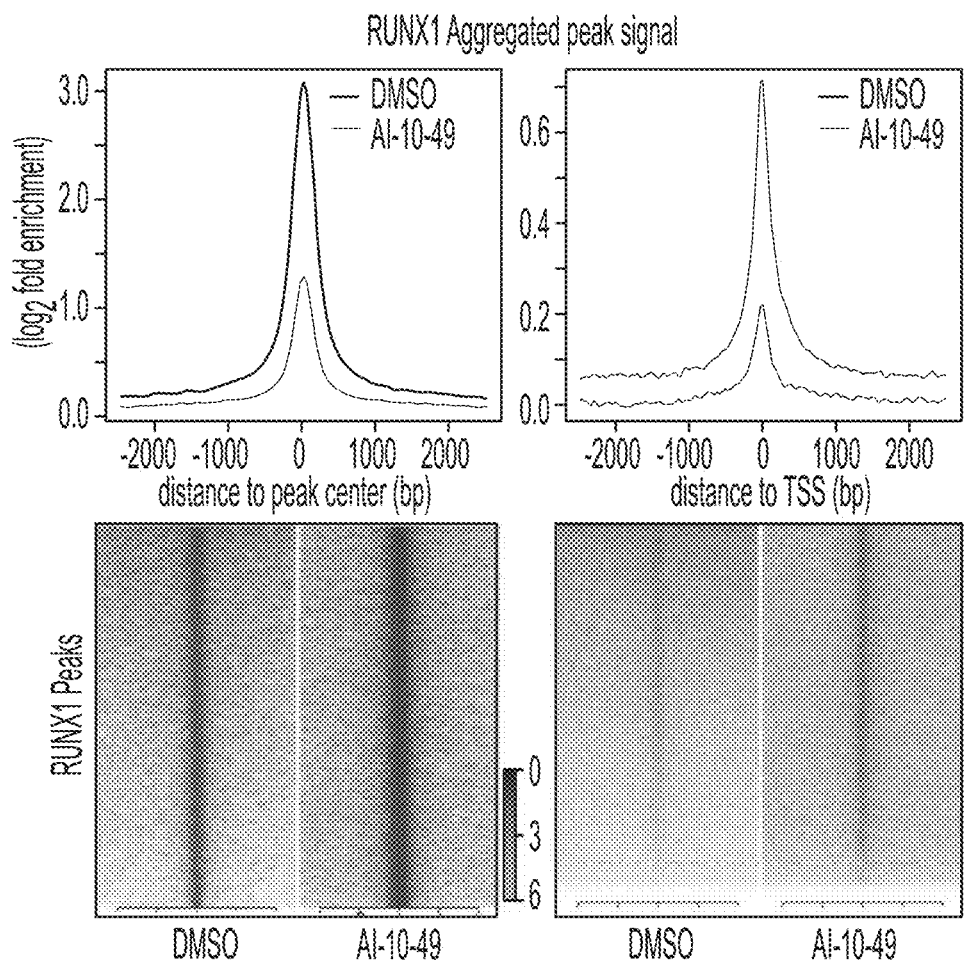
FIG. 12(A-B) shows that AI-10-49 leads to genome wide RUNX1 binding in inv(16) cells. (A) shows binding intensity at RUNX1 peaks with respect to distance from RUNX1 peak center (left) and distance to transcription start site (right). (B) shows gene distribution of H3K27Ac (top) and RUNX1 (bottom) peaks in ME-1 cells treated with DMSO (left) or AI-10-49 (right).
Figure 12B:
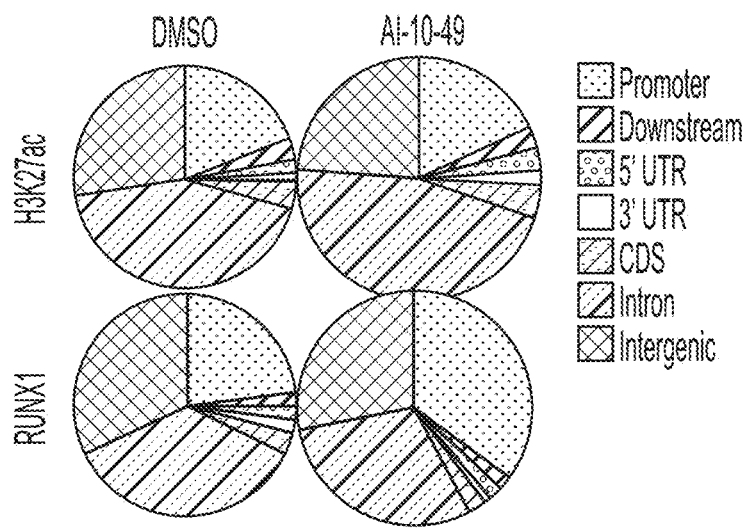

ChIP-seq analysis for RUNX1 revealed that AI-10-49 treatment induces a 7-fold increase (991 sites for DMSO versus 6,652 for AI-10-49) in RUNX1 binding to target regulatory elements (FIG. 4B). Examination of the frequency distribution of RUNX1 binding at the peak center and at the nearest TSS revealed a clear increase in RUNX1 signal intensity (FIGS. 4B and 12A). Analysis of peak distribution indicated a relative enrichment for promoter regions (FIG. 12B). These results revealed that AI-10-49-mediated acute release of RUNX1 from CBFβ-SMMHC can trigger RUNX1 re-localization to regulatory regions in inv (16) AML cells.

Motif analysis revealed that RUNX1 occupied elements were highly enriched for ETS and AP-1 binding motifs (FIG. 4C). Association of RUNX1 with ETS factors has been reported in RUNX1-ETO positive leukemic cells (Ptasinska et al., 2012). AP-1 transcription factors were up-regulated by RUNX1 during megakaryocytic differentiation and recruited to RUNX1-occupied sites lacking AP-1 motifs (Pencovich et al., 2011). These data suggest that RUNX1 may cooperate with ETS factors to regulate gene expression during AI-10-49 treatment in inv(16) AML cells.

RUNX1 can regulate chromatin remodeling during myeloid differentiation in mice (Hoogenkamp et al., 2009). Since it was observed that AI-10-49 increases RUNX1 association with DNA, AI-10-49 was evaluated for whether it can modulate chromatin accessibility in ME-1 cells, using Assay for Transposase-Accessible Chromatin with high throughput sequencing (ATAC-seq; (Buenrostro et al., 2013)). Analysis of ATAC-seq data in cell treated with DMSO or AI-10-49 revealed that AI-10-49 induced a significant reduction in chromatin accessibility (FIG. 4D). These results suggest that AI-10-49-mediated RUNX1 activity promote a global reduction in chromatin accessibility.

Figure 5A:
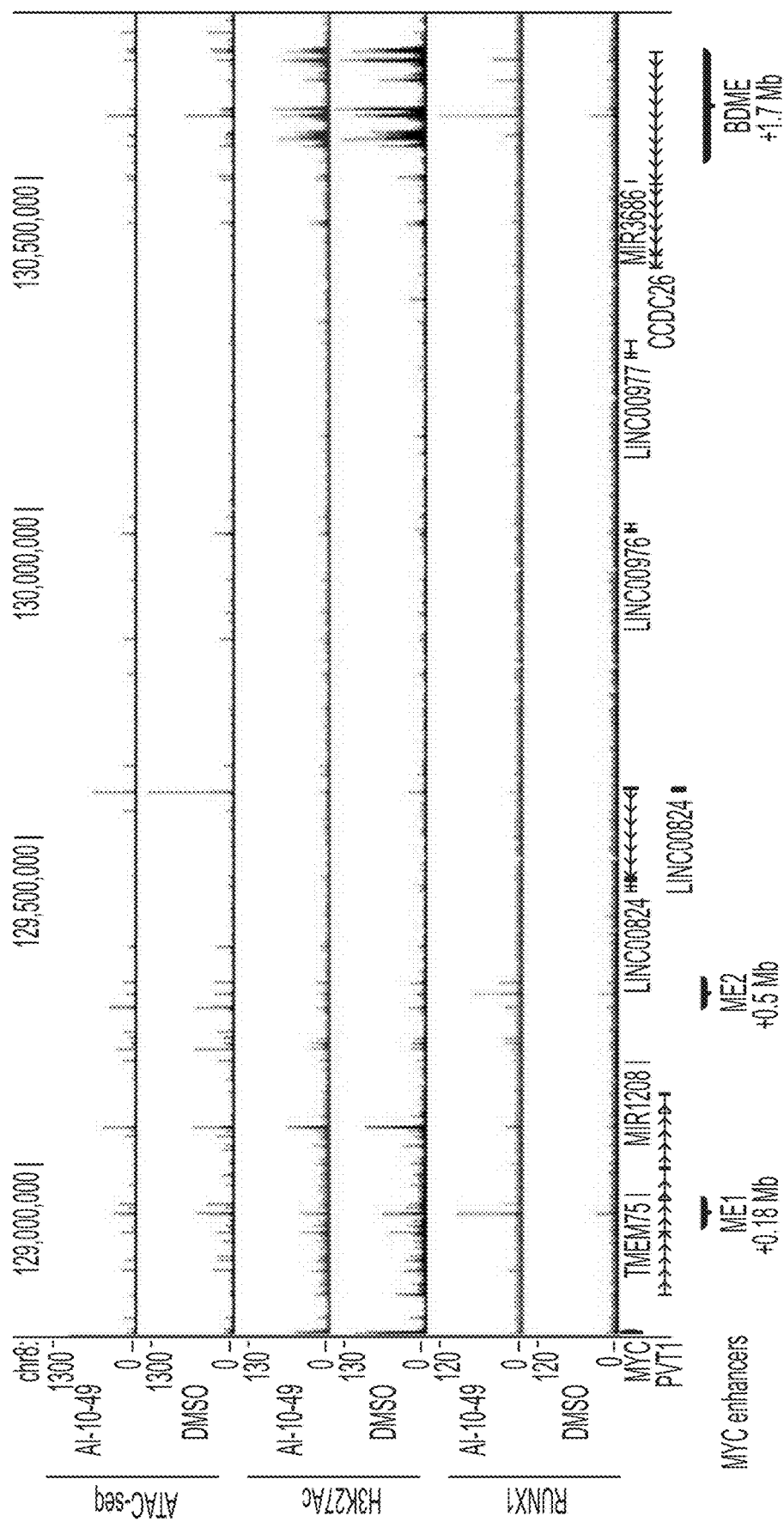
FIG. 5 (A-D) shows that RUNX1 increases association with chromatin at three distal MYC in inv(16) cells. (A) shows ATAC-seq and K3K27ac and RUNX1 ChIP-seq profiles in a 2 Mb genomic region downstream of MYC. The tree enhancer regions (ME1, ME2 and BDME) are depicted below the profile in green. (B-D) are ChIP-qPCR analysis for RUNX1 in DMSO- or AI-10-49-treated cells (B) and DMSO- or AI-10-49-treated human primary CD34+ inv(16) AML cells (C) and for p300 in DMSO or AI-10-49-treated ME1 (D). Significance was calculated as unpaired t-test, *P<0.05, or **P<0.005.
Figure 13A:
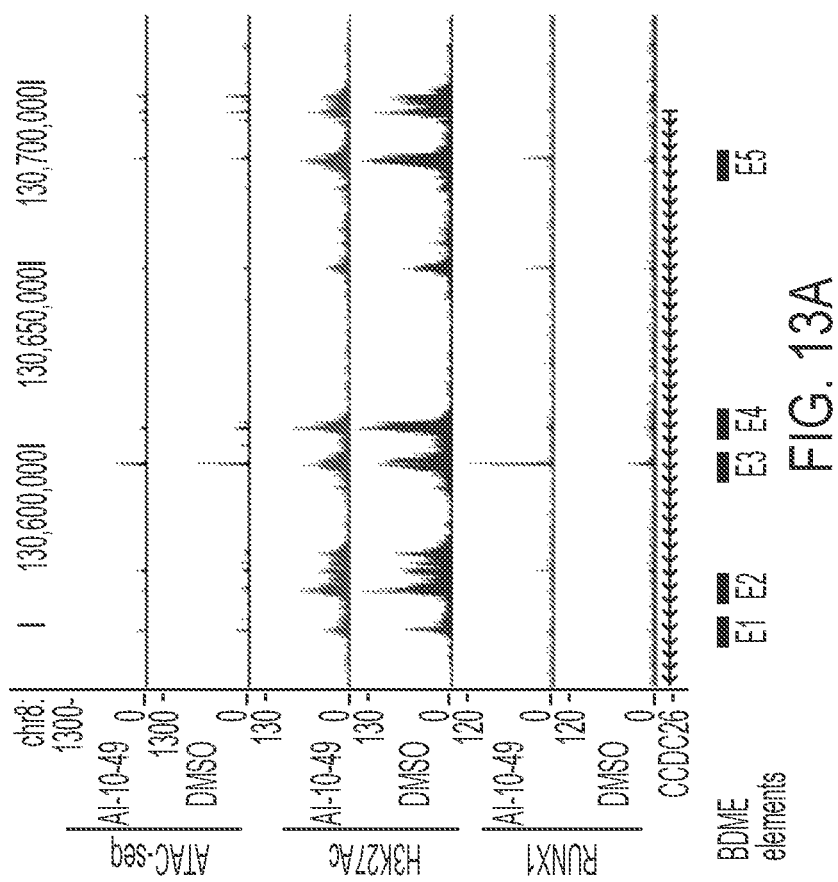
FIG. 13(A-B) shows RUNX1 mediated chromatin changes at MYC enhancer elements with AI-10-49. (A) shows ATAC-seq and ChIP-seq profiles for K3K27ac and RUNX1 in MYC+1.7 Mb genomic region. Five previously reported enhancer regions (E1 to E5) depicted below the profile. (B) shows ChIP-seq profiles for K3K27ac and RUNX1 peaks in ME-1 cells treated with DMSO (blue) or AI-10-49 (red) in the 2 Mb genomic region upstream of MYC-TSS.
Figure 13B:
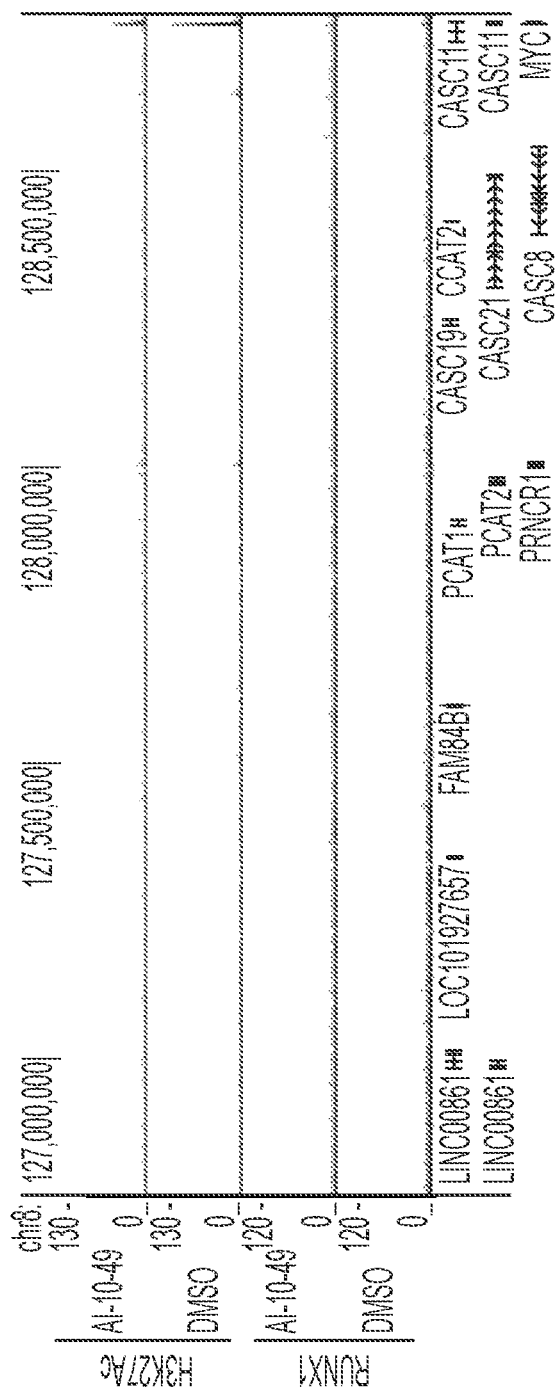

Example 5: RUNX1 represses MYC expression through direct binding at three downstream enhancer elements. Active enhancers regulate oncogene expression in cancer, including tumor-type specific distal enhancers that regulate oncogenic MYC expression in solid tumors (Hnisz et al., 2013; Loven et al., 2013; Pomerantz et al., 2009) and leukemia (Fulco et al., 2016; Herranz et al., 2014; Shi et al., 2013). Preliminary analysis of RUNX1 binding at the MYC promoter excluded the possibility that RUNX1 may directly regulate MYC expression through promoter occupancy in AI-10-49-treated inv(16) AML cells. It was hypothesized that AI-10-49-mediated RUNX1 function may repress MYC expression by perturbing active distal enhancers. To test this hypothesis, a 3 Mb genomic region surrounding the MYC-TSS was analyzed. Analysis of the 2 Mb downstream region revealed that AI-10-49 treatment did not significantly change chromatin accessibility (by ATAC-seq) and revealed a small reduction in H3K27ac mark (FIGS. 5A and 13A). Analysis of RUNX1 ChIP-seq data in this region identified three elements with significantly increased RUNX1 peaks in AI-10-49 treated cells. The primary RUNX1 peak was located within the BDME super-enhancer (BRD4-mediated MYC enhancer), 1.7 Mb downstream of the MYC TSS (FIG. 5A). The BDME, composed of five elements (E1-E5; FIG. 13A), has been shown to associate with the SWI/SNF proteins BRG1 and BRD4 to regulate MYC expression in myeloid cells and in mixed-lineage leukemia (Shi et al., 2013). This primary RUNX1 peak corresponds to the E3, which includes a RUNX1-consensus binding site. The two other RUNX1 peaks, called MYC enhancer 1 and 2 (ME1 and ME2), were located at 0.18 Mb at 0.5 Mb downstream MYC-TSS, respectively. We did not detect significant changes in RUNX1 peaks in the 2 Mb region upstream of MYC (FIG. 13B).

Figure 5C:
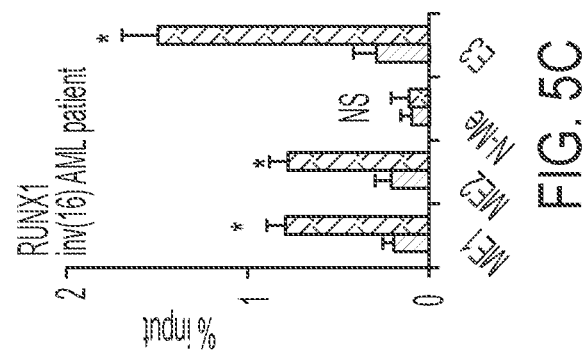
Figure 5B:
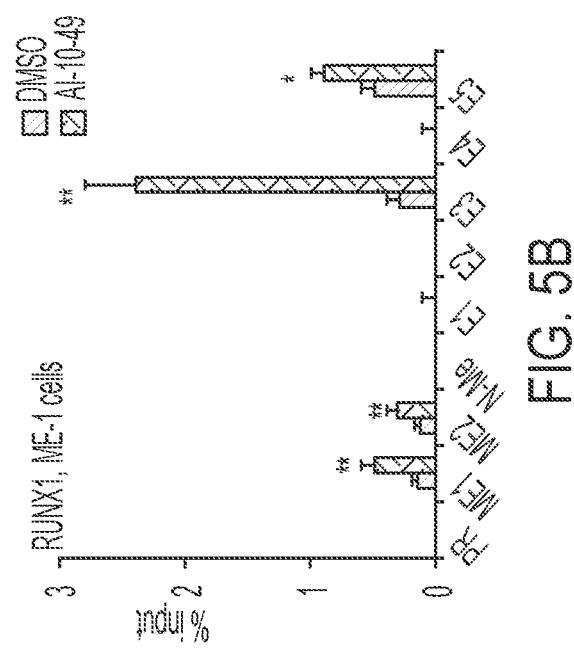
Figure 5D:
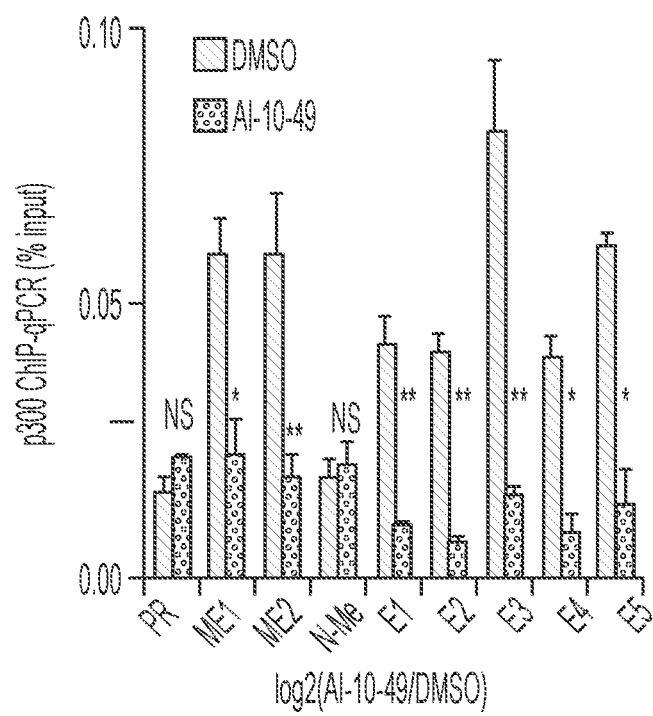

RUNX1 consensus binding sites (TGYGGT) were identified at the MYC promoter, ME1, ME2, and BDME elements E1, E3 and E5. ChIP-qPCR changes in RUNX1 peaks at eight sites, including MYC promoter, ME1 and ME2 enhancers and the five BDME elements, were evaluated. In addition, +1.4 Mb N-ME (the T-cell leukemia associated NOTCH-dependent MYC enhancer, also referred as NDME; (Herranz et al., 2014; Yashiro-Ohtani et al., 2014)) as a non-myeloid control enhancer was tested. RUNX1 peaks were significantly increased by AI-10-49 treatment at the ME1 (5-fold), ME2 (3-fold) and BDME-E3 (8-fold) and E5 (1.8-fold) elements, but not at the MYC promoter, N-ME and BDME E1, E2 and E4 (FIG. 5B). Enhanced RUNX1 peaks at the three elements, but not at N-ME, were also observed in human primary inv(16) AML samples (FIG. 5C).

Figure 14:
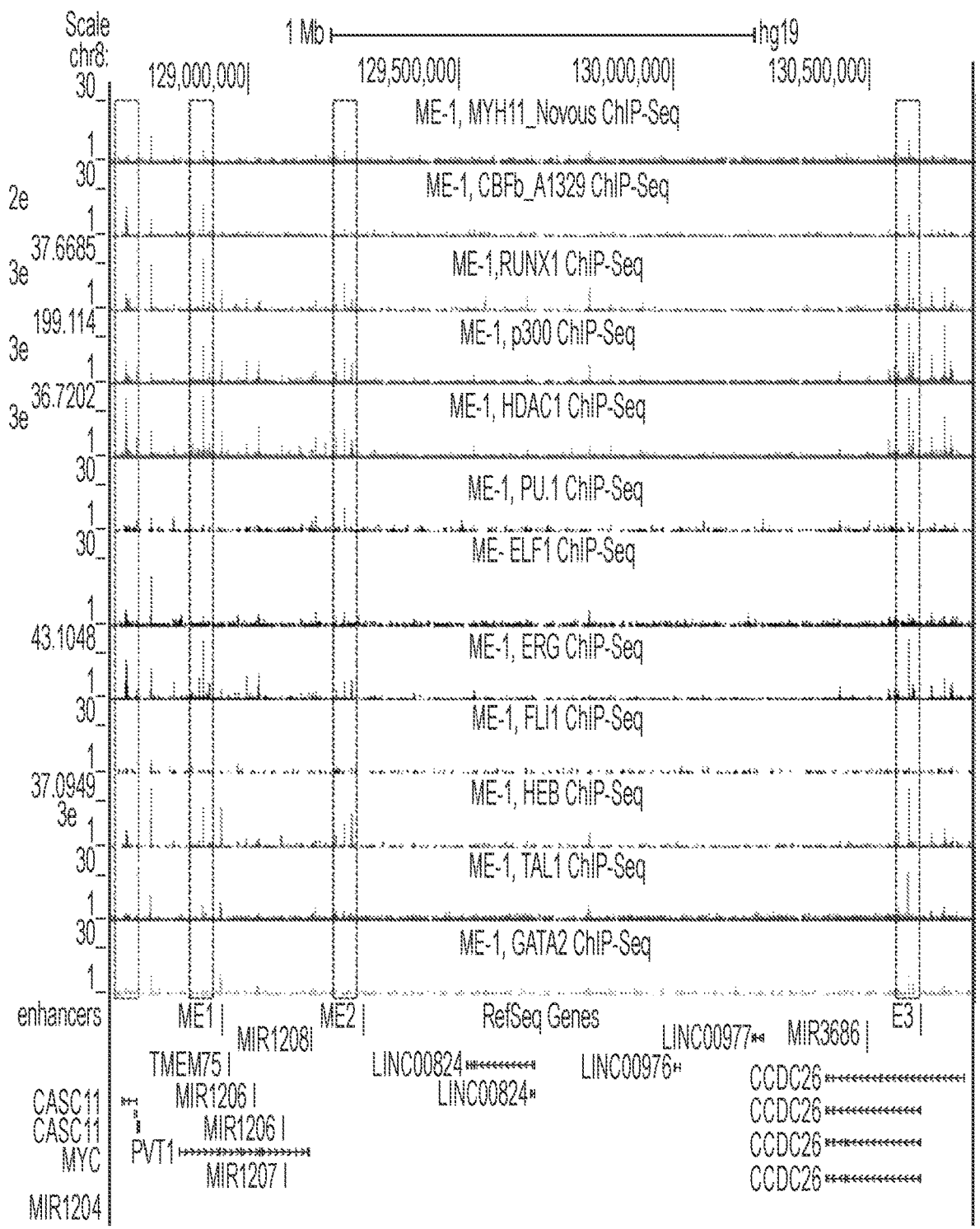
FIG. 14 shows analysis of transcription factor ChIP-Seq at MYC Locus. Transcription factor ChIP-seq analysis is from GEO: GSE46044 (Mandoli et al., 2014) at the 2 Mb downstream of the MYC TSS. Peak location for MYC promoter (blue) and ME1, ME2 and E3 (black) are shown as dotted line windows.

In order to further investigate the activity of ME1, ME2 and E3 elements in inv(16) AML, the transcription factor binding profile downstream of MYC, previously reported in ME-1 cells (Mandoli et al., 2014) was analyzed. The presence of RUNX1 peaks at the three sites was confirmed, and it was determined that RUNX1 co-factors p300, HDAC1 and the E-box transcription factor HEB were also found at ME1, ME2 and E3 (FIG. 14). These data further support the enhancer activity of ME1, ME2 and E3 in inv(16) AML cells, and the association of RUNX1 complexes.

Example 6: The ME1, ME2 and E3 enhancers physically interact with the MYC promoter. A critical determinant of enhancer activity in the regulation of MYC expression is the identification of physical interactions between regulatory elements. Considering that distant MYC enhancers have been reported up and downstream of MYC in a variety of cancers, the DNA interactions in a 4 Mb region around the MYC locus, including 1 Mb upstream and 3 Mb downstream of the MYC TSS, were analyzed utilizing chromosome conformation capture carbon copy (5C; (Dostie et al., 2006)) in ME-1 cells treated with DMSO or AI-10-49 for six hours. Chromatin interaction maps for this region showed the presence of a series of Topologically Associating Domains (TADs; (Dixon et al., 2012; Nora et al., 2012)). TADs are contiguous regions with generally elevated interaction frequencies separated by boundaries (FIG. 6A, arrows) that often contain CTCF bound sites across which fewer interactions occur. The MYC gene is located near the left boundary of a large TAD that contains several subregions, one that contains the ME1 and ME2 enhancer, and another that contains the BDME superenhancer encompassing CTCF sites and E3/E5. The interactions of the MYC promoter were analyzed in more detail by plotting the 5C interaction frequency of the promoter with the entire domain in a 4C-style interaction plot (FIG. 6B). Interaction frequencies generally decrease as function of genomic distance, as expected. Several peaks superimposed on this general trend were observed, representing specific looping interactions (Dekker et al., 2013). A significant interaction of the MYC promoter with ME1, ME2, and the BDME superenhancer was identified. Within the superenhancer, three peaks of elevated interactions were also identified, the two strongest of which contain CTCF binding sites (FIG. 6B, arrowheads). These interactions may involve interactions between the superenhancer and CTCF sites near the MYC promoter. In addition, a local peak of interactions is observed between the MYC promoter and the E3/E5 enhancer. These results were confirmed by plotting interactions between ME1, ME2 and E3 and the entire domain (FIG. 6B), which showed that all these elements interact with each other. Two loci located between ME1 and ME2 also interact with these elements (FIG. 6B, arrows), and these coincide with sites of open chromatin and H3K27Ac but not with RUNX1 peaks (FIG. 5A), suggesting the presence of additional functional elements with local interactions. These experiments provide critical evidence that the MYC promoter physically interacts with RUNX1-associated enhancers ME1, ME2 and E3 in inv(16) AML cells. Furthermore, these distal elements also physically interact with each other.

Figure 6A:
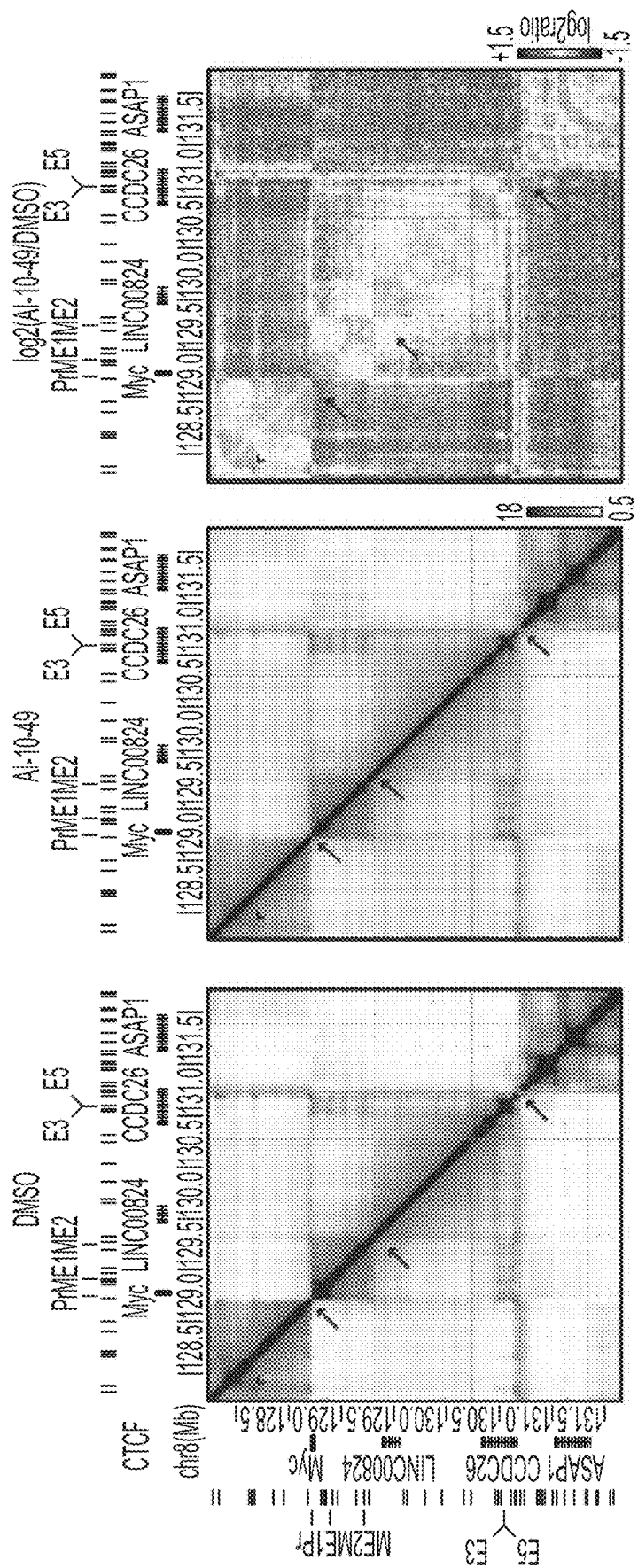
FIG. 6 (A-B) shows long-range DNA interaction analysis at the MYC locus. (A) shows 5C interaction matrices for the MYC locus for ME-1 cells treated for 6 hrs with DMSO (control, left panel) and with AI-10-49 (middle panel). The right panel shows the log$_2$(AI-10-49/DMSO) ratio of the interaction matrices (blue colorscheme: higher interaction frequencies in DMSO treated cells; orange colorscheme: higher interaction frequencies in AI-10-49 treated cells). Arrows indicate TAD boundaries, arrowhead points to an example of a CTCF-CTCF looping interaction. (B) shows 4C-style plots for 15 Kb bins (anchor bins) containing the MYC promoter (Myc-Pr), ME1, ME2, and E3/E5 enhancers for DMSO and AI-10-49 treated cells. Anchor bins are shown in orange, solid black lines represent the LOWESS mean (the expected interaction frequency as a function of genomic distance) and the dotted black lines are the LOWESS plus and minus 1 standard deviation. Red lines are the observed 5C interaction frequencies. Green dots and vertical dotted lines highlight the positions and interactions between Myc-Pr, ME1, ME2, and E3. Arrowheads indicate interactions with CTCF sites around the BDME superenhancer. Arrows indicate peaks of interactions pointing to loci interacting with Myc-Pr, ME1, ME2, and E3. The CTCF binding data were used from ChIP-seq data previously reported in K562 cells (GSE70764; (Pugacheva et al., 2015)).
Figure 6B:
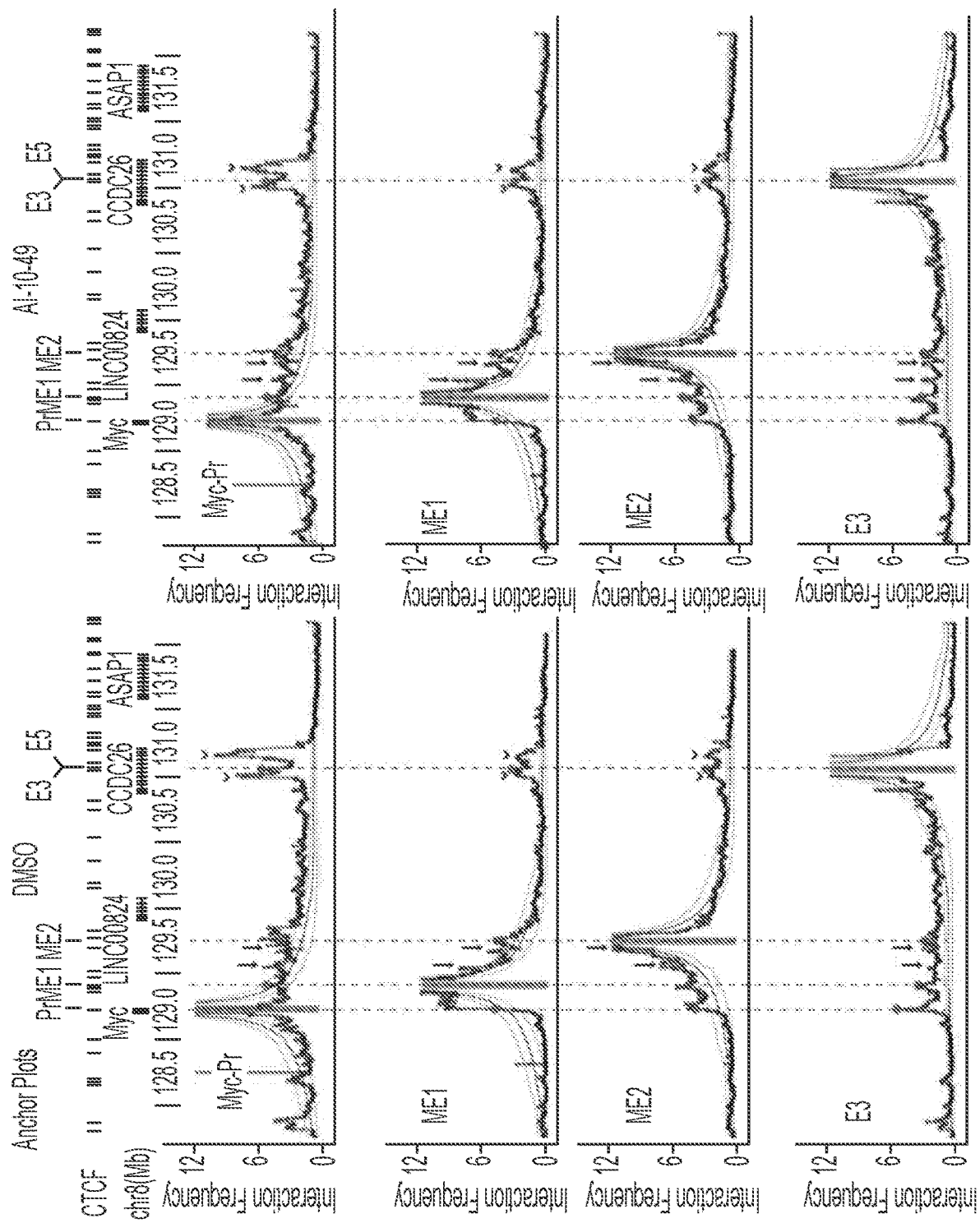

In AI-10-49 treated cells the overall conformation of the region was not altered (FIG. 6A, left and middle panels). However, quantitative differences were observed. First, when plotting the ratio of the interactions maps obtained with AI-10-49 treated cells and control cells, elevated interactions between loci located in adjacent TADs (FIG. 6A, right panel) were observed, indicating a weakening of the strength of TAD boundaries. This may be the result of a modest reduction in G1 cells in AI-10-49 treated cultures. Second, the interactions among the MYC promoter, ME1, ME2 and E3 appeared more prominent, while the interactions between the MYC promoter and the other elements of the BDME superenhancer, containing sites bound by CTCF, were reduced. These experiments provide critical evidence that the MYC promoter physically interacts with enhancers showing increased RUNX1 occupancy in inv(16) AML cells.

Figures 7A, 7B:
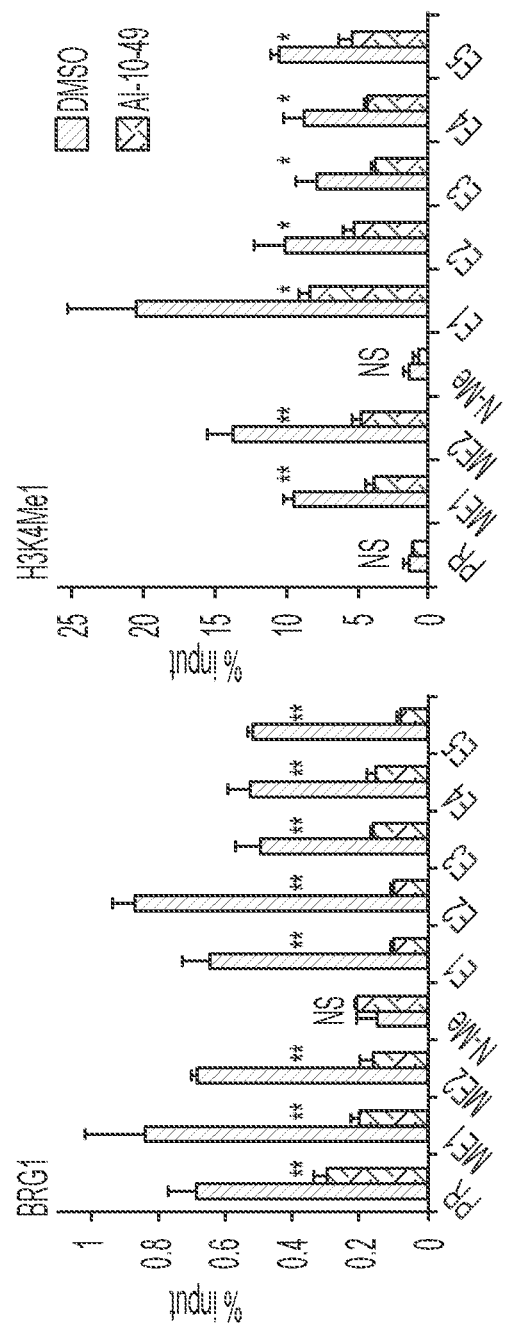
FIG. 7(A-H) shows that AI-10-49 replaces activation for repressive marks at RUNX1 associated MYC enhancers. (A and B) show ChIP-qPCR analysis of treated ME-1 cells at the promoter (PR) and eight MYC enhancers (ME1, ME2, N-Me, and BDME elements E1 to E5) for BRG1 (A) and H3K4me1 (B). (C) shows MYC transcript level analysis in ME-1 cells transduced with scramble (Scr) or SMARCA4 shRNAs (sh3 and sh4), estimated by qRT-PCR. (D and E) show ChIP-qPCR analysis of treated ME-1 cells at MYC promoter and MYC enhancers for RING1B (D) and H3K27Me3 mark (E). (F) shows MYC transcript level analysis in ME-1 cells transduced with scramble (Scr) or RNF2 shRNAs (sh2 and sh4) and treated with DMSO (D) or AI-10-49 (49), estimated by qRT-PCR. (G) is a time-course ChIP-qPCR analysis of RUNX1, RING1B, and BRG1 binding at E3 in treated ME-1. (H) is a quantitative ChIP-re-ChIP of treated ME-1 ChIPed for RUNX1 or immunoglobulinG (IgG) and re-ChIPed for IgG (red), RING1B (violet), or BRG1 (blue), at the E3 enhancer. Results from triplicate experiments are shown; error bars represent SD. Significance was calculated using unpaired t test; *$p<0.05$ or **$p<0.005$.
Figure 15A:
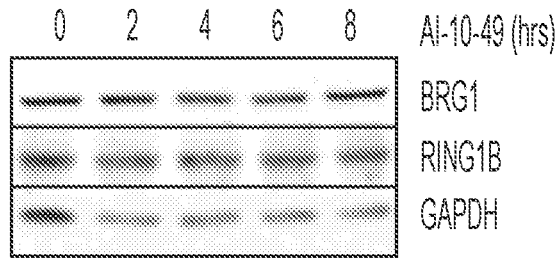
FIG. 15(A-E) shows AI-10-49 replaces activation for repressive marks at RUNX1 associated MYC enhancers. (A) shows an immunoblot analysis for BRG1, RING1B and GAPDH in lysates of ME-1 cells treated with 1 mM AI-10-49 at 2 to 8 hr. (B and C) show qRT-PCR analysis of SMARCA4 (B) and RNF2 (C) transcript levels in ME-1 cells transduced with scramble (Scr) or two gene specific shRNAs. Results from triplicate experiments shown; error bars represent the SD. (D) is an evaluation of MYC transcript levels in ME-1 cells treated with RING1B inhibitor PRT 4165 for 8 days followed by treatment with DMSO/AI-10-49 (0.6 mM) for 6 hr, and MYC relative expression levels (REL) were estimated using qRT-PCR. Results from triplicate experiments shown; error bars represent the SD. (E) shows co-immunoprecipitation analysis of RUNX1 binding to BRG1 and RING1B in nuclear extracts from ME-1 cells treated with DMSO/AI-10-49 for 6 hr. Significance was calculated as unpaired t test (B-D).
Figure 15B:
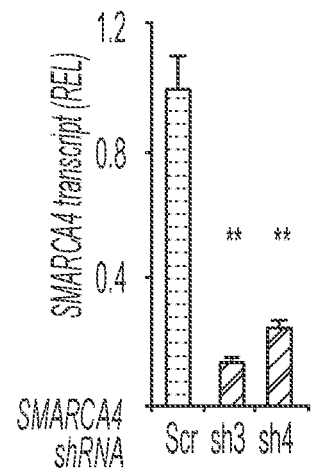
Figure 15C:
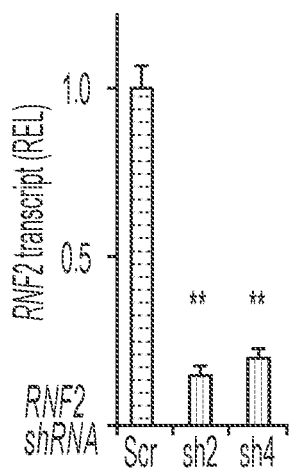
Figure 15D:
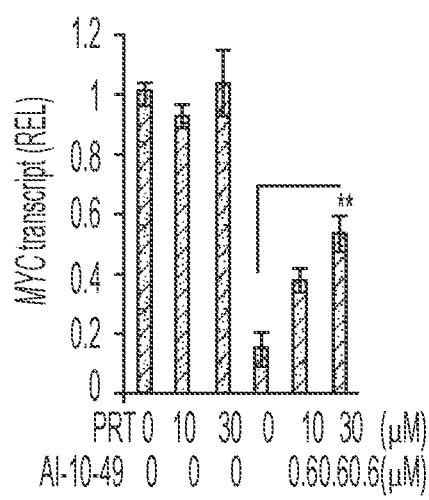

Example 7: AI-10-49 induces a switch of SWI-SNF active complexes to PRC repressive complexes at the AML-Associated MYC Enhancers. It was hypothesized that increase in RUNX1 peaks may alter the active chromatin complexes at these enhancers. Therefore, AI-10-49-mediated changes in BRG1, a component of the SWI/SNF complex that participates in BDME-mediated MYC expression (Shi et al., 2013) was assessed. ChIP-qPCR analysis in ME-1 cells revealed that BRG1 is displaced from the MYC promoter and ME1, ME2, and BDME regulatory elements (FIG. 7A) whereas total BRG1 levels were not altered (FIG. 15A). In addition, ChIP-PCR analysis for changes in Histone 3 Lys 4 monomethylation (H3K4me1), an active enhancer-specific histone mark (Loven et al., 2013), also revealed a significant reduction in ME1, ME2 and ME3 enhancers, but not at N-ME and MYC promoter (FIG. 7B). These results revealed pharmacologic inhibition of CBFβ-SMMHC activity led to the removal of SWI/SNF activating complexes in the MYC distal enhancers.

Figure 7D:
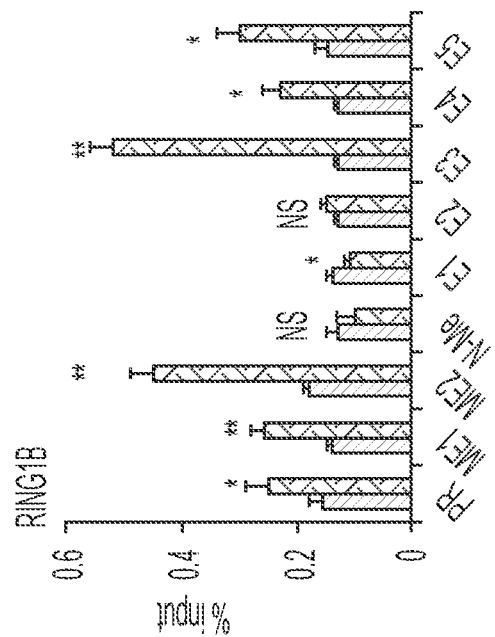
Figure 7C:
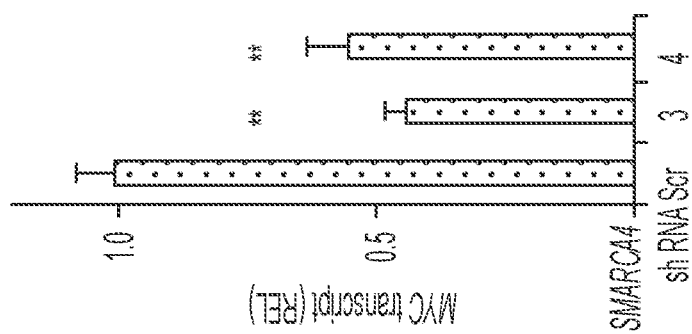
Figure 7F:
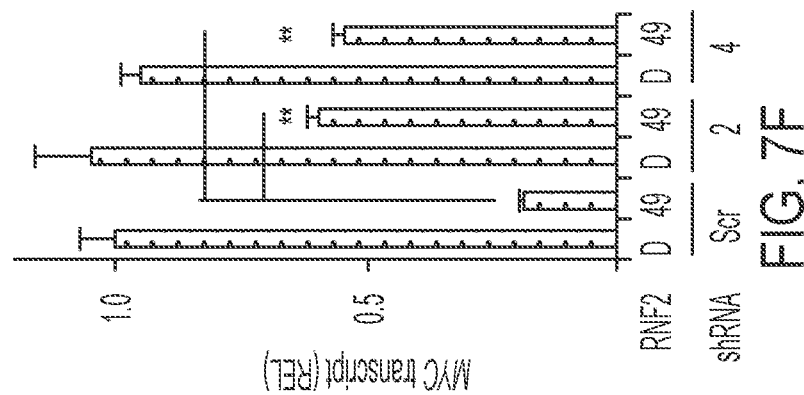
Figure 15E:
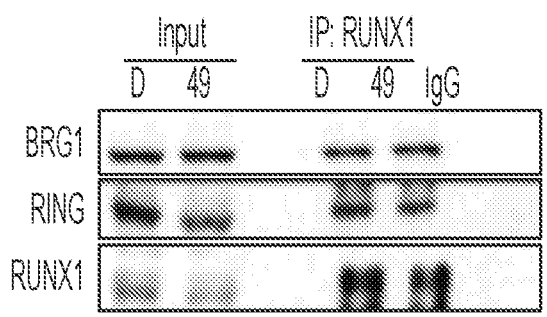

The combined activity of polycomb-repressive protein complexes PRC1 and PRC2 at the enhancers can instill gene silencing by tri-methylation of lysine 27 of histone H3 (H3K27me3) and histone H2 lysine 119 ubiquitination (H2K119ub; (Blackledge et al., 2015)). Considering that RUNX1 recruits the PRC1 subunit RING1B to the chromatin during hematopoietic differentiation (Ross et al., 2012; Yu et al., 2012), it was hypothesized that RUNX1 may induce PRC1 association with chromatin in inv(16) AML cells. Therefore, whether features associated with repressive chromatin, including RING1B and H3K27me3, were modified by AI-10-49 at the MYC locus, was evaluated. ChIP-qPCR analysis revealed that RING1B is specifically recruited to the RUNX1 bound enhancers, ME1, ME2 and E3 but not at N-ME (FIG. 7D). To define the dynamics of chromatin complex replacement associated with AI-10-49 treatment in inv(16) AML, a time-course ChIP-qPCR for RUNX1, RING1B, and BRG1 at E3 in AI-10-49-treated ME-1 cells (FIG. 7G) was performed. RUNX1 and RING1B binding showed a similar pattern, increasing at approximately 2.5 hr, and reaching 90% occupancy by 5 hr. Conversely, BRG1 binding was reduced between 4 and 6 hr of treatment. The observed delay between RUNX1/RING1B occupancy and the reduction in BRG1 at E3 supports a complex replacement model. In addition, the interaction between RUNX1 and BRG1 or RING1B at E3, was evaluated utilizing ChIP-re-ChIP technique. This analysis revealed that RUNX1 specifically interacts with RING1B, but not with BRG1 at E3, and that this interaction is induced by AI-10-49 treatment (FIG. 6H). Furthermore, co-immunoprecipitation analysis of ME-1 nuclear lysates confirmed that RUNX1 can bind to BRG1 and to RING1B (FIG. 15E). These results indicate that AI-10-49 induces RUNX1-mediated repression of MYC expression by RUNX1-directed recruitment of PRC-repressive complexes to the MYC enhancers, thereby evicting the SWI/SNF activating complexes. Furthermore, these results suggest that RUNX1 interactions with chromatin complexes may be locus specific.

Figure 7E:
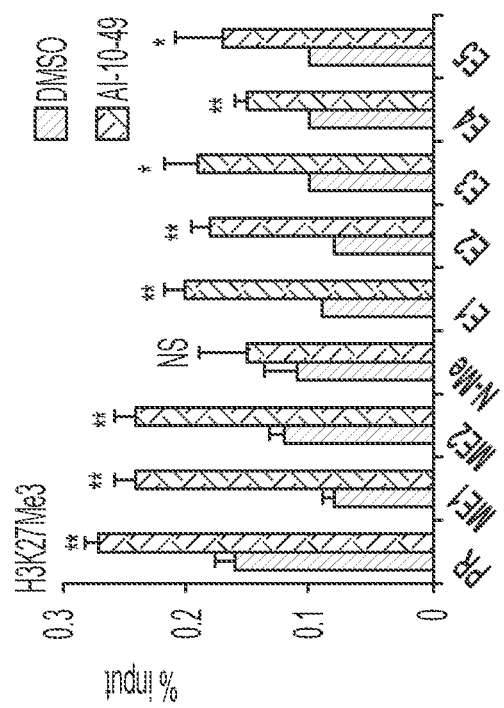

Since PRC1 contributes to PRC2 recruitment, AI-10-49 treatment of ME-1 cells was investigated for whether it could affect the H3K27me3 mark at these sites. ChIP-qPCR experiments revealed a significant increase in H3K27me3 associations at the enhancer elements, except for N-ME (FIG. 7E). These results suggest that AI-10-49 may induce RUNX1-mediated repression of MYC expression by interfering with SWI/SNF complexes and recruiting PRC-repressive complexes to the inv(16) AML-associated MYC enhancers.

Figure 8A:
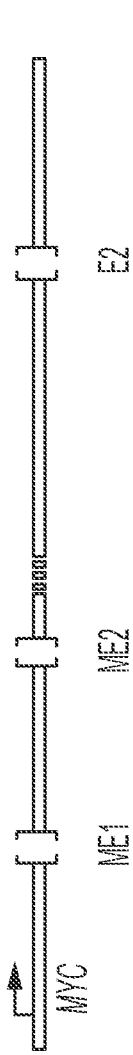
FIG. 8(A-C) shows deletion of three RUNX1-associated MYC enhancer elements impairs MYC expression and viability of inv(16) AML. (A) is a schematic of CRISPR/Cas9 mediated deletion of MYC enhancer elements (top), and frequency estimates by sequencing of major deletion (del), deletions with lost RUNX1 binding site (RBS), and wild type (wt) alleles at each element (bottom) 48 hrs after sorting of sgRNA/Cas9 transfected ME-1 cells. (B) shows MYC expression by qRT-PCR in ME-1 cells. (C) shows viability (7AAD$^-$, Annexin V$^-$) of ME-1 cells 14 days after sorting. Results from triplicate experiments shown; error bars represent the SD. For panel B, significance was calculated as unpaired t-test, $P<0.005$. For panel C, significance was calculated as Levene's test, $P<0.005$.
Figure 8C:
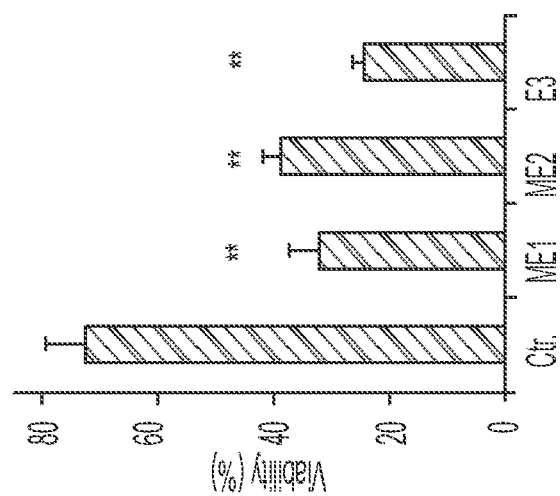
Figure 8B:
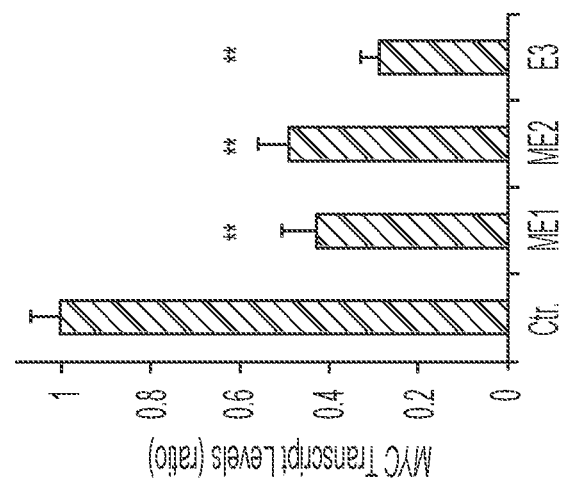
Figure 16A:
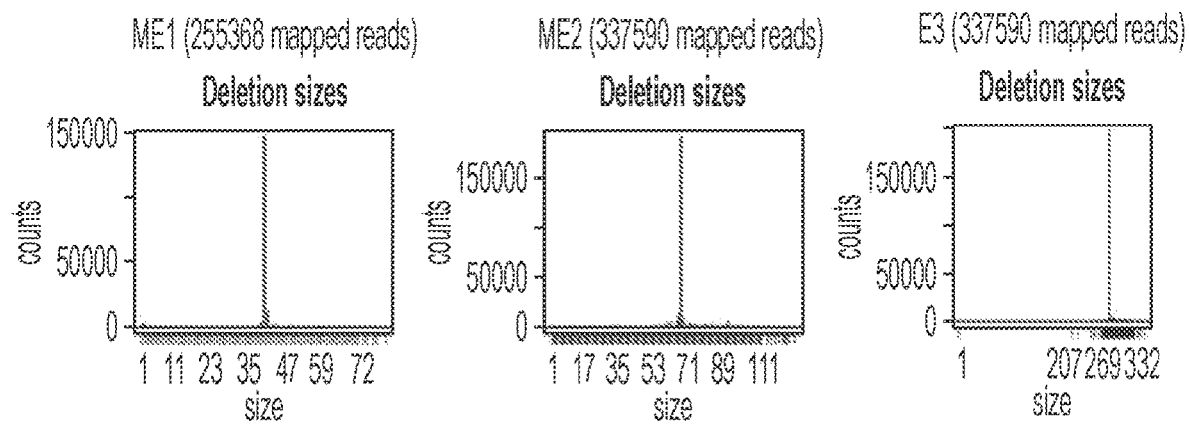
FIG. 16(A-D) shows sequence analysis of deletions (A) by size and (B) by location, in inv(16) AML ME-1 cells treated with CRISPR-Cas9 and sgRNAs for ME1, ME2 and E3. Analysis performed utilizing CRISPR Genome Analyzer (Guell et al., 2014). (C) shows analysis of deletions for N-Me; (D) shows analysis by location for N-Me.
Figure 16B:
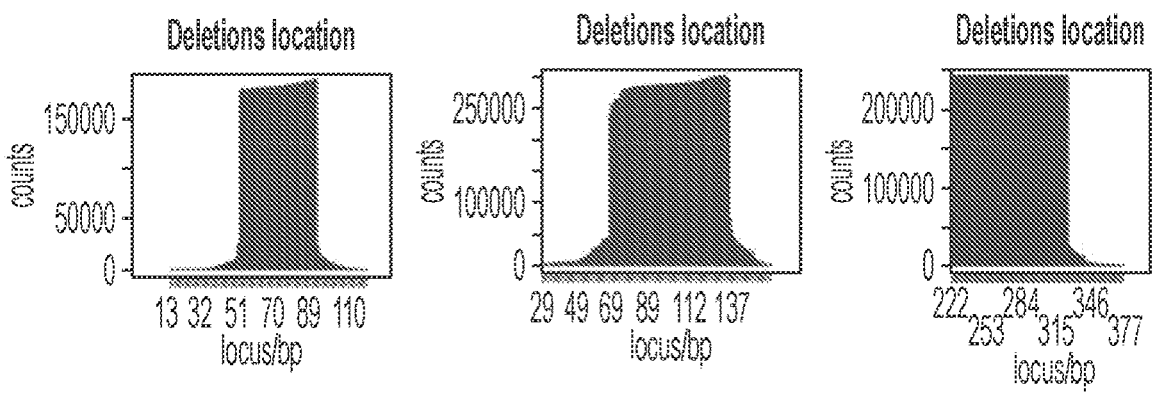
Figure 16C:
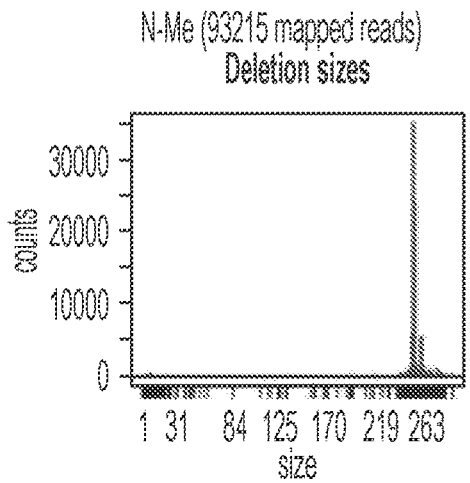
Figure 16D:
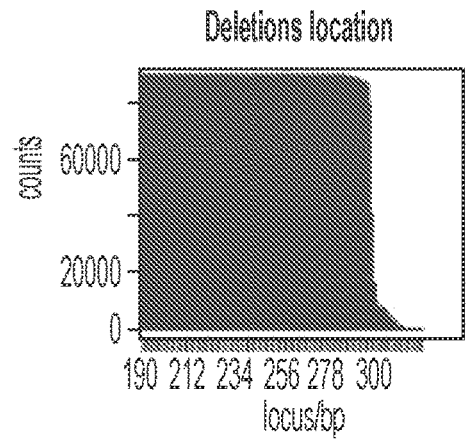

Example 8. MYC expression and viability of inv(16) AML cells depend on the activity of three distal enhancers ME1, ME2 and BDME-E3. To establish the functional significance of the three enhancers identified in inv(16) AML cells, a single deletion of each enhancer, utilizing CRISPR/Cas9 technology, was evaluated for whether it was sufficient to alter MYC expression and function. Sequence analysis of ME-1 cells transfected with Cas9 and 2 sgRNAs for each enhancer to produce small deletions surrounding the RUNX1 binding sites within the enhancers, revealed that the most frequent deletions were of 41 bp (ME1), 67 bp (ME2) and 295 bp (E3) in 60% to 70% of the cells (FIGS. 8A and 16A). The overall frequency of alleles with mutated consensus RUNX binding site (RBS) ranged between 74% and 93%. The individual deletion of these sequences within ME1, ME2 and E3 enhancer elements resulted in 40%-50% reduction in MYC expression (FIG. 8B). Concordantly, cell viability 14 days after sorting was reduced 60% to 70% (FIG. 8C). Taken together, these data demonstrate that ME1, ME2 and E3 function as enhancers to maintain MYC expression levels and the viability of inv(16) AML cells.

Pharmacologic, genomic, biochemical and genetic approaches demonstrate that acute release of the RUNX1 transcription factor alters positioning of chromatin remodeling complexes at MYC distal enhancer elements to induce apoptosis of inv(16) AML cells. CBFβ-SMMHC maintains MYC expression and cell survival, and that this function is RUNX1-dependent. The fusion protein may have RUNX1-dependent or independent functions in hematopoiesis and AML (Hyde et al., 2010; Kamikubo et al., 2010; Mandoli et al., 2014), but the mechanisms underlying CBFβ-SMMHC oncogenic function in leukemia maintenance remains elusive. In inv(16) AML cells, the fusion protein makes most of RUNX1 inaccessible to chromatin (Kanno et al., 1998; Lukasik et al., 2002) and only basal levels of RUNX1 are found associated with chromatin. Such basal RUNX1 function seems essential for leukemia maintenance as further repression of RUNX1 induces cell death and delays leukemia latency of Runx1$^{\Delta/\Delta}$, Cbfb$^{+/MYH11}$ mice (Ben-Ami et al., 2013; Hyde et al., 2015). The dose dependent oncogenic activity has also been reported for other transcription factors associated with AML, such as C-EBPα and PU.1 (Kirstetter et al., 2008; Rosenbauer et al., 2004). The studies above provide new insights on how effective transcription factor levels can determine leukemia maintenance. RUNX1 expression is not affected by AI-10-49 treatment (Illendula et al., 2015); instead, an acute release of RUNX1 from CBFβ-SMMHC multimers disrupts the regulation of MYC expression and its oncogenic programs with an adverse effect in the leukemia-initiating cells. Although this work reveals that MYC repression is a major consequence of CBFβ-SMMHC inhibition, the above findings of a genome-wide increase in chromatin-associated RUNX1 peaks suggests that other RUNX1-target genes may also be implicated in the deregulation of inv(16) AML leukemia maintenance.

It can also be concluded that RUNX1 represses MYC expression by increasing its occupancy at three downstream enhancers (ME1, ME2 and E3) and promoting the switch of activating to repressing chromatin complexes. The balance between SWI/SNF and PRC epigenetic complexes modulates enhancer activity and oncogenic transformation. SWI/SNF can rapidly evict PRC1 from chromatin, and loss of its ATPase subunit, BRG1, inhibits this function (Stanton et al., 2017). The SWI/SNF complex has oncogenic function in t(9; 11) AML, and BRG1 is associated with the distal BDME super-enhancer to maintain MYC expression (Shi et al., 2013). The BDME super-enhancer (element E3) is also active in inv(16) AML, suggesting that BDME may be a "pan-AML" enhancer as it may function in many AML subtypes. In support of this model, BDME was recently identified in a CRISPR-screen to regulate MYC expression in the t(9:22) myeloblast/erythroid leukemia K562 cell line (Fulco et al., 2016). In addition, MYC expression in inv(16) AML depends on two additional enhancers (ME1 and ME2), which seem to be specific for inv(16) AML as they have not been identified in the other AML subtypes.

Another conclusion from the above studies is that acute RUNX1 release is directly associated with MYC expression in inv(16) AML. Acute increase in RUNX1 peaks at ME1, ME2 and E3 enhancers is correlated with BRG1 depletion, decrease of H3K4me1, and increase in RING1b and H3K27me3 repressive marks. Considering that RUNX1 recruits RING1B to regulatory regions during hematopoietic stem and megakaryocytic differentiation (Ross et al., 2012; Yu et al., 2012), RUNX1 may drive the SWI/SNF-PRC1 switch, bringing PRC1 complexes to the MYC-associated enhancers and inducing apoptosis of inv(16) AML cells. Two lines of evidence strengthen the direct role of RUNX1 in MYC repression: first, 5-C assays validated the physical looping of ME1, ME2 and E3 with the MYC promoter in inv(16) AML cells; and second, individual CRISPR-deletion of small intervals including the RUNX1 binding sites in each of these enhancers is sufficient to reduce MYC expression and induce apoptosis.

The above studies provide unique insights about the dynamic balance between transcription factor function and chromatin remodeling complexes in leukemia that need to be addressed. First, targeted inhibitors of transcription factor function may present a unique paradigm in cancer treatment. As it is remarkable that acute RUNX1 release can trigger SWI/SNF to PRC1 switch and eliminate leukemia initiating cells, it resembles H3K27Ac changes due to acute changes in NOTCH levels (Wang et al., 2014; Yashiro-Ohtani et al., 2014) in T-cell acute lymphoblastic leukemia. Second, our current understanding is that SWI-SNF activity is BRG1-dependent, and that it evicts PRC1 from active chromatin elements. As this study places RUNX1 as a mediator of this switch, mechanistic studies are necessary to determine whether acute RUNX1 occupancy directly interferes with SWI/SNF displacing BRG1 and the available enhancer is then occupied by PRC1, or if RUNX1/RING1B complex displaces the active SWI/SNF complex. Third, the above findings have direct therapeutic implications for the design of combination treatments with inhibitors that target leukemia-associated transcription factors and components of chromatin activity. In addition, it suggests that targeted therapies, such as AI-10-49, may also be effective in combination with other inhibitors of components associated with chromatin remodeling complexes. Finally, the above studies suggest that pharmacologic deregulation of RUNX1 function may be therapeutically efficacious in other AML subtypes.

In conclusion, this study demonstrates that the oncoprotein CBFβ-SMMHC sustains the viability of inv(16) AML cells by maintaining active chromatin complexes at three enhancer elements to sustain MYC expression, and that acute disruption of CBFβ-SMMHC/RUNX1 interaction promotes a switch of chromatin complexes within the MYC locus, resulting in MYC downregulation, and RUNX1-dependent apoptosis.

REFERENCES

Alqahtani et al., Bromodomain and extra-terminal motif inhibitors: a review of preclinical and clinical advances in cancer therapy. Future Sci. OA (2019) 5(3), FSO372.

Ben-Ami, O., Friedman, D., Leshkowitz, D., Goldenberg, D., Orlovsky, K., Pencovich, N., Lotem, J., Tanay, A., and Groner, Y. (2013). Addiction of t(8; 21) and inv(16) acute myeloid leukemia to native RUNX1. Cell Rep 4, 1131-1143.

Blackledge, N. P., Rose, N. R., and Klose, R. J. (2015). Targeting Polycomb systems to regulate gene expression: modifications to a complex story. Nature reviews Molecular cell biology 16, 643-649.

Blobel, G. A., Kalota, A., Sanchez, P. V., and Carroll, M. (2011). Short hairpin RNA screen reveals bromodomain proteins as novel targets in acute myeloid leukemia. Cancer Cell 20, 287-288.

Blyth, K., Cameron, E. R., and Neil, J. C. (2005). The RUNX genes: gain or loss of function in cancer. Nat Rev Cancer 5, 376-387.

Buenrostro, J. D., Giresi, P. G., Zaba, L. C., Chang, H. Y., and Greenleaf, W. J. (2013). Transposition of native chromatin for fast and sensitive epigenomic profiling of open chromatin, DNA-binding proteins and nucleosome position. Nature methods 10, 1213-1218.

Buenrostro, J. D., Wu, B., Chang, H. Y., and Greenleaf, W. J. (2015). ATAC-seq: A Method for Assaying Chromatin Accessibility Genome-Wide. Curr Protoc Mol Biol 109, 21 29 21-29.

Cao, Q., Gearhart, M. D., Gery, S., Shojaee, S., Yang, H., Sun, H., Lin, D. C., Bai, J. W., Mead, M., Zhao, Z., et al. (2016). BCOR regulates myeloid cell proliferation and differentiation. Leukemia 30, 1155-1165.

Cao, W., Britos-Bray, M., Claxton, D. F., Kelley, C. A., Speck, N. A., Liu, P. P., and Friedman, A. D. (1997). CBF beta-SMMHC, expressed in M4Eo AML, reduced CBF DNA-binding and inhibited the G1 to S cell cycle transition at the restriction point in myeloid and lymphoid cells. Oncogene 15, 1315-1327.

Castilla, L. H., Garrett, L., Adya, N., Orlic, D., Dutra, A., Anderson, S., Owens, J., Eckhaus, M., Bodine, D., and Liu, P. P. (1999). The fusion gene Cbfb-MYH11 blocks myeloid differentiation and predisposes mice to acute myelomonocytic leukaemia. Nature Genetics 23, 144-146.

Castilla, L. H., Wijmenga, C., Wang, Q., Stacy, T., Speck, N. A., Eckhaus, M., Marin-Padilla, M., Collins, F. S., Wynshaw-Boris, A., and Liu, P. P. (1996). Failure of embryonic hematopoiesis and lethal hemorrhages in mouse embryos heterozygous for a knocked-in leukemia gene CBFβ-MYH11. Cell 87, 687-696.

Chou, T. C. (2010). Drug combination studies and their synergy quantification using the Chou-Talalay method. Cancer Res 70, 440-446.

Dawson, M. A., Prinjha, R. K., Dittmann, A., Giotopoulos, G., Bantscheff, M., Chan, W. I., Robson, S. C., Chung, C. W., Hopf, C., Savitski, M. M., et al. (2011). Inhibition of BET recruitment to chromatin as an effective treatment for MLL-fusion leukaemia. Nature 478, 529-533.

de Alboran, I. M., O'Hagan, R. C., Gartner, F., Malynn, B., Davidson, L., Rickert, R., Rajewsky, K., DePinho, R. A., and Alt, F. W. (2001). Analysis of C-MYC function in normal cells via conditional gene-targeted mutation. Immunity 14, 45-55.

Dekker, J., Marti-Renom, M. A., and Mirny, L. A. (2013). Exploring the three-dimensional organization of genomes: interpreting chromatin interaction data. Nat Rev Genet 14, 390-403.

Delmore, J. E., Issa, G. C., Lemieux, M. E., Rahl, P. B., Shi, J., Jacobs, H. M., Kastritis, E., Gilpatrick, T., Paranal, R. M., Qi, J., et al. (2011). BET bromodomain inhibition as a therapeutic strategy to target c-Myc. Cell 146, 904-917.

Di Croce, L., and Helin, K. (2013). Transcriptional regulation by Polycomb group proteins. Nat Struct Mol Biol 20, 1147-1155.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Dostie, J., Richmond, T. A., Arnaout, R. A., Selzer, R. R., Lee, W. L., Honan, T. A., Rubio, E. D., Krumm, A., Lamb, J., Nusbaum, C., et al. (2006). Chromosome Conformation Capture Carbon Copy (5C): a massively parallel solution for mapping interactions between genomic elements. Genome research 16, 1299-1309.

Douglas, N. C., Jacobs, H., Bothwell, A. L., and Hayday, A. C. (2001). Defining the specific physiological requirements for c-Myc in T cell development. Nat Immunol 2, 307-315.

Durst, K. L., and Hiebert, S. W. (2004). Role of RUNX family members in transcriptional repression and gene silencing. Oncogene 23, 4220-4224.

Ferraiuolo, M. A., Sanyal, A., Naumova, N., Dekker, J., and Dostie, J. (2012). From cells to chromatin: capturing snapshots of genome organization with 5C technology. Methods 58, 255-267.

Fulco, C. P., Munschauer, M., Anyoha, R., Munson, G., Grossman, S. R., Perez, E. M., Kane, M., Cleary, B., Lander, E. S., and Engreitz, J. M. (2016). Systematic mapping of functional enhancer-promoter connections with CRISPR interference. Science 354, 769-773.

Gowda, S. D., Koler, R. D., and Bagby, G. C., Jr. (1986). Regulation of C-myc expression during growth and differentiation of normal and leukemic human myeloid progenitor cells. J Clin Invest 77, 271-278.

Guell, M., Yang, L., and Church, G. M. (2014). Genome editing assessment using CRISPR Genome Analyzer (CRISPR-GA). Bioinformatics 30, 2968-2970.

Guo, H., and Friedman, A. D. (2011). Phosphorylation of RUNX1 by cyclin-dependent kinase reduces direct interaction with HDAC1 and HDAC3. J Biol Chem 286, 208-215.

Guo, Y., Niu, C., Breslin, P., Tang, M., Zhang, S., Wei, W., Kini, A. R., Paner, G. P., Alkan, S., Morris, S. W., et al. (2009). c-Myc-mediated control of cell fate in megakaryocyte-erythrocyte progenitors. Blood 114, 2097-2106.

Herranz, D., Ambesi-Impiombato, A., Palomero, T., Schnell, S. A., Belver, L., Wendorff, A. A., Xu, L., Castillo-Martin, M., Llobet-Navas, D., Cordon-Cardo, C., et al. (2014). A NOTCH1-driven MYC enhancer promotes T cell development, transformation and acute lymphoblastic leukemia. Nature medicine 20, 1130-1137.

Hnisz, D., Abraham, B. J., Lee, T. I., Lau, A., Saint-Andre, V., Sigova, A. A., Hoke, H. A., and Young, R. A. (2013). Super-enhancers in the control of cell identity and disease. Cell 155, 934-947.

Hnisz, D., Weintraub, A. S., Day, D. S., Valton, A. L., Bak, R. O., Li, C. H., Goldmann, J., Lajoie, B. R., Fan, Z. P., Sigova, A. A., et al. (2016). Activation of proto-oncogenes by disruption of chromosome neighborhoods. Science 351, 1454-1458.

Holt, J. T., Redner, R. L., and Nienhuis, A. W. (1988). An oligomer complementary to c-myc mRNA inhibits proliferation of HL-60 promyelocytic cells and induces differentiation. Mol Cell Biol 8, 963-973.

Hoogenkamp, M., Lichtinger, M., Krysinska, H., Lancrin, C., Clarke, D., Williamson, A., Mazzarella, L., Ingram, R., Jorgensen, H., Fisher, A., et al. (2009). Early chromatin unfolding by RUNX1: a molecular explanation for differential requirements during specification versus maintenance of the hematopoietic gene expression program. Blood 114, 299-309.

Huber, W., Carey, V. J., Gentleman, R., Anders, S., Carlson, M., Carvalho, B. S., Bravo, H. C., Davis, S., Gatto, L., Girke, T., et al. (2015). Orchestrating high-throughput genomic analysis with Bioconductor. Nat Meth 12, 115-121.

Hyde, R. K., Kamikubo, Y., Anderson, S., Kirby, M., Alemu, L., Zhao, L., and Liu, P. P. (2010). Cbfb/Runx1 repression-independent blockage of differentiation and accumulation of Csf2rb-expressing cells by Cbfb-MYH11. Blood 115, 1433-1443.

Hyde, R. K., Zhao, L., Alemu, L., and Liu, P. P. (2015). Runx1 is required for hematopoietic defects and leukemogenesis in Cbfb-MYH11 knock-in mice. Leukemia 29, 1771-1778.

Ihaka, R., and Gentleman, R. (1996). R: A language for data analysis and graphics. J Comput Graph Stat 5, 5.

Illendula, A., Pulikkan, J. A., Zong, H., Grembecka, J., Xue, L., Sen, S., Zhou, Y., Boulton, A., Kuntimaddi, A., Gao, Y., et al. (2015). Chemical biology. A small-molecule inhibitor of the aberrant transcription factor CBFbeta-SMMHC delays leukemia in mice. Science 347, 779-784.

Imakaev, M., Fudenberg, G., McCord, R. P., Naumova, N., Goloborodko, A., Lajoie, B. R., Dekker, J., and Mirny, L. A. (2012). Iterative correction of Hi-C data reveals hallmarks of chromosome organization. Nature methods 9, 999-1003.

Johansen, L. M., Iwama, A., Lodie, T. A., Sasaki, K., Felsher, D. W., Golub, T. R., and Tenen, D. G. (2001). c-Myc is a critical target for c/EBPalpha in granulopoiesis. Mol Cell Biol 21, 3789-3806.

Kadoch, C., and Crabtree, G. R. (2015). Mammalian SWI/SNF chromatin remodeling complexes and cancer: Mechanistic insights gained from human genomics. Sci Adv 1, e1500447.

Kamikubo, Y., Zhao, L., Wunderlich, M., Corpora, T., Hyde, R. K., Paul, T. A., Kundu, M., Garrett, L., Compton, S., Huang, G., et al. (2010). Accelerated leukemogenesis by truncated CBF beta-SMMHC defective in high-affinity binding with RUNX1. Cancer Cell 17, 455-468.

Kanno, Y., Kanno, T., Sakakura, C., Bae, S. C., and Ito, Y. (1998). Cytoplasmic sequestration of the polyomavirus enhancer binding protein 2 (PEBP2)/core binding factor alpha (CBFalpha) subunit by the leukemia-related PEBP2/CBFbeta-SMMHC fusion protein inhibits PEBP2/CBF-mediated transactivation. Mol Cell Biol 18, 4252-4261.

Kiessling, L. L., J. E. Gestwicki, et al., (2006). *Angewandte Chemie-International Edition* 45(15): 2348-2368.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome biology 14, R36.

Kirstetter, P., Schuster, M. B., Bereshchenko, O., Moore, S., Dvinge, H., Kurz, E., Theilgaard-Monch, K., Mansson, R., Pedersen, T. A., Pabst, T., et al. (2008). Modeling of C/EBPalpha mutant acute myeloid leukemia reveals a common expression signature of committed myeloid leukemia-initiating cells. Cancer Cell 13, 299-310.

Kitabayashi, I., Aikawa, Y., Nguyen, L. A., Yokoyama, A., and Ohki, M. (2001). Activation of AML1-mediated transcription by MOZ and inhibition by the MOZ-CBP fusion protein. EMBO J 20, 7184-7196.

Kitabayashi, I., Yokoyama, A., Shimizu, K., and Ohki, M. (1998). Interaction and functional cooperation of the leukemia-associated factors AML1 and p300 in myeloid cell differentiation. EMBO J 17, 2994-3004.

Kress, T. R., Sabo, A., and Amati, B. (2015). MYC: connecting selective transcriptional control to global RNA production. Nat Rev Cancer 15, 593-607.

Kuo, Y. H., Gerstein, R. M., and Castilla, L. H. (2008). Cbfbeta-SMMHC impairs differentiation of common lymphoid progenitors and reveals an essential role for RUNX in early B-cell development. Blood 111, 1543-1551.

Kuo, Y. H., Landrette, S. F., Heilman, S. A., Perrat, P. N., Garrett, L., Liu, P. P., Le Beau, M. M., Kogan, S. C., and Castilla, L. H. (2006). Cbf beta-SMMHC induces distinct abnormal myeloid progenitors able to develop acute myeloid leukemia. Cancer Cell 9, 57-68.

Lajoie, B. R., van Berkum, N. L., Sanyal, A., and Dekker, J. (2009). My5C: web tools for chromosome conformation capture studies. Nature methods 6, 690-691.

Langmead, B., and Salzberg, S. L. (2012). Fast gapped-read alignment with Bowtie 2. Nature methods 9, 357-359.

Lessard, J., and Sauvageau, G. (2003). Bmi-1 determines the proliferative capacity of normal and leukaemic stem cells. Nature 423, 255-260.

Lichtinger, M., Hoogenkamp, M., Krysinska, H., Ingram, R., and Bonifer, C. (2010). Chromatin regulation by RUNX1. Blood Cells Mol Dis 44, 287-290.

Liu, P., Tarle, S. A., Hajra, A., Claxton, D. F., Marlton, P., Freedman, M., Siciliano, M. J., and Collins, F. S. (1993). Fusion between transcription factor CBF beta/PEBP2 beta and a myosin heavy chain in acute myeloid leukemia. Science 261, 1041-1044.

Lorsbach, R. B., Moore, J., Ang, S. O., Sun, W., Lenny, N., and Downing, J. R. (2004). Role of RUNX1 in adult hematopoiesis: analysis of RUNX1-IRES-GFP knock-in mice reveals differential lineage expression. Blood 103, 2522-2529.

Loven, J., Hoke, H. A., Lin, C. Y., Lau, A., Orlando, D. A., Vakoc, C. R., Bradner, J. E., Lee, T. I., and Young, R. A. (2013). Selective inhibition of tumor oncogenes by disruption of super-enhancers. Cell 153, 320-334.

Lukasik, S. M., Zhang, L., Corpora, T., Tomanicek, S., Li, Y., Kundu, M., Hartman, K., Liu, P. P., Laue, T. M., Biltonen, R. L., et al. (2002). Altered affinity of CBF beta-SMMHC for Runx1 explains its role in leukemogenesis. Nat Struct Biol 9, 674-679.

Mammen, M., S. K. Choi, et al., (1998). *Angewandte Chemie-International Edition* 37(20): 2755-2794.

Mandoli, A., Singh, A. A., Jansen, P. W., Wierenga, A. T., Riahi, H., Franci, G., Prange, K., Saeed, S., Vellenga, E., Vermeulen, M., et al. (2014). CBFβ-MYH11/RUNX1 together with a compendium of hematopoietic regulators, chromatin modifiers and basal transcription factors occupies self-renewal genes in inv(16) acute myeloid leukemia. Leukemia 28, 770-778.

Martin, M. (2011). Cutadapt removes adapter sequences from high-throughput sequencing reads. 2011 17.

Mulder, A., T. Auletta, et al., (2004). *Journal of the American Chemical Society* 126(21):6627-6636.

Naumova, N., Smith, E. M., Zhan, Y., and Dekker, J. (2012). Analysis of long-range chromatin interactions using Chromosome Conformation Capture. Methods 58, 192-203.

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

North, T. E., Stacy, T., Matheny, C. J., Speck, N. A., and de Bruijn, M. F. (2004). Runx1 is expressed in adult mouse hematopoietic stem cells and differentiating myeloid and lymphoid cells, but not in maturing erythroid cells. Stem Cells 22, 158-168.

Ou, J., Yu, J., Kelliher, M., Castilla, L., Lawson, N., and Zhu, L. J. (2017). ATAC-seq Quality Control. Bioconductor.

Pencovich, N., Jaschek, R., Tanay, A., and Groner, Y. (2011). Dynamic combinatorial interactions of RUNX1 and cooperating partners regulates megakaryocytic differentiation in cell line models. Blood 117, e1-14.

Pomerantz, M. M., Ahmadiyeh, N., Jia, L., Herman, P., Verzi, M. P., Doddapaneni, H., Beckwith, C. A., Chan, J. A., Hills, A., Davis, M., et al. (2009). The 8q24 cancer risk variant rs6983267 shows long-range interaction with MYC in colorectal cancer. Nat Genet 41, 882-884.

Ptasinska, A., Assi, S. A., Mannari, D., James, S. R., Williamson, D., Dunne, J., Hoogenkamp, M., Wu, M., Care, M., McNeill, H., et al. (2012). Depletion of RUNX1/ETO in t(8; 21) AML cells leads to genome-wide changes in chromatin structure and transcription factor binding. Leukemia 26, 1829-1841.

Pugacheva, E. M., Rivero-Hinojosa, S., Espinoza, C. A., Mendez-Catala, C. F., Kang, S., Suzuki, T., Kosaka-Suzuki, N., Robinson, S., Nagarajan, V., Ye, Z., et al. (2015). Comparative analyses of CTCF and BORIS occupancies uncover two distinct classes of CTCF binding genomic regions. Genome biology 16, 161.

Ramirez, F., Ryan, D. P., Gruning, B., Bhardwaj, V., Kilpert, F., Richter, A. S., Heyne, S., Dundar, F., and Manke, T. (2016). deepTools2: a next generation web server for deep-sequencing data analysis. Nucleic acids research 44, W160-165.

Reed-Inderbitzin, E., Moreno-Miralles, I., Vanden-Eynden, S. K., Xie, J., Lutterbach, B., Durst-Goodwin, K. L., Luce, K. S., Irvin, B. J., Cleary, M. L., Brandt, S. J., et al. (2006). RUNX1 associates with histone deacetylases and SUV39H1 to repress transcription. Oncogene 25, 5777-5786.

Ricci, M. S., Jin, Z., Dews, M., Yu, D., Thomas-Tikhonenko, A., Dicker, D. T., and E I-Deiry, W. S. (2004). Direct repression of FLIP expression by c-myc is a major determinant of TRAIL sensitivity. Mol Cell Biol 24, 8541-8555.

Ritz, C., Baty, F., Streibig, J. C., and Gerhard, D. (2015). Dose-Response Analysis Using R. PloS one 10, e0146021.

Roderick, J. E., Tesell, J., Shultz, L. D., Brehm, M. A., Greiner, D. L., Harris, M. H., Silverman, L. B., Sallan, S. E., Gutierrez, A., Look, A. T., et al. (2014). c-Myc inhibition prevents leukemia initiation in mice and impairs the growth of relapsed and induction failure pediatric T-ALL cells. Blood 123, 1040-1050.

Rosenbauer, F., Wagner, K., Kutok, J. L., Iwasaki, H., Le Beau, M. M., Okuno, Y., Akashi, K., Fiering, S., and Tenen, D. G. (2004). Acute myeloid leukemia induced by graded reduction of a lineage-specific transcription factor, PU.1. Nat Genet 36, 624-630.

Ross, K., Sedello, A. K., Todd, G. P., Paszkowski-Rogacz, M., Bird, A. W., Ding, L., Grinenko, T., Behrens, K., Hubner, N., Mann, M., et al. (2012). Polycomb group ring finger 1 cooperates with Runx1 in regulating differentiation and self-renewal of hematopoietic cells. Blood 119, 4152-4161.

Ross-Innes, C. S., Stark, R., Teschendorff, A. E., Holmes, K. A., Ali, H. R., Dunning, M. J., Brown, G. D., Gojis, O., Ellis, I. O., Green, A. R., et al. (2012). Differential oestrogen receptor binding is associated with clinical outcome in breast cancer. Nature 481, 389-393.

Sanyal, A., Lajoie, B. R., Jain, G., and Dekker, J. (2012). The long-range interaction landscape of gene promoters. Nature 489, 109-113.

Shi, J., Whyte, W. A., Zepeda-Mendoza, C. J., Milazzo, J. P., Shen, C., Roe, J. S., Minder, J. L., Mercan, F., Wang, E., Eckersley-Maslin, M. A., et al. (2013). Role of SWI/SNF in acute leukemia maintenance and enhancer-mediated Myc regulation. Genes Dev 27, 2648-2662.

Shigesada, K., B. van de Sluis, et al., (2004). *Oncogene* 23(24): 4297-307.

Stanton, B. Z., Hodges, C., Calarco, J. P., Braun, S. M., Ku, W. L., Kadoch, C., Zhao, K., and Crabtree, G. R. (2017). Smarca4 ATPase mutations disrupt direct eviction of PRC1 from chromatin. Nat Genet 49, 282-288.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: A knowledge-based approach for interpreting genome-wide expression profiles. Proceedings of the National Academy of Sciences 102, 15545-15550.

Trapnell, C., Pachter, L., and Salzberg, S. L. (2009). TopHat: discovering splice junctions with RNA-Seq. Bioinformatics 25, 1105-1111.

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nat Protoc 7, 562-578.

Trapnell, C., Williams, B. A., Pertea, G., Mortazavi, A., Kwan, G., van Baren, M. J., Salzberg, S. L., Wold, B. J., and Pachter, L. (2010). Transcript assembly and quantification by RNA-Seq reveals unannotated transcripts and isoform switching during cell differentiation. Nat Biotech 28, 511-515.

van der Lugt, N. M., Domen, J., Linders, K., van Roon, M., Robanus-Maandag, E., to Riele, H., van der Valk, M., Deschamps, J., Sofroniew, M., van Lohuizen, M., et al. (1994). Posterior transformation, neurological abnormalities, and severe hematopoietic defects in mice with a targeted deletion of the bmi-1 protooncogene. Genes Dev 8, 757-769.

Vradii, D., Zaidi, S. K., Lian, J. B., van Wijnen, A. J., Stein, J. L., and Stein, G. S. (2005). Point mutation in AML1 disrupts subnuclear targeting, prevents myeloid differentiation, and effects a transformation-like phenotype. Proceedings of the National Academy of Sciences of the United States of America 102, 7174-7179.

Vu, L. P., Perna, F., Wang, L., Voza, F., Figueroa, M. E., Tempst, P., Erdjument-Bromage, H., Gao, R., Chen, S., Paietta, E., et al. (2013). PRMT4 blocks myeloid differentiation by assembling a methyl-RUNX1-dependent repressor complex. Cell Rep 5, 1625-1638.

Wang, H., Zang, C., Taing, L., Arnett, K. L., Wong, Y. J., Pear, W. S., Blacklow, S. C., Liu, X. S., and Aster, J. C. (2014). NOTCH1-RBPJ complexes drive target gene expression through dynamic interactions with superenhancers. Proceedings of the National Academy of Sciences of the United States of America 111, 705-710.

Wang, Q., Stacy, T., Binder, M., Marin-Padilla, M., Sharpe, A. H., and Speck, N. A. (1996a). Disruption of the Cbfa2 gene causes necrosis and hemorrhaging in the central nervous system and blocks definitive hematopoiesis. Proceedings of the National Academy of Sciences of the United States of America 93, 3444-3449.

Wang, Q., Stacy, T., Miller, J. D., Lewis, A. F., Gu, T. L., Huang, X., Bushweller, J. H., Bories, J. C., Alt, F. W., Ryan, G., et al. (1996b). The CBFbeta subunit is essential for CBFalpha2 (AML1) function in vivo. Cell 87, 697-708.

Wilson, A., Murphy, M. J., Oskarsson, T., Kaloulis, K., Bettess, M. D., Oser, G. M., Pasche, A. C., Knabenhans, C., Macdonald, H. R., and Trumpp, A. (2004). c-Myc controls the balance between hematopoietic stem cell self-renewal and differentiation. Genes Dev 18, 2747-2763.

Xue, L., Pulikkan, J. A., Valk, P. J., and Castilla, L. H. (2014). NrasG12D oncoprotein inhibits apoptosis of preleukemic cells expressing Cbfbeta-SMMHC via activation of MEK/ERK axis. Blood 124, 426-436.

Yashiro-Ohtani, Y., Wang, H., Zang, C., Arnett, K. L., Bailis, W., Ho, Y., Knoechel, B., Lanauze, C., Louis, L., Forsyth, K. S., et al. (2014). Long-range enhancer activity determines Myc sensitivity to Notch inhibitors in T cell leukemia. Proceedings of the National Academy of Sciences of the United States of America 111, E4946-4953.

Yu, M., Mazor, T., Huang, H., Huang, H. T., Kathrein, K. L., Woo, A. J., Chouinard, C. R., Labadorf, A., Akie, T. E., Moran, T. B., et al. (2012). Direct recruitment of polycomb repressive complex 1 to chromatin by core binding transcription factors. Molecular cell 45, 330-343.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137.

Zhao, L., Cannons, J. L., Anderson, S., Kirby, M., Xu, L., Castilla, L. H., Schwartzberg, P. L., Bosselut, R., and Liu, P. P. (2007). CBFβ-MYH11 hinders early T-cell development and induces massive cell death in the thymus. Blood 109, 3432-3440.

Zhao, X., Jankovic, V., Gural, A., Huang, G., Pardanani, A., Menendez, S., Zhang, J., Dunne, R., Xiao, A., Erdjument-Bromage, H., et al. (2008). Methylation of RUNX1 by PRMT1 abrogates SIN3A binding and potentiates its transcriptional activity. Genes Dev 22, 640-653.

Zhu, L. J. (2013). Integrative analysis of ChIP-chip and ChIP-seq dataset. Methods Mol Biol 1067, 105-124.

Zhu, L. J., Gazin, C., Lawson, N. D., Pages, H., Lin, S. M., Lapointe, D. S., and Green, M. R. (2010). ChIPpeakAnno: a Bioconductor package to annotate ChIP-seq and ChIP-chip data. BMC bioinformatics 11, 237.

Zuber, J., Shi, J., Wang, E., Rappaport, A. R., Herrmann, H., Sison, E. A., Magoon, D., Qi, J., Blatt, K., Wunderlich, M., et al. (2011). RNAi screen identifies Brd4 as a therapeutic target in acute myeloid leukaemia. Nature 478, 524-528.

The claimed invention is:

1. A method of treating inv(16) leukemia in a subject comprising the steps of:
   administering to the subject a therapeutically effective combination of:
   a) a compound of formula (1a)

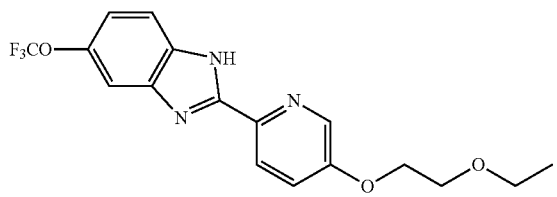

(1a)

or a pharmaceutically acceptable salt thereof; and
   b) a BRD4 inhibitor selected from JQ1 and a pharmaceutically acceptable salt thereof,
   wherein the therapeutically effective combination of the compound of formula (1a) and the BRD4 inhibitor synergistically inhibits proliferation of inv(16) leukemia cells.

2. A pharmaceutical composition comprising:
a pharmaceutically acceptable carrier and a therapeutically effective combination of:
a) a compound of the formula (1a)

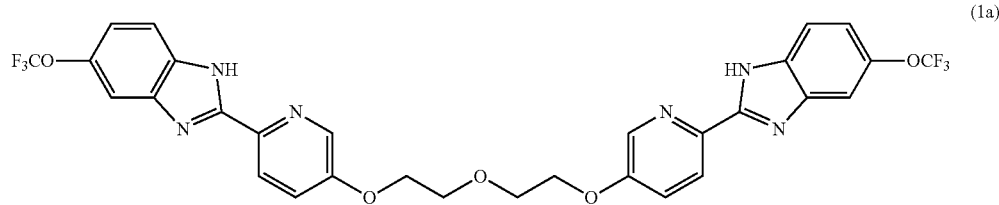 [SMILES: FC(F)(F)Oc1ccc2[nH]c(-c3ccc(OCCOCCOc4ccc(-c5nc6cc(OC(F)(F)F)ccc6[nH]5)nc4)cn3)nc2c1]

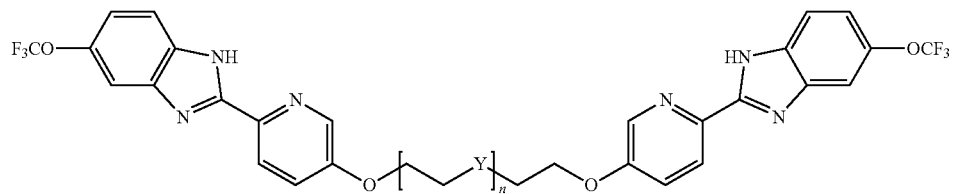

or a pharmaceutically acceptable salt thereof;

b) a BRD4 inhibitor selected from JQ1 and a pharmaceutically acceptable salt thereof; and c) a pharmaceutically acceptable excipient.

3. The method of claim 1, wherein the compound of formula (1a) and the BRD4 inhibitor are administered in a pharmaceutical composition comprising the compound of formula (1a), the BRD4 inhibitor, and a pharmaceutically acceptable carrier.

4. The method of claim 1, wherein the inv(16) leukemia is acute myeloid leukemia.

5. The method of claim 1, wherein the compound of formula (1a) and the BRD4 inhibitor are administered simultaneously.

* * * * *